(12) United States Patent
Punnonen et al.

(10) Patent No.: US 7,074,590 B2
(45) Date of Patent: Jul. 11, 2006

(54) CHIMERIC PROMOTERS

(75) Inventors: Juha Punnonen, Belmont, CA (US); Anne Wright, Woodside, CA (US); Andrey Semyonov, San Francisco, CA (US)

(73) Assignee: Maxygen, Inc., Redwood City, CA (US)

( * ) Notice: Subject to any disclaimer, the term of this patent is extended or adjusted under 35 U.S.C. 154(b) by 222 days.

(21) Appl. No.: 09/886,942

(22) Filed: Jun. 21, 2001

(65) Prior Publication Data

US 2002/0081708 A1    Jun. 27, 2002

Related U.S. Application Data

(60) Provisional application No. 60/213,829, filed on Jun. 23, 2000.

(51) Int. Cl.
    *C12P 21/00*    (2006.01)
    *C07H 21/04*    (2006.01)
    *C12N 15/00*    (2006.01)

(52) U.S. Cl. .................. 435/69.1; 536/23.1; 536/24.1; 435/320.1

(58) Field of Classification Search .................. 435/6, 435/325, 320.1, 69.1, 69.7, 440, 455; 536/23.1, 536/23.4, 24.1
See application file for complete search history.

(56) References Cited

U.S. PATENT DOCUMENTS

| | | |
|---|---|---|
| 4,762,780 A | 8/1988 | Spector et al. |
| 4,963,481 A | 10/1990 | deVilliers |
| 4,968,615 A | 11/1990 | Koszinowski et al. |
| 5,168,062 A | 12/1992 | Stinski |
| 5,273,876 A | 12/1993 | Hock et al. |
| 5,385,839 A | 1/1995 | Stinski |
| 5,512,463 A | 4/1996 | Stemmer |
| 5,514,588 A | 5/1996 | Varadaraj |
| 5,561,063 A | 10/1996 | Hock et al. |
| 5,591,639 A | 1/1997 | Bebbington |
| 5,605,793 A | 2/1997 | Stemmer |
| 5,641,665 A | 6/1997 | Hobart et al. |
| 5,658,759 A | 8/1997 | Bebbington |
| 5,688,688 A | 11/1997 | Luciw et al. |
| 5,763,239 A | 6/1998 | Short et al. |
| 5,789,228 A | 8/1998 | Lam et al. |
| 5,811,238 A | 9/1998 | Stemmer et al. |
| 5,814,473 A | 9/1998 | Warren et al. |
| 5,824,469 A | 10/1998 | Horwitz et al. |
| 5,830,696 A | 11/1998 | Short |
| 5,830,721 A | 11/1998 | Stemmer et al. |
| 5,830,745 A | 11/1998 | Hock et al. |
| 5,834,252 A | 11/1998 | Stemmer et al. |
| 5,837,458 A | 11/1998 | Minushull et al. |
| 5,849,522 A | 12/1998 | Fleckenstein et al. |
| 5,866,363 A | 2/1999 | Pieczenik |
| 5,876,997 A | 3/1999 | Kretz |
| 5,925,749 A | 7/1999 | Mathur et al. |
| 5,928,905 A | 7/1999 | Stemmer et al. |
| 5,939,250 A | 8/1999 | Short |
| 5,939,300 A | 8/1999 | Robertson et al. |
| 5,942,430 A | 8/1999 | Robertson et al. |
| 5,948,666 A | 9/1999 | Callen et al. |
| 5,958,672 A | 9/1999 | Short |
| 5,958,751 A | 9/1999 | Murphy et al. |
| 5,962,258 A | 10/1999 | Mathur et al. |
| 5,962,283 A | 10/1999 | Warren et al. |
| 5,965,408 A | 10/1999 | Short |
| 5,985,646 A | 11/1999 | Murphy et al. |
| 6,001,574 A | 12/1999 | Short et al. |
| 6,004,788 A | 12/1999 | Short |
| 6,030,779 A | 2/2000 | Short |
| 6,054,267 A | 4/2000 | Short |
| 6,057,103 A | 5/2000 | Short |
| 6,096,548 A | 8/2000 | Stemmer |
| 6,117,679 A | 9/2000 | Stemmer |
| 6,132,970 A | 10/2000 | Stemmer |
| 6,156,567 A | 12/2000 | Fischer |
| 6,165,793 A | 12/2000 | Stemmer |
| 6,168,919 B1 | 1/2001 | Short |
| 6,171,820 B1 | 1/2001 | Short |
| 6,174,673 B1 | 1/2001 | Short et al. |
| 6,180,406 B1 | 1/2001 | Stemmer |
| 6,200,959 B1 * | 3/2001 | Haynes et al. ................. 514/44 |
| 6,238,884 B1 | 5/2001 | Short et al. |

FOREIGN PATENT DOCUMENTS

| | | |
|---|---|---|
| EP | 0 173 177 B1 | 3/1986 |
| EP | 0 181 150 B1 | 5/1986 |
| EP | 0 323 997 B1 | 7/1989 |
| EP | 0911396 A2 | 4/1999 |
| EP | 0911396 A3 | 5/1999 |
| EP | 0934999 A1 | 8/1999 |
| WO | PCT 89/01036 A1 | 2/1989 |
| WO | WO 89/01036 A1 * | 2/1989 |
| WO | WO/89/01036 A2 * | 2/1989 |

(Continued)

OTHER PUBLICATIONS

Chapman, et al. Nucleic Acids Research, 1991, 19(14):3979-3986.*

Alcendor, D.J., et al., "Short Communications: Analysis of the Rhesus Cytomegalovirus Immediate-Early Gene Promoter," *Virology* 194:815-821 (1993).

(Continued)

*Primary Examiner*—Daniel M. Sullivan
(74) *Attorney, Agent, or Firm*—Margaret A. Powers; Quine Intellectual Property Law Group, P.C.

(57) ABSTRACT

This invention provides novel chimeric promoter/enhancers. The chimeric promoter/enhancers are particularly suitable for directing gene expression in mammalian cells.

46 Claims, 23 Drawing Sheets

FOREIGN PATENT DOCUMENTS

| | | |
|---|---|---|
| WO | WO 97/07205 | 2/1997 |
| WO | WO 97/20078 | 6/1997 |
| WO | WO 97/25410 | 7/1997 |
| WO | WO 97/35957 | 10/1997 |
| WO | WO 97/35966 | 10/1997 |
| WO | WO 97/44361 | 11/1997 |
| WO | PCT 97/48720 A1 | 12/1997 |
| WO | WO 97/48416 | 12/1997 |
| WO | WO 97/48717 | 12/1997 |
| WO | WO 97/48794 | 12/1997 |
| WO | WO 98/00526 | 1/1998 |
| WO | WO 98/01581 | 1/1998 |
| WO | WO 98/13485 | 4/1998 |
| WO | WO 98/13487 | 4/1998 |
| WO | WO 98/24799 | 6/1998 |
| WO | WO 98/27230 | 6/1998 |
| WO | WO 98/28416 | 7/1998 |
| WO | WO 98/31837 | 7/1998 |
| WO | WO 98/36080 | 8/1998 |
| WO | WO 98/41622 | 9/1998 |
| WO | WO 98/41623 | 9/1998 |
| WO | WO 98/41653 | 9/1998 |
| WO | WO 98/42832 | 10/1998 |
| WO | WO 98/48034 | 10/1998 |
| WO | WO 98/58085 | 12/1998 |
| WO | WO 99/07837 | 2/1999 |
| WO | WO 99/08539 | 2/1999 |
| WO | WO 99/10472 | 3/1999 |
| WO | WO 99/10539 | 3/1999 |
| WO | WO 99/19518 | 4/1999 |
| WO | WO 99/21979 | 5/1999 |
| WO | WO 99/23107 | 5/1999 |
| WO | WO 99/23236 | 5/1999 |
| WO | WO 99/29902 | 6/1999 |
| WO | PCT 99/34019 A1 | 7/1999 |
| WO | PCT 99/36557 A1 | 7/1999 |
| WO | PCT 99/41368 A2 | 8/1999 |
| WO | PCT 99/41369 A2 | 8/1999 |
| WO | PCT 99/41383 A1 | 8/1999 |
| WO | PCT 99/41402 A2 | 8/1999 |
| WO | WO 99/41368 | 8/1999 |
| WO | WO 99/41369 | 8/1999 |
| WO | WO 99/41383 | 8/1999 |
| WO | WO 99/41402 | 8/1999 |
| WO | WO 99/45154 | 9/1999 |
| WO | WO 99/57128 | 11/1999 |
| WO | PCT 99/61472 A1 | 12/1999 |
| WO | WO 99/65927 | 12/1999 |
| WO | WO 00/42560 | 7/2000 |
| WO | WO 00/42561 | 7/2000 |
| WO | WO 00/53744 | 9/2000 |
| WO | WO 00/58517 | 10/2000 |

OTHER PUBLICATIONS

Asher, D.M., et al., "Rhesus Monkey Cytomegalovirus: Persistent Asymptomatic Viruria," *Bacteriol. Proc.* 269:191 (1969).

Asher, D.M., et al., "Persistent Shedding of Cytomegalovirus in the Urine of Healthy Rhesus Monkeys," *Proc. Soc. Exp. Biol. Med.* 145:794-801 (1974).

Black, P.H., et al., "Isolation of a Cytomegalovirus from African Green Monkey," *Proc. Soc. Exp. Biol. Med.* 112(3):601-605 (1963).

Boshart, M., et al., "A Very Strong Enhancer Is Located Upstream of an Immediate Early Gene of Human Cytomegalovirus,"*Cell* 41:521-530 (1985).

Chapman, B.S., et al., "Effect of intron A from human cytomegalovirus (Towne) immediate-early gene on heterologous expression in mammalian cells," *Nucleic Acids Res.* 19(14):3979-3986 (1991).

Cockett, M.I., et al., "High level expression of tissue inhibitor of metalloproteinases in Chinese hamster ovary cells using glutamine synthetase gene amplification," *Biotechnology* 8(7):662-667 (1990).

Database Genbank 'Online! (Feb. 10, 1999) "Human Cytomegalovirus strain AD169 complete genome," Database accession No. X17403 XP-002198529 abstract.

Eaton, D.L., et al., "Construction and Characterization of an Active Factor VIII Variant Lacking the Central One-Third of the Molecule," *Biochemistry* 25(26):8343-8347 (1986).

Foecking, M.K., et al., "Powerful and versatile enhancer-promoter unit for mammalian expression vectors," *Gene* 45:101-105 (1986).

Förg, P., et al., "Superiority of the ear pinna over muscle tissue as site for DNA vaccination," *Gene Therapy* 5:789-797 (1998).

Leong, S.R., et al., "Maximizing the Genetic Diversity by Molecular Breeding: Evolution of DNA Vaccine Vectors and Adjuvant Cytokines," *1999 Winter Biotechnology Conference: Molecular Approaches to Vaccine Design,* Cold Spring Harbor, NY, Dec. 2-5, 1999.

Manthorpe, M., et al., "Gene Therapy by Intramuscular Injection of Plasmid DNA: Studies on Firefly Luciferase Gene Expression in Mice," *Human Gene Therapy* 4:419-431 (1993).

Meier, J.L., et al., "Regulation of Human Cytomegalovirus Immediate-Early Gene Expression," *Intervirology* 39:331-342 (1996).

Pasleau, F., et al., "Short Communications: Growth hormone gene expression in eukaryotic cells directed by the *Rous sarcoma* virus long terminal repeat or cytomegalovirus immediate-early promoter," *Gene* 38:227-232 (1985).

Plotkin, S.A., et al., "Candidate Cytomegalovirus Strain for Human Vaccination," *Infect. Immun* 12(3):521-527 (1975).

Punnonen, J., "Molecular Breeding of Allergy Vaccines and Antiallergic Cytokines," *Int. Arch. Allergy Immunol.* 121:173-182 (2000).

Rowe, W., "Cytopathogenic Agent Resembling Human Salivary Gland Virus Recovered from Tissue Cultures of Human Adenoids," *Proc. Soc. Exp. Biol. Med.* 92:418-424 (1956).

Thomsen, D.R., et al., "Promoter-regulatory region of the major immediate early gene of human cytomegalovirus," *Proc. Natl. Acad. Sci. USA* 81:659-663 (1984).

Wright, A., et al., "Evolution of Viruses and Vectors by DNA Shuffling: Applications in Vaccination and Gene Therapy," *1999 Winter Biotechnology Conference: Molecular Approaches to Vaccine Design,* Cold Spring Harbor, NY, Dec. 2-5, 1999.

Chang, C., et al. (1999) "Evolution of a cytokine using DNA family shuffling." *Nature Biotechnology* 17:793-797.

Christians, F.C. et al., (1999) "Directed evolution of thymidine kinase for AZT phosphorylation using DNA family shuffling." *Nature Biotechnology* 17:259-264.

Coco et al., (2001) "DNA shuffling method for generating highly recombined genes and evolved enzymes" *Nature Biotechnology* vol. 19 pp. 354-359.

Crameri et al., (1993) "10(20)-Fold aptamer library amplification without gel purification," *Nuc. Acids Res.* 21(18):4410.

Crameri, A. & Stemmer W.P.C. (1995) "Combinatorial multiple cassette mutagenesis creates all the permutations of mutant and wildtype cassettes." *Biotechniques* 18:194-195.

Crameri, A. et al. (1996) "Improved green fluorescent protein by molecular evolution using DNA shuffling." *Nature Biotechnology* 14:315-319.

Crameri, A. et al. (1996) "Construction and evolution of antibody-phage libraries by DNA shuffling." *Nature Medicine* 2:100-103.

Crameri, A. et al., (1997) "Molecular evolution of an arsenate detoxification pathway by DNA shuffling." *Nature Biotechnology* 15:436-438.

Crameri, A. et al., (1998) "DNA shuffling of a family of genes from diverse species accelerates directed evolution." *Nature* 391:288-291.

Gates, C.M. et al., (1996) "Affinity selective isolation of ligands from peptide libraries through display on a lac repressor headpiece dimer". *Journal of Molecular Biology* 255;373-386.

Minshull, J., Stemmer, W.P.C. (1999) "Protein evolution by molecular breeding." *Current Opinion in Chemical Biology* 3:284-290.

Ness, J. et al., (1999) "DNA shuffling of subgenominc sequences of subtilisin." *Nature Biotechnology* 17:893-896.

Patten, P.A. et al., (1997) "Application of DNA Shuffling to Pharmaceuticals and Vaccines." *Current Opinion in Biotechnology* 8:724-733.

Pelletier, Joelle N., (2001) "A Rachitt for our toolbox" *Nature Biotechnology* vol. 19, p. 314-315.

Stemmer, W.P.C. (1994) "DNA Shuffling by random fragmentation and reassembly: In vitro recombination for molecular evolution." *PNAS* 91:10751.

Stemmer, W.P.C. (1994) "Rapid evolution of a protein in vitro by DNA shuffling." *Nature* 370:389-391.

Stemmer, W.P.C. (1995) "The Evolution of Molecular Computation." *Science* 270:1510.

Stemmer, W.P.C. (1995) "Searching Sequence Space." *Bio/Technology* 13:549-553.

Stemmer, W.P.C. (1996) "Sexual PCR and Assembly PCR." In: *The Encyclopedia of Molecular Biology*. VCH Publishers, New York. pp. 447-457.

Stemmer, W.P.C. & Soong, N.W. (1999) "Molecular breeding of viruses for targeting and other clinical properties." *Tumor Targeting* 4:59-62.

Zhang, J. et al., (1997) "Directed evolution of an effective fucosidase from a galactosidase by DNA shuffling and screening." *Proceedings of the National Academy of Sciences, USA* 94:4504-4509.

* cited by examiner

Figure 2: Enrichment of chimeric promoter libraries by FACS sorting

Figure 3: Diverse activities of chimeric promoter sequences in transfected cells Figure 4: Luciferase expression in muscle 7 days after plasmid injection Figure 5: Comparison of Luciferase expression from clone 6A8 and parental clones Figure 6A: Antibody responses following injection with β-galactosidase-encoding plasmid Figure 6B: Improved Ab Response by Shuffled Promoter Figure 7: Chimeric promoter 6A8 is functional in human muscle tissue Figure 8A: Comparison of 18 chimeric promoter sequences generated by DNA shuffling using CMV promoter nucleic acid sequences from AD169 and Towne human strains and Rhesus and Vervet monkey strains as parental sequences.

Figure 8B: Comparison of 18 chimeric promoter sequences generated by DNA shuffling using CMV promoter nucleic acid sequences from AD169 and Towne human strains and Rhesus and Vervet monkey strains as parental sequences.

Figure 8C: Comparison of 18 chimeric promoter sequences generated by DNA shuffling using CMV promoter nucleic acid sequences from AD169 and Towne human strains and Rhesus and Vervet monkey strains as parental sequences.

Figure 8D: Comparison of 18 chimeric promoter sequences generated by DNA shuffling using CMV promoter nucleic acid sequences from AD169 and Towne human strains and Rhesus and Vervet monkey strains as parental sequences.

Figure 8E: Comparison of 18 chimeric promoter sequences generated by DNA shuffling using CMV promoter nucleic acid sequences from AD169 and Towne human strains and Rhesus and Vervet monkey strains as parental sequences.

Figure 8F: Comparison of 18 chimeric promoter sequences generated by DNA shuffling using CMV promoter nucleic acid sequences from AD169 and Towne human strains and Figure 8G: Comparison of 18 chimeric promoter sequences generated by DNA shuffling using CMV promoter nucleic acid sequences from AD169 and Towne human strains and Rhesus and Vervet monkey strains as parental sequences.

Figure 8H: Comparison of 18 chimeric promoter sequences generated by DNA shuffling using CMV promoter nucleic acid sequences from AD169 and Towne human strains and Rhesus and Vervet monkey strains as parental sequences.

Figure 8I: Comparison of 18 chimeric promoter sequences generated by DNA shuffling using CMV promoter nucleic acid sequences from AD169 and Towne human strains and Rhesus and Vervet monkey strains as parental sequences.

Figure 10A

```
                                        1   ATA.....TGAGGCTATATGCCGATAGAGGCGACATCAAGCTGGCACATGGCCAATGCAT    60
Towne_promoter_fr_PCR_prod_seq
Rhesus_monkey_PCR_prod_821bp                ACT....TGGCACGGTGCCAA..GTTTGGGGCGGGGTC...TTGGCACCGTGCCAA.....
Vervet_(Simian)_PCR_product_seq             ATTGAATTGGCATGGTGTGCCAATAATGGCGGC...CATA...TTGGCTATATGCCA.....

61   ATCGATCTATACATTGAATCAATATTGGCAATTAGCCATATATTAGTCATATATATAGC   120
Towne_promoter_fr_PCR_prod_seq
Rhesus_monkey_PCR_prod_821bp                ...GTCCGCCATATTGGTTTGGCAT.....ATGTCCAATATTATTGAT...CCATATAGC
Vervet_(Simian)_PCR_product_seq             ...........GGATCAATAT......ATAGGCAATATC...........CAATATGGC 121   ATAAATCAATATTGGCTATTTGGCCATTGCATACGTTGTATCTATATCATAATATGTACAT   180
Towne_promoter_fr_PCR_prod_seq
Rhesus_monkey_PCR_prod_821bp                CAATATCCAATATGGCTAATAGCCA............GGTTCAATAGAATGGCCAATAAGC
Vervet_(Simian)_PCR_product_seq             CCTATGCCAATATGGCTATTGGCCA...........GGTTCAATACTATGTATTGGCCCT 181   TTATATTGGCTCATGTCCAATATGACCGCCATGTTGACATTGATTATTCACTAGTT..AT   240
Towne_promoter_fr_PCR_prod_seq
Rhesus_monkey_PCR_prod_821bp                CAATAT..GCCATTGGCCAACATGGCAA.TGGGCCAGTATTGATTATAGCCAATAT..AT
Vervet_(Simian)_PCR_product_seq             ATGCCA...TATAGTATTCCATATATGGGTTTTCCTATTGACGTAGATAGCCCCTCCAAT
```

Figure 10B

```
                                                                                    300
241
Towne_promoter_fr_PCR_prod_seq    TAATAGTA......ATCAATTACGGGGTCATTAGTTCATAGCCCATATATGGAGTTCCGC
Rhesus_monkey_PCR_prod_821bp      AGGCAATA......ATCCATATTGG...CATATGTCCATATTGCCTATACCCATATTGGC
Vervet_(Simian)_PCR_product_seq   GGGCGGTCCCATATACCATATATGG...GGCTTCCTAATACCGCCATAGCCACTCCCCC 360
301
Towne_promoter_fr_PCR_prod_seq    GT...T..ACATAACTTACGGTAAATGGCCCGCCTCGTGACCGCCCAACGACCCCCGCCC
Rhesus_monkey_PCR_prod_821bp      TTATGT..CCATTACCAATACCATATATGGGTCTTCCTATATACGTCATAGGTACCGCCC
Vervet_(Simian)_PCR_product_seq   AT...TGACCTCAATGGTCTCTATATATGGTCTTTCCTATTGACGTCATATGGGCGTCC 420
361
Towne_promoter_fr_PCR_prod_seq    .ATTGACGT.....................................................CAA
Rhesus_monkey_PCR_prod_821bp      .ATTGACGTAATATGGATACGCCTCCATTGACGTCAATGGGAGGATTAATATACGTCAC
Vervet_(Simian)_PCR_product_seq   TATTGACGTA.TATGGCGCCTCCCCCATTGACGTCAATTACGGTAAATGGCCCGCCTGGC 480
421
Towne_promoter_fr_PCR_prod_seq    TAATGACGTATGTTCCCAT...............AGTAACGCCAATAGGG..ACTTTCCA
Rhesus_monkey_PCR_prod_821bp      TAATACCGCCCATTGACGTGTATAGGACCGTCAATAGGCCCACCTCCCA
Vervet_(Simian)_PCR_product_seq   T..CAATGCCCATTGACGT.....................CAATAGGACCACCACCA
```

Figure 10C

```
                                          481                                                          540
Towne_promoter_fr_PCR_prod_seq            TTGACGTCAATGGGTGGAGTATTTACGGTAAACTGCCCACTT.............GGCAGTAC
Rhesus_monkey_PCR_prod_821bp              TTGACGTCAATGGG...........GTGGCCCATTGCCCATTC....................
Vervet_(Simian)_PCR_product_seq           TTGACGTCAATGGG...........ATGGCTCATTGCCCATTCATATCCGTTC...........

541                                                          600
Towne_promoter_fr_PCR_prod_seq            ATCAAGTGTATCATATGCCAAGTCCGGCCCCCTATTGACGTCAATGACGGTAAATGGCCC
Rhesus_monkey_PCR_prod_821bp              ..........................CCACGCCCCCTATTGACGTCAATGACGGTAAATGGCC.
Vervet_(Simian)_PCR_product_seq           ..........................TCACGCCCCCTATTGACGTCAATGACGGTAAATGGCC.

601                                                          660
Towne_promoter_fr_PCR_prod_seq            GCCTGGGCATTATGCCCAGTACATGACCTTACGGGACTTTCCTACTTGGCAGTACATC..T
Rhesus_monkey_PCR_prod_821bp              ...........................................CACTTGGCAGTACATCAAT
Vervet_(Simian)_PCR_product_seq           ...........................................CACTTGGCAGTACATCAAT 661                                                          720
Towne_promoter_fr_PCR_prod_seq            ACGTATTAGTCATCGCTATTACCATGGTGATGCGGTTTTGGCAGTACACCAA.........
Rhesus_monkey_PCR_prod_821bp              ACCTATTAATAGTAACT..TGGCAAGTAAATGGTACTTGGCAGTACACCAAGG.TACAT
Vervet_(Simian)_PCR_product_seq           ATCTATTAATAGTAACT..TGGCAAGTACATTACTATTGGCAAGTACGCCAAGGTACAT
```

Figure 10D

```
                                      721                                                           780
Towne_promoter_fr_PCR_prod_seq        ............TGGGGCGTGGATAGCGGT..TTGACTCACGGGGATTCCAAGTCTC
Rhesus_monkey_PCR_prod_821bp          TGGCAG.TACTCCCATTGACGTCAATGGCGTGGCGTAAATGGCCCGCAATGGCTGCCAAGTACA
Vervet_(Simian)_PCR_product_seq       TGGCAGGTACTCCCATTGACGTCAATGGCCGGTAAATGGCCCGGCATGGCTGCCAAGTACA 781                                                           840
Towne_promoter_fr_PCR_prod_seq        ...CACCCCCATTGACGTCAATGGAGTTTGTTTTGGCACCAAAATCAACGGGACTTTCCA
Rhesus_monkey_PCR_prod_821bp          ...TGCCC.ATTGACGTCAATGGGG............
Vervet_(Simian)_PCR_product_seq       ACATCCCC.ATTGACGTCAATGGGAA...........

841                                                           900
Towne_promoter_fr_PCR_prod_seq        AAATGTCGTAATAACCCCGCCCGTTGACGCAAATGGGCG.................
Rhesus_monkey_PCR_prod_821bp          ............CGGTCCTATGACGTCAATGGGCG..................
Vervet_(Simian)_PCR_product_seq       ............GGGGCAATGACGACGCAAATGGGCGTTCCATTGACGTAAATGGCG 901                                                           960
Towne_promoter_fr_PCR_prod_seq        GTAGGCGTGTACGGTGGGAGGTCTATATAAGCAGAGCTCGTTTAGTGAACCGTCAGATCG
Rhesus_monkey_PCR_prod_821bp          GTAGGCGTGC..CTATGGGCGGTCTATATAAGCAATGCACGTTTAGGGAACCGCCATTCTG
Vervet_(Simian)_PCR_product_seq       GTAGGCGTGCCTAATGGGAGGTCTATATAAGCAATGCTCGTTTAGGGAACCGCCATTCTG
```

Figure 10E

```
                                    961                                                                    1020
Towne_promoter_fr_PCR_prod_seq      CCTGGAGACGCCATCCAGCTGTTTGACCTCCAT.AGAAGACACCGGG.ACCGATCCAG
   Rhesus_monkey_PCR_prod_821bp     CCTGGGGACGTCG..........GAGGAGCACCAT.AGAAGGTACCGGGACCGATCCAG
  Vervet_(Simian)_PCR_product_seq   CCTGGGGACGTCG..........GAGGAGCTCCATTGGAAGAGACACCGGG.ACCGATCCAG 1021                    1057
Towne_promoter_fr_PCR_prod_seq      CCTCCGCGGCGGGGAACGGTGCATTGGAACGCGGATT         SEQ ID NO:20
   Rhesus_monkey_PCR_prod_821bp     CCTCCATAGCCGGGAAGGGTGCATTGGAACGCGGATA         SEQ ID NO:22
  Vervet_(Simian)_PCR_product_seq   CCTCCATAGCCGGGACGGTGCATTGGAATGCGGATA          SEQ ID NO:23
``` us 7,074,590 B2

SEQUENCE LISTING

<160> NUMBER OF SEQ ID NOS: 40

<210> SEQ ID NO 1
<211> LENGTH: 1766
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1

```
atatgaggct atatcgccga tagaggcgac atcaagctgg cacatggcca atgcatatcg     60
atctatacat taaatcaata ttggcaatta gccatatttg tcattggtta tatagcataa    120
atcaatattg gctattggcc attgcatacg ttgtatctat atcataatat gtacatttat    180
attggctcat gtccaatacg accgccatgt tgacattgat tattgactag ttattaatag    240
taatcaatta cggggtcatt agttcatagc ccatatatgg agttccgcgt tacataactt    300
acggtaaatg gcccgcctgg ctgaccgccc aacgaccccc gcccattgac gtcaataatg    360
acgtatgttc ccatagtaac gccaataggg actttccatt gacgtcaatg ggtggagtat    420
ttacggtaaa ctgcccactt ggcagtacat caagtgtatc atatgccaag tccgccccct    480
attgacgtca atgacggtag acgtcaatgg gtggagtatt tacggtaaac tgcccacttg    540
gcagtacatc aagtgtatca tatgccaagt ccgcccccta ttgacgtcaa tgacggtagt    600
tttggcagta caccaatggg cgtggatagc ggtttgactc acgggatttt ccaagtctcc    660
accccattga cgtcaatggg agtttgtttt ggcaccaaaa tcaacgggac cttccaaaat    720
gtcgtaataa ccccgccccg ttgacgcaaa tgggcggtag gcgtgtacgg tgggaggtct    780
atataagcaa tgctcgttta gtgaaccgtc agatcgcctg gagacgccat ccacgctgtt    840
ttgacctcca tagaagacac cgggaccgat ccagcctccg cggccgggaa cggtgcattg    900
gaacgcggat tccccgtgcc aagagtgacg taagtaccgc ctatagactc tataggcaca    960
cccctttggc tcttatgcat gctatactgt ttttggcttg ggtctatac acccccgctt   1020
ccttatgcta taggtgatgg tatagcttag cctataggtg tgggttattg accattattg   1080
accactcccc tattggtgac gatactttcc attactaatc cataacatgg ctctttgcca   1140
caactatctc tattggctat atgccaatac tctgtccttc agagactgac acggactctg   1200
tatttttaca ggatggggtc ccatttatta tttacaaatt cacatataca acaccaccgt   1260
ccccagtgcc cgcagttttt gttaaacata gcgtgggatc tccacgcaaa tctcgggtac   1320
gtgttccgga catgggctct tctccggtag cggcggagct tccacatccg agccctggtc   1380
ccatgcctcc agcggctcat ggtcgctcgg cagctccttg ctcctaacag tggaggccag   1440
acttaggcac agcacaatgc ccaccaccac cagtgtgccg cacaaggccg tggcggtagg   1500
gtatgtgtct gaaaatgagc tcggagattg ggctcgcacc gctgacgcag atggaagact   1560
taaggcagcg gcagaagaag atgcaggcag ctgagttgtt gtattctgat aagagtcaga   1620
ggtaactccc gttgcggtgc tgttaacggt ggagggcagt gtagtctgag cagtactcgt   1680
tgctgccgcg cgcgccacca gacataatag ctgacagact aacagactgt tcctttccat   1740
gggtcttttc tgcagtcacc gtcctt                                        1766
```

<210> SEQ ID NO 2
<211> LENGTH: 1758
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 2

| | | | | | |
|---|---|---|---|---|---|
| atatgaggct | atatcgccga | tataggcgac | atcaagctgg | cacatagcca | atgcatatcg | 60 |
| atctatacgt | tgaatcaata | ttggccatta | gccatattat | tcattggtta | tatagcatag | 120 |
| atcaatattg | gctattggcc | attgcatacg | ttgtatctat | atcataatat | gtacatttat | 180 |
| attggctcat | gtccaatatg | actgccatgt | tgacattgat | tatttgactag | ttattaatag | 240 |
| taatcaatta | cggggtcatt | agttcatagc | ccatatatgg | agttccgcgt | tacataactt | 300 |
| acggtaaatg | gcccgcctgg | ctgaccgccc | aacgaccccc | gcccattgac | gtcaataatg | 360 |
| acgtatgttc | ccatagtaac | gccaataggg | actttccatt | gacgtcaatg | ggtggagtat | 420 |
| ttacggtaaa | ctgctcactt | ggcagtacat | caagtgtatc | atatgccaag | tacgccccct | 480 |
| attgacgtca | atgacggtaa | atggcccgcc | tggcattatg | cccagtacat | gaccttacgg | 540 |
| gactttccta | cttggcagta | catctacgta | ttagtcatcg | ctattaccat | ggtgatgcgg | 600 |
| ttttggcagt | acaccaatgg | gcgtggatag | cggtttgact | cacggggatt | tccaagtctc | 660 |
| caccctattg | acgtcaatgg | gagtttgttt | tggcaccaaa | atcaacggga | ctttccaaaa | 720 |
| tgtcgtaata | accccgcccc | gttgacgcaa | atgggcggta | ggcgtgtacg | gtgggaggtc | 780 |
| tatataagca | gagctcgttt | agggaaccgc | cattctgcct | ggggacgccg | gaggagctcc | 840 |
| attggaagag | accgggaccg | atccagcctc | cgcggccggg | aacggtgcat | tggaacgcgg | 900 |
| attccccgtg | ccgagagtga | cgtaagtacc | gcctatagac | tctataggca | cacccctttg | 960 |
| gctcttatgc | atgctatact | gtttttggct | tggggcctat | acaccccgc | ttccttatgc | 1020 |
| tataggtgat | ggtatagctt | agcctatagg | tgtgggttat | tgaccattat | tgaccatccc | 1080 |
| cctattggtg | acgatacttt | ccattactaa | tccataacat | ggctctttgc | cacagctatc | 1140 |
| tctattggct | atatgccaat | actctgtcct | tcagagactg | cacggactc | tgtatttta | 1200 |
| caggatgggg | tctcatttat | tatttacaaa | ttcacatata | caacaacgcc | gtccccgtg | 1260 |
| cccgcagttt | ttattaaaca | tagcgtggga | tctccacgcg | aatctcgggt | acgtgttccg | 1320 |
| gacatgggct | cttctccggt | aggggcggag | cttccacatc | cgagccctgg | tcccatgcct | 1380 |
| ccagcggctc | atggtcgctc | ggcagctcct | tgctcctaac | agtggaggcc | agacttaggc | 1440 |
| acagcacaat | gcccaccacc | accagtgtgc | cgcacaaggc | cgtggcggta | gggtatgtgt | 1500 |
| ctgaaaatga | gctcggagct | tggctcgca | ccgctgacgc | agatgaaga | cttaaggcag | 1560 |
| cggcagaaga | agatgcaggc | agctgagttg | ttgtattctg | ataagagtca | gaggtaactc | 1620 |
| ccgttgcggt | gctgttaacg | gtggagggca | gtgtagtctg | agcagtactc | gttgctgccg | 1680 |
| cgcgcgccac | cagacataat | agctgacaga | ctaacagact | gttcctttcc | atgggtcttt | 1740 |
| tctgcagtca | ccgtcctt | | | | | 1758 |

<210> SEQ ID NO 3
<211> LENGTH: 897
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 3

| | | | | | |
|---|---|---|---|---|---|
| atatgaggct | atatcgccga | tagaggcgac | atcaagctgg | cacatggcca | atgcatatcg | 60 |
| atctatacat | tgaatcaata | ttggccatta | gccatattat | tcattggtta | tatagcataa | 120 |
| atcaatattg | gctattggcc | attgcatacg | ttgtatccat | atcataatat | gtacatttat | 180 |
| attggctcat | gtccaacatt | accgccatgt | tgacattgat | tattgactag | ttattaatag | 240 |
| taatcaatta | cggggtcatt | agttcatagc | ccatatatgg | agtcccgcgt | tacataactt | 300 |
| acggtaaatg | gcccgcctgg | ctgaccgccc | aacgacccc | gcccattgac | gtcaataatg | 360 |
| acgtatgttc | ccatagtaac | gccaataggg | actttccatt | gacgtcaatg | ggtgggtat | 420 |
| ttacggtaaa | ctgcccactt | ggcagtacat | caagtgtatc | atatgccaag | tccgccccct | 480 |
| attgacgtca | atgacggtaa | atgggccgcc | tggcattatg | cccagtacat | gaccttacgg | 540 |
| gactttccta | cttggcagta | catctacgta | ttagtcatcg | ctattaccat | ggtgatgcgg | 600 |
| ttttggcagt | acaccaatgg | gcgtggatag | cggtttgact | cacggggatt | tccaagtctc | 660 |
| caccctattg | acgtcaatgg | gagtttgttt | tggcaccaaa | atcaacggga | ctttccaaaa | 720 |
| tgtcgtaata | actccgcccc | gtcgacgcaa | atgggcggta | ggcgtgtacg | gtgggaggtc | 780 |
| tatataagca | atgctcgttt | agggaaccgc | cattctgcct | ggggacgccg | gaggagcacc | 840 |
| atagaagaca | ccgggaccga | tccagcctcc | atagccgggg | acggtgcatt | ggaacgc | 897 |

<210> SEQ ID NO 4
<211> LENGTH: 1716
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4

| | | | | | |
|---|---|---|---|---|---|
| atatgaggct | atatcgccga | tagaggcgac | atcaagctgg | cacatggcca | atgcatatcg | 60 |
| atctatacat | tgaatcaata | ttggcaatta | gccatattag | tcattggtta | tatagcataa | 120 |
| atcaatattg | gctattggcc | atcgcatacg | ttgtatctat | atcataatat | gtacatttat | 180 |
| attggctcat | gtccaatatg | accgccatgt | tgacattgat | tattgactag | ttattaatag | 240 |
| taatcaatta | cggggtcatt | agttcatagc | ccatatatgg | agttccgcgt | tacataactt | 300 |
| acggtaaatg | gcccgcctgg | ctgaccgccc | aacgacccc | gcccattgac | gtcaatagtg | 360 |
| acgtatgttc | ccatagtaac | gccaataggg | actttccatt | gacgtcaatg | ggtggagtat | 420 |
| ttacggtaaa | ctgcccactt | ggcagtacat | caagtgtatc | atatgccaag | tccgccccct | 480 |
| attgacgtca | atgacggtaa | atgggccgcc | tggcattatg | cccagtacat | gaccttacgg | 540 |
| gactttccta | cttggcagta | catctacgta | ttagtcatcg | ctattaccat | ggtgatgcgg | 600 |
| ttttggcagt | acaccaatgg | gcgtggatag | cggtttgact | cacggggatt | tccaagtctc | 660 |
| caccccattg | acgtcaatgg | ggcggtccta | tgacgcaaat | gggcggtagg | cgtgtacggt | 720 |
| gggaggtcta | tataagcaga | gctcgtttag | tgaaccgtca | gatcgcctgg | agacgccatc | 780 |
| cacgctgttt | tgacctccat | agaagacacc | gggaccgatc | cagcctccgc | ggccgggaac | 840 |
| ggtgcattgg | aacgcggatt | ccccgtgcca | agagtgacgt | aagtaccgcc | tatagagtct | 900 |
| ataggcccac | ccccttggct | tcttatgcat | gctatactgt | ttttggcttg | ggtctatac | 960 |
| accccgcctt | ccttatgcta | taggtgatgg | tatagcttag | cctataggtg | tgggttattg | 1020 |
| accattattg | accactcccc | tattggtgac | gatactttcc | attactaatc | cataacatgg | 1080 |

```
ctctttgcca caactatctc tattggctat atgccaatac actgtccttc agagactgac    1140
acggactctg tattttttaca ggatggggtc ccatttatta tttacaaatt cacatataca   1200
acaacgccgt cccccgtgcc cgcagttttt attaaacata gcgtgggatc tccacgcgaa    1260
tctcgggtac gtgatccgga catgggctct ctccggtag cggtggagct tccacatccg     1320
agccctggtc ccatgcctcc agcggctcat ggtcgctcgg cagctccttg ctcctaacag    1380
tggaggccag acttatgcac agcacaatgc ccaccaccac cagtgtgccg cacaaggccg    1440
tggcggtagg gtatgtgtct gaaaatgagc tcggagattg ggctcgcacc gctgacgcag    1500
atggaagact taaggcagcg gcagaagaag atgcaggcag ctgagttgtt gtattctgat    1560
aagagtcaga ggtaactccc gttgcggtgc tgttaacggt ggagggcagt gtagtctgag    1620
cagtactcgt tgctgccgcg cgcgccacca gacataatag ctgacagact aacagactgt    1680
tcctttccat gggtcttttc tgcagtcacc gtcctt                              1716
```

<210> SEQ ID NO 5
<211> LENGTH: 1767
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5

```
atatgaggct atatcgccga tagaggcgac atcaagctgg cacatggcca atgcatatcg     60
atctatacat tgaatcaata ttggccatta gccatattat tcattggtta tatagcataa    120
atcaatattg gctattggcc actgcatacg ttgtatctat atcataatat gtacatttat    180
attggctcat gtccaatatg accgccatgt tgacattgat tattgactag ttattaatag    240
taatcaatta cggggtcatt agttcatagc ccatatatgg agttccgcgt tacataactt    300
acggtaaatg gcccgcctgg ctgaccgccc aacgaccccc gcccattgac gtcaataatg    360
acgtatgtcc ccatagtaac gccaataggg actttccatt gacgtcaatg ggtggagtat    420
ttacggtaaa ctgcccactt ggcagtacat caggtgtatc atatgccaag tacgccccct    480
attgacgtca atgacggtaa atggcccgcc tggcattatg cccagtacat gaccttacgg    540
gactttccta cttggcagta catctacgta ttagtcatcg ctattaccat ggtgatgcgg    600
ttttggcagt acaccaatgg gcgtggatag cggtttgact cacggggatt tccaagtctc    660
caccccattg acgtcaatgg gagtttgttt tggcaccaaa atcaacggga ctttccaaaa    720
tgtcgtaata accccgcccc gttgacgcaa atgggcggta ggcgtgtacg gtgggaggtc    780
tatataagca gagctcgttt agtgaaccgt cagatcgcct ggagacgcca tccacgctgt    840
tttgacctcc atagaagaca ccgggaccga tccagcctcc gcggccggga acggtgcatt    900
ggaacgcgga ttccccgtgc caagagtgac gtaagtaccg cctatagact ctataggcac    960 accccttgg ctcttatgca tgctatactg tttttggctt ggggcctata caccccgct     1020 tccttatgct ataggtgatg gtatagctta gcctataggt gtgggttatt gaccattatt    1080
gaccactccc ctattggtga cgatactttc cattactaat ccataacagg gctctttgcc    1140
acaactatct ctattggcta tatgccaata ctctgtcctt cagagactga cacggactct    1200
gtatttttac aggatggggt ctcatttatt atttacaaat tcacatatac aacaacgccg    1260
tcccccgtgc ccgcagtttt tattaaacat agcgtgggat ctccacgcga atctcgggta    1320
cgtgttccgg acatgggctc ttctccggta gcggtggagc ttccacatcc gagccctggt    1380
```

-continued

| | |
|---|---|
| cccatgcctc cagcggctca tggtcgctcg gcagctcctt gctcctaaca gtggaggcca | 1440 |
| gacttatgca cagcacaatg cccaccacca ccagtgtgcc gcacaaggcc gtggcggtag | 1500 |
| ggtatgtgtc tgaaaatgag ctcggggagc gggcttgcac cgctgacgca gatggaagac | 1560 |
| ttaaggcagc ggcagaagaa gatgcaggca gctgagttgt tgtattctga taagagtcag | 1620 |
| aggtaactcc cgttgcggtg ctgttaacgg tggagggcag tgtagtctga gcagtactcg | 1680 |
| ttgctgccgc gcgcgccacc agacataata gctgacagac taacagactg ttcctttcca | 1740 |
| tgggtctttt ctgcagtcac cgtcctt | 1767 |

<210> SEQ ID NO 6
<211> LENGTH: 1766
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6

| | |
|---|---|
| atatgaggct atatcgccga tagaggcgac atcaagctgg cacatggcca atgcatatcg | 60 |
| atctatacat tgaatcaata ttggcaatta gccatattag tcattggtta tatagcataa | 120 |
| atcaatattg gctattggcc attgcatacg ttgtatctat atcataatat gtacatttat | 180 |
| attggctcat gtccaacatt accgccatgt tgacattgat tattgactag ttattaatag | 240 |
| taatcaatta cggggtcatt agttcatagc ccatatatgg agttccgcgt tacataactt | 300 |
| acggtaaatg gcccgcctgg ctgaccgccc aacgacccc gcccattgac gtcaataatg | 360 |
| acgtatgttc ccatagtaac gccaataggg actttccatt gacgtcaatg ggtggagtat | 420 |
| ttacggtaaa ctgcccactt ggcagtacat caagtgtatc atatgccaag tccgcccccc | 480 |
| tattgacgtc aatgacggta aatggcccgc ctggcattat gcccagtaca tgaccttacg | 540 |
| ggactttcct acttggcagt acatctacgt attagtcatc gctattacca tggtgatgcg | 600 |
| gttttggcgg tacatcaatg ggcgtggata gcggtttgac tcacggggat ttccaagtct | 660 |
| ccaccctatt gacgtcaatg ggagtttgtt ttggcaccaa atcaacggg actttccaaa | 720 |
| atgtcgtaat aaccccgccc cgttgacgca atgggcggt aggcgtgtac ggtgggaggt | 780 |
| ctatataagc agagctcgtt tagtgaaccg tcagatcgcc tggagacgcc atccacgctg | 840 |
| ttttgacctc catagaagac accgggaccg atccagcctc cgcggccggg aacggtgcat | 900 |
| tggaacgcgg attccccgtg ccaagagtga cgtaagtacc gcctatagac tctataggca | 960 |
| caccccttg gctcttatgc atgctatact gttttggct tggggcctat acaccccgc | 1020 |
| ttccttatgc tataggtgat ggtatagctt agcctatagg tgtgggttat tgaccattat | 1080 |
| tgaccactcc cctattggtg acgatacttt ccattactaa tccataacat ggctctttgc | 1140 |
| cacaactatc tctattggct atatgccaat actctgtcct tcagagactg acacggactc | 1200 |
| tgtatttta caggatgggg tcccatttat tatttacaaa ttcacatata caacaccacc | 1260 |
| gtccccagtg cccgcagttt ttattaaaca tagcgtggga tctccacgcg aatctcgggt | 1320 |
| acgtgttccg gacatgggct cttctccggt aggggcggag cttccacatc cgagccctgg | 1380 |
| tcccatgcct ccagcggctc atggtcgctc ggcagctcct cgctcctaac agtgtgaggcc | 1440 |
| agacttaggc acagcacaat gcccaccacc accagtgtgc cgcacaaggc cgtggcggta | 1500 |
| gggtatgtgt ctgaaaatga gctcggagtg ggcttgcacc gctgacgcat ttggaagact | 1560 |
| taaggcagcg gcagaagaag atgcaggcag ctgagttgtt gtgttctgat aagagtcaga | 1620 |

| | | |
|---|---|---|
| ggtaactccc gttgcggtgc cgttaacggt ggagggcagt gtagtctgag cagtactcgt | 1680 | |
| tgctgccgcg cgcgccacca gacataatag ctgacagact aacagactgt tcctttccat | 1740 | |
| gggtcttttc tgcagtcacc gtcctt | 1766 | |

<210> SEQ ID NO 7
<211> LENGTH: 1715
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 7

| | |
|---|---|
| atatgaggct atatcgccga tagaggcgac atcaagctgg cacatggcca atgcatatcg | 60 |
| atctatacat tgaatcaata ttggcaatta gccatattag tcattggtta tatagcataa | 120 |
| atcaatattg gctattggcc attgcatacg ttgtatctat atcataatat gtacatttat | 180 |
| attggctcat gtccaatatg accgccatgt tgacattgat tattgactag ttattaatag | 240 |
| taatcaatta cggggtcatt agttcatagc ccatatatgg agttccgcgt tacatagctt | 300 |
| acggtaaatg gcccgcctgg ctgactgccc aacgaccccc gcccattgac gtcaataacg | 360 |
| acgtatgttc ccatagtaac gccaataggg actttccatt gacgtcaatg ggtggagtat | 420 |
| ttacggtaaa ctgcccactt ggcagtacat caagtgtatc atatgccaag tacgccccct | 480 |
| attgacgtca atgacggtaa atggcccgcc tggcattatg cccagtacat gaccttacgg | 540 |
| gactttccta cttggcagta catctacgta ttagtcatcg ctattaccat ggtgatgcgg | 600 |
| ttttggcagt acatcaatgg gcgtggatag cagtttgact cacggggatt tccaagtctc | 660 |
| caccccattg acgtcaatgg gcggtcctat gacgcaaat gggcggtagg cgtgtacggt | 720 |
| gggaggtcta tataagcaga gctcgtttag tgaaccgtca gatcgcctgg agacgccatc | 780 |
| cacgctgttt tgacctccat agaagacacc gggaccgatc cagcctccgc ggccgggaac | 840 |
| ggtgcattgg aacgcggatt ccccgtgcca agagtgacgt aagtaccgcc tatagactct | 900 |
| ataggcacac ccctttggct cttatgcatg ctatactgtt tttggcttgg ggcctataca | 960 |
| ccccccgctt cttatgctat aggtgatggt atagcttagc ctataggtgt gggttattga | 1020 |
| ccattattga ccactcccct attggtgacg atactttcca ttactaatcc ataacatggc | 1080 |
| tctttgccac aactatctct attggctata tgccaatact ctgtccttca gagactgaca | 1140 |
| cggactctgt atttttacag gatggggtcc catttattat ttacaaattc acatatacaa | 1200 |
| caacgccgtc ccccgtgctc gcagtttta ttaaacatag cgtgggatct ccacgcgaat | 1260 |
| ctcgggtacg tgttccggac atgggctctt ctccggtagg gcggagctt ccacatccga | 1320 |
| gccctggtcc catgcctcca gcggctcatg gtcgctcggc agctccttgc tcctaacagt | 1380 |
| ggaggccaga cttaggcaca gcacgatgcc caccaccacc agtgtgccgc acaaggccgt | 1440 |
| ggcggtaggg tatgtgtctg aaaatgagct cggagattgg gctcgcaccg ctgacgcaga | 1500 |
| tggaagactt aaggcagcgg cagaagaaga tgcaggcagc tgagttgttg tattctgata | 1560 |
| agagtcagag gtaactcccg ttgcggtgct gttaacggtg gagggcagtg tagtctgagc | 1620 |
| agtactcgtt gctgccgcgc gcgccaccag acataatagc tgacagacta acagactgtt | 1680 |
| cctttccatg ggtcttttct gcagtcaccg tcctt | 1715 |

<210> SEQ ID NO 8
<211> LENGTH: 1767
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 8

```
atatgaggct atatcgccga tagaggcgac atcaagccgg cacatggcca atgcatatcg      60
atctatacat tgaatcaata ttggcaatta gccatattat tcattggtta tatagcataa     120
atcaatattg gctattggcc attgcatacg ttgtatccgt atcataatat gtacatttat     180
attggcccat gtccaatatg accgccatgt tgacattgat tatttgactag ttattaatag    240
taatcaatta cggggtcatt agttcatagc ccatatatgg agttccgcgt tacataactt     300
acggtaaatg gcccgcctgg ctgaccgccc aacgacccccc gcccattgac gtcaataatg    360
acgtatgttc ccatagtaac gccaataggg actttccatt gacgtcaatg ggtggagtat    420
ttacggtaaa ctgcccactt ggcagtacat caagtgtatc atatgccaag tccgccccct    480
attgacgtca atgacggtaa atggcccgcc tggcattatg cccagtacat gaccttacgg    540
gactttccta cttggcagta catctacgta ttagtcatcg ctattaccat ggtgatgcgg    600
ttttggcagt acatcaatgg gcgtggatag cggtttgact cacggggatt tccaagtctc    660
caccccattg acgtcaatgg gagtttgttt tggcaccaaa atcaacggga ctttccaaaa    720
tgtcgtaata accccgcccc gttgacgcaa atgggcggta ggcgtgtacg gtgggaggtc    780
tatataagca gagctcgttt agtgaaccgt cagatcgcct ggagacgcca tccacgctgt    840
tttgacctcc atagaagaca ccgggaccga tccagcctcc gcggccggga acggtgcatt    900
ggaacgcgga ttccccgtgc caagagtgac gtaagtaccg cctatagact ctataggcac    960
acccctttgg ctcttatgca tgctatactg tttttggctt ggggcctata cacccccgct   1020
tccttatgct ataggtgatg gtatagctta gcctataggc gtgggttatt gaccattatt   1080
gaccactccc ctattggtga cgatactttc cattactaat ccataacatg gctctttgcc   1140
acaactatct ctattggcta tatgccaata ctctgtcctt cagagactga cacggactct   1200
gtatttttac aggatggggt cccatttatt atttacaaat tcacatatac aacaacgccg   1260
tccccgtgc ccgcagtttt tattaaacat agcgtgggat ctccacgcga atctcgggta   1320
cgtgttccgg acatgggctc ttctccggta gcggtgggc ttccacatcc gagccctggt   1380
cccatgcctc cagcgactca tggtcgctcg gcagctcctt gctcccaaca gtggaggcca   1440
gacttaggca cagcacgatg cccaccacca ccagtgtgcc gcacaaggcc gtggcggtag   1500
ggtatgtgtc tgaaaatgag ctcggagatc gggctcgcac cgctgacgca gatggaagac   1560
ttaaggcagc ggcagaagaa gacgcaggca gctgagttgt tgtgttctga taagagtcag   1620
aggtaactcc cgttgcggtg ctgttaacgg tggagggcag tgtagtctga gcagtactcg   1680
ttgctgccgc gcgcgccacc agacataata gctgacagac taacggactg ttcctttcca   1740
tgggtctttt ctgcagtcac cgtccctt                                       1767
```

<210> SEQ ID NO 9
<211> LENGTH: 1689
<212> TYPE: DNA
<213> ORGANISM: Artificial Sequence
<220> FEATURE:
<223> OTHER INFORMATION: Description of Artificial Sequence: Synthetic oligonucleotide

```
<400> SEQUENCE: 9
atatgaggct atatcgccga tataggcgac atcaagctgg cacatggcca atgcatatcg    60
atctatacat tgaatcaata ttggcaatta gccatattag tcattggtta tatagcataa   120
atcaatatcg gctattggcc attgcatacg ttgtatctat atcataatat gtacatttat   180
attggctcat gtccaatacg accgccatgt tgacattgat tattgactag ttattaatag   240
taatcaatta cggggtcatt agttcatagc ccatatatgg agttccgcgt tacataactt   300
acggtaaatg gcccgcctgg ctgaccgccc aacgaccccc gcccattgac gtcaataatg   360
acgtatgttc ccatagtaac gccaataggg actttccatt gacgtcaatg ggtggagtat   420
ttacggtaaa ctgcccactt ggcagtacat caagtgtatc atatgccaag tccgccccct   480
attgacgtca atgacggtaa atggcccgcc tggcattatg cccagtacat ggcttacggg   540
actttcccta cttggcagta catctacgta ttagtcatcg ctattaccat ggtgatgcgg   600
ttttggcagt acaccaatgg gcgtggatag cggtttgact cacggggatt tccaagtctc   660
caccccattg acgtcaatgg gcggtcctat gacgcaaatg ggcggtagg cgtgtacggt    720
gggaggtcta tataagcaga gctcgtttag tgaaccgtca gatcgcctgg agacgccatc   780
cacgctgttt tgacctccat agaagacacc gggaccgatc cagcctccgc ggccgggaac   840
ggtgcattgg aacgcggatt ccccgtgcca gagtgacgt aagtaccgcc tatagactct    900
ataggcacac ccctttggct cttggggcct atacaccccc gcctccttat gctataggtg   960
atggtatagc ttagcctata ggtgtgggtt attgaccatt attgaccact ccctattgg   1020
tgacgatact tttcattact aatccataac atggctcttt gccacaacta tctctattgg  1080
ctatatgcca atacactgtc cttcagagac tgacacggac tctgtatttt tacaggatgg  1140
ggtcccattt attatttaca aattcacata tacaacaacg ccgtcccccg tgcccgcagt  1200
ttttattaaa cataacgtgg gatctccacg cgaatctcgg gtacgtgttc cggacatggg  1260
ctcttctccg gtagcggcgg agcttccaca tccgagccct gctcccatgc ctccagcggc  1320
tcatggtcgc tcggcagctc cttgctccta acagtggagg ccagacttag gcacagcaca  1380
atgcccacca ccaccagtgt gccgcacaag gccgtggcgg tcatggtcgc tcggcagctc  1440
cttgctccta acagtggagg ccagacttag gcacagcaca atgcccacca ccaccagtgt  1500
gccgcacaag gccgtggcgg tgttgtgttc tgataagagt cagaggtaac tcccgttgcg  1560
gtgctgttaa cggtggaggg cagtgtagtc tgagcagtac tcgttgctgc cgcgcgcgcc  1620
accagacata atagctgaca gactaacaga ctgttccttt ccatgggtct tttctgcagt  1680
caccgtctt                                                          1689
```

<210> SEQ ID NO 10
<211> LENGTH: 1715
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 10
atatgaggct atatcgccga tagagacgac atcaagctgg cacatggcca atgcatatcg    60
atctatacat tgaatcaata ttggccatta gccatattat tcattggtta tatagcataa   120
atcaatattg gctattggcc attgcatacg ttgtatctat atcataatat gtacatttat   180
attggttcat gtccaatatg accgccatgc tgacattgat tattgactag ttattaatag   240
```

-continued

```
taatcaatta cggggtcatt agttcatagc ccatatatgg agttccgcgt tacataactt    300
acggtagatg gcccgcctgg ccgaccgccc aacgacccccc gcccattgac gtcaataatg   360
acgtatgtcc ccatagtaac gccaataggg actttccatt gacgtcaatg ggtggagtat   420
ttacggtaaa ctgcccactt ggcagtacat caagtgtatc atatgccaag tacgccccct   480
attgacgtca atgacggtaa atggcccgcc tggcattatg cccagtacat gaccttacgg   540
gactttccta cttggcagta catctacgta ttagtcatcg ctattaccat ggtgatgcgg   600
ttttggcagt acatcaatgg gcgtggatag cggtttgact cacggggatt tccaagtctc   660 cacccccattg acgtcaatgg ggcggtccta tgacgcaaat gggcggtagg cgtgtacggt   720
gggaggtcta taagcagagc tcgtttag tgaaccgtca gatcgcctgg agacgccatc   780
cacgctgttt tgacctccat agaagacacc gggaccgatc cagcctccgc ggccgggaac   840
ggtgcattgg aacgcggatt ccccgtgcca agagtgacgt aagtaccgcc tatagagtct   900
ataggcccac ccccttggct cttatgcatg ctatactgtt tttggcttgg ggcctataca   960 ccccccgcttc cttatgctat aggtgatggt atagcttagc ctataggtgt gggttattga  1020
ccattattga ccactcccct attggtgacg atactttcca ttactaatcc ataacatggc  1080
tctttgccac aactatctct attggctata tgccaatact ctgtccttca gagactgaca  1140
cggactctgt attttacag gatggggtcc catttattat ttacaaattc acatatacaa  1200
caacgccgtc ccccgtgccc gcagtttta ttaaacatag cgtgggatct ccacgcgaat  1260
ctcgggtacg tgttccggac atgggctctt ctccggtagc ggcggagctt ccacatccga  1320
gccctggtcc catgcctcca gcggctcatg gtcgctcggc agctccttgc tcccaacagt  1380
ggaggccaga cttaggcaca gcacaatgcc caccaccacc agtgtgccgc acaaggccgt  1440
ggcggtaggg tatgtgtctg aaaatgagct cggagattgg gctcgcaccg ctgacgcaga  1500
tggaagactt aaggcagcgg cagaagaaga tgcaggcagc tgagttgttg tattctgata  1560
agagtcagag gtaactcccg ttgcggtgct gttaacggtg gagggcagtg tagtctgagc  1620
agtgctcgtt gctgccgcgc gcgccaccag acataatagc tgacagacta acaggctgtt  1680
ccttttcatg ggtcttttct gcagtcaccg tcctt    1715
```

<210> SEQ ID NO 11
<211> LENGTH: 1757
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 11

```
atatgaggct atatcgccga tataggcgac atcaagctgg cacatggcca atgcatatcg    60
atctatacgt tgaatcaata ttggccatta gccatattat tcattggtta tatagcataa   120
atcaatattg gctattggcc attgcatacg ttgtatccat atcataatat gtacatttat   180
attggctcat gtccaatatg accgccatgc tgacattgat tattgactag ttattaacag   240
taatcaatta cggggtcatc agttcatagc ccatatatgg agttccgcgt tacataactt   300
acggtaaatg gcccgcctgg ctgaccgccc aacgacccccc gcccattgac gtcaataatg   360
acgtatgttc ccatagtaac gccaataggg actttccatt gacgtcgatg ggtggagtat   420
ttacggtaaa ctgcccactt ggcagtacat caagtgtatc atatgccaag tccgccccct   480
attgacgtca atgacggtaa atggcccgcc tggcattatg cccagtacat gaccttacgg   540
```

-continued

```
gactttccta cttggcagta catctacgta ttagtcatcg ctgttaccat ggtgatgcgg      600
ttttggcagt acaccaatgg gcgtggatag cggtttgact cacggggatt tccaagtctc      660 cacccccattg acgtcaatgg gagtttgttt tggcaccaaa atcaacggga ctttccaaaa     720
tgtcgtaata accccgcccc gttgacgcaa atgggcggta ggcgtgtacg gtgggaggtc      780
tatataagca gagctcgttt agtgaaccgc cattctgcct ggggacgtcg gaggagcacc      840
atagaaggta ccgggaccga tccagcctcc atagccggga acgtgcatt ggaacgcgga      900 ttccccgtgc aagagtgac gtaggtaccg cctatagact ctataggcac accccttttgg     960 ctcttatgca tgctatactg ttttttggctt ggggcctata caccccgct tccttatgct     1020 ataggtgatg gtatagctta gcctataggt gtgggttatt gaccattatt gaccactccc    1080
ctattggtga cgatactttc cattactaat ccataacatg gctctttgcc acaactatct    1140
ctattggcta tatgccaata ctctgtcctt cagagactga cacggactct gtattttac    1200 aggatggggt ctcatttatt atttacaaat tcacatatac aacaacgccg tcccccgtgc   1260
ccgcagtttt tattaaacat agcgtgggat ctccacgcga atctcgggta cgtgttccgg    1320
acatgggctc ttctccggta gcggcggagc ttccacatcc gagccctggt cccatgcctc    1380
cagcggctca tggtcgctcg gcagccccttt gctcctaaca gtggaggcca gacttaggca    1440
cagcacaatg cccaccacca ccagtgtgcc gcacaaggcc gtggcggtag ggtatgtgtc    1500
tgaaaatgag ctcggagatt gggctcgcac cgctgacgca gatggaagac ttaaggcagc    1560
ggcagaagag gatgcaggca gctgagttgt tgtattctga taagagtcag aggtaactcc    1620
cgttgcggtg ctgttaacgg tggagggcag tgtagtctga gcagtactcg ttgctgccgc    1680
gcgcgccacc aaacataata gctgacagac taacagactg ttcctttcca tgggtctttt    1740
ctgcagtcac cgtcctt                                                    1757
```

<210> SEQ ID NO 12
<211> LENGTH: 1574
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 12

```
atatgaggct atatcgccga tagaggcgac atcaagctgg cacatggcca atgcatatcg       60
atctatacat tgaatcaata ttggcaatta gccatattag tcattggtta tatagcataa      120
atcaatattg gctattggcc attgcatacg ttgtatctat atcataatat gtacatttat      180
attggctcat gtccaacatt accgccatgt tgacattgat tattgactag ttattaatag      240
taatcaatta cggggtcatt agttcatagc ccatatatgg agttccgcgt tacataactt      300
acggtaaatg gcccgcctgg cattatgccc agtacatgac cttacgggac tttcctactt      360
ggcagtacat ctacgtatta gtcatcgcta ttaccatggt gatgcggttt tggcagtaca      420
ccaatgggcg tggatagcgg tttgactcac ggggatttcc aagtctccac cccattgacg      480
tcaatgggag tttgttttgg caccaaaatc aacgggactt ccaaaatgt cgtaataacc       540 ccgcccccgtt gacgcaaatg gcggtaggc gtgtacggtg ggaggtctat ataagcagag      600
ctcgtttagt gaaccgtcag atcgcctgga gacgccatcc acgctgtttt gacctccata      660
gaagacaccg ggaccgatcc agcctccgcg gccgggaacg tgcattgga acgcggatcc      720 cccgtgccaa gagtgacgta agtaccgcct atagactcta taggcacacc cctttggctc      780
```

```
ttatgcatgc tatactgttt ttggcttggg gcctatacac ccccgcttcc ttatgctata        840
ggtgatggta tagcttagcc tataggtgtg ggttattgac cattattgac cactccccta        900
ttggtgacga tactttccat tactaatcca taacatggct ctttgccaca actatctcta        960
ttggctatat gccaatactc tgtccttcag agactgacac ggactctgta tttttacagg       1020
atggggtccc atttattatt tacaaattca catatacaac aacgccgtcc cccgtgcccg       1080
cagtttttat taaacatagc gtgggatctc cacgcgaatc tcgggtacgt gttccggaca       1140
tgggctcttc tccggtagcg gcggagcttc cacatccgag ccctggtccc atgcctccag       1200
cggctcatgg tcgctcggca gctccttgct cctaacagtg gaggccagac ttaggcgcag       1260
cacaatgccc accaccacca gtgtgccgca caaggccgtg gcggtagggt atgtgtctga       1320
aaatgagctc ggagattggg ctcgcaccgc tgacgcagat ggaagactta aggcagcggc       1380
agaagaagat gcaggcagct gagttgttgt attctgataa gagtcagagg taactcccgt       1440
tgcggtgctg ttaacggtgg agggcagtgt agtctgagca gtactcgttg ctgccgcgcg       1500
cgccaccaga cataatagct gacagactaa cagactgttc cttttccatgg gtctttctg       1560 cagtcaccgt cctt                                                         1574

<210> SEQ ID NO 13
<211> LENGTH: 1765
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
atatgaggct atatcgccga tagaggcgac atcaagccgg cacatggcca atgcatatcg         60
atccatacat tgaatcaata ttggccatta gccatattat tcattggtta tatagcataa        120
atcaatattg gctattggcc attgcatacg ttgtatccat atcataatat gtacatttat        180
attggctcat gtccaatatg accgccatgt tgacattgat tattgactag ttattaatag        240
taatcaatta cggggtcatt agttcatagc ccatatatgg agttccgcgt tacataactt        300
acggtagatg gcccgcctgg ctgaccgccc aacgaccccc gcccattgac gtcaataatg        360
acgtatgttc ccatagtaac gccaataggg actttccatt gacgtcaatg ggtggagtat        420
ttacggtaaa ctgcccactt ggcagtacat caagtgtatc atatgccaag tccgccccct        480
attgacgtca atgacggtaa atggcccgcc tggcattatg cccagtacat gaccttacgg        540
gactttccta cttggcagta catctacgta ttagtcatcg ctattaccat ggtgatgcgg        600
ttttggcagt acatcaatgg gcgtagatag cggtttgact cacggggatt tccaagtctc        660
caccccattg acgtcaatgg gagtttgtct tggcaccaaa atcaacggga ctttccaaaa        720
tgtcgtaata accccgcccg ttgacgcaaa tgggcggtag gcgtgtacgg tgggaggtct        780
atataagcag agctcgttta gtgaaccgtc agatcgcctg gagacgccat ccacgctgtt        840
ttgacctcca tagaagacac cgggaccgat ccagcctccg cggccgggaa cggtgcattg        900
gaacgcggat tccccgtgcc aaagtgacgt aagtaccgcc tatagactct ataggcacac        960
ccctttggct cttatgcatg ctatactgtt tttggcttgg ggcctataca ccccgcttc       1020 cttatgctat aggtgatggt atagcttagc ctataggtgt gggttattga ccattattga       1080
ccactcccct attggtgacg atactttcca ttactaatcc ataacatggc tctttgccac       1140
aactatctct attggctata tgccaatact ctgtccttca gagactgaca cggactctgt       1200
```

-continued

```
attttttacag gatggggtcc catttattat ttacaaattc acatatacaa caacgccgtc    1260 cccccgtgccc gcagttttta ttaaacatag cgtgggatct ccacgcgaat ctcgggtacg    1320
tgttccggac atgggctctt ctccggtagc ggcggagctt ccacatccga gccctggtcc    1380
catgcctcca gcggctcatg gtcgctcggc agctccttgc tcctaacagt ggaggccaga    1440
cttaggcgca gcacaatgcc caccaccacc agtgtgccgc acaaggccgt ggcggtaggg    1500
tatgtgtctg aaaatgagct cggagattgg gctcgcaccg ctgacgcaga tggaagactt    1560
aaggcagcgg cagaagaaga tgcaggcagc tgagttgttg tattctgata agagtcagag    1620
gtaactcccg ttgcggtgct gttaacggtg gagggcagtg tagtctgagc agtactcgtt    1680
gctgccgcgc gcgccaccag acataatagc tgacagacta acagactgtt cctttccatg    1740
ggtcttttct gcagtcaccg tcctt                                          1765
```

<210> SEQ ID NO 14
<211> LENGTH: 1767
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 14

```
atatgaggct atatcgccga tataggcgac atcaagctgg cacatggcca atgcatatcg     60
atctatacat tgaatcaata ttggcaatta gccatattag tcattggtta tatagcataa    120
atcaatattg gctattggcc attgcatacg ttgtatctat atcataatat gtacatttat    180
attggctcat gtccaatatg accgccatgt tgacattgat tattgactag ttattaatag    240
taatcaatta cggggtcatt agttcatagc ccatatatgg agttccgcgt tacataactt    300
acggtaaatg gcccgcctgg ctgaccgccc aacgaccccc gcccattgac gtcaataatg    360
acgtatgttc ccatagtaac gccaataggg actttccatt gacgtcaatg ggtggagtat    420
ttacggtaaa ctgcccactt ggcagtacgt caagtgtatc atatgccaag tccgccccct    480
attgacgtca atgacggtaa atggcccgcc tggcattatg cccagtacat gaccttacgg    540
gactttccta cttggcagta catctacgta ttagtcatcg ctattaccat ggtgatgcgg    600
tttaggcagt acaccaatgg gcgtggatag cggtttgact cacggggatt tccaagtctc    660 cacccccattg acgtcaatgg gagtttgttt tggcaccaaa atcaacggga ctttccaaaa    720
tgtcgtaata accccgcccc gttgacgcaa atgggcggta ggcgtgtacg gtgggaggtc    780
tatataagca gagctcgttt agtgaaccgt cagatcgcct ggagacgcca tccacgctgt    840
tttgacctcc atagaagaca ccgggaccga tccagcctcc atagccggga acggtgcatt    900
ggaacgcgga ttccccgtgc caagagtgac gtaagtaccg cctatagact ctataggcac    960 accccctttgg ctcttatgca tgctatactg ttttggctt ggggcctata cacccccgct   1020
tccttatgct ataggtgatg gtatagctta gcctataggt gtgggttatt gaccattatt   1080
gaccactccc ctattggtga cgatactttc cattactaat ccataacatg gctctttgcc   1140
acaactatct ctattggcta tatgccaata ctctgtcctt cagagactga cacggactct   1200 gtattttac aggatgggt cccatttatt atttacaaat tcacatatac aacaacgccg   1260 tcccccagtgc ccgcagtttt tattaaacat agcgtgggat ctccacgcga atctcgggta   1320
cgtgttccgg acatgggctc ttctccggta ggggcggagc ttccacatcc gagccctgct   1380
cccatgcctc cagcggctca tggtcgctcg gcagctcctt gctcctaaca gtggaggcca   1440
```

```
gacttaggca cagcacaatg cccaccacca ccagtgtgcc gcacaaggcc gtggcggtag   1500
ggtatgtgtc tgaaaatgag ctcggagatt gggctcgcac cgctgacgca gatggaagac   1560
ttaaggcagc ggcagaagaa gatgcaggca gctgagttgt tgtattctga taagagtcag   1620
aggtagctcc cgttgcggtg ctgttaacgg tggagggcag tgtagtctga gcagtactcg   1680
ttgctgccgc gcgcgccacc agacataata gctgacagac taacagactg ttccttccca   1740
tgggtctttt ctgcagtcac cgtcctt                                       1767
```

<210> SEQ ID NO 15
<211> LENGTH: 1767
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15

```
atatgaggct atatcgccga tagaggcgac atcaagctgg cacatggcca atgcatatcg     60
atctatacat tgaatcaata ttagcaatta gccatattag tcattggtta tatagcgtaa    120
atcaatattg gctattggcc attgcatacg ttgtatctat atcataatat gtacatttat    180
attggctcat gtccaatatg accgccatgt tgacattgat tattgactag ttattaatag    240
taatcaatta cggggtcatt agttcatagc ccatatatgg agttccgcgt tacataactt    300
acggtaaatg gcccgcctgg ctgaccgccc aacgaccccc gcccattgac gtcaataatg    360
acgtatgttc ccatagtaac gccaataggg actttccatt gacgtcaatg ggtggagtat    420
ttacggtaaa ctgcccactt ggcagtacat caagtgtatc atatgccaag tccgccccct    480
attgacgtca atgacggtaa atggcccgcc tggcattatg cccagtacat gaccttacgg    540
gactttccta cttggcagta catctgcgta ttagtcatcg ctattaccat ggtgatgcgg    600
ttttggcagt acaccaatgg gcgtggatag cggtttgact cacggggatt tccaagtctc    660
caccccattg acgtcaatgg gagtttgttt tggcaccaaa atcaacggga ctttccaaaa    720
tgtcgtaata accccgcccc gttgacgcaa atgggcggta ggcgtgtacg gtgggaggtc    780
tatataagca gagctcgttt agtgaaccgt cagatcgcct ggagacgcca tccacgctgt    840
tttgacctcc atggaagaca ccgggaccga tccagcctcc gcggccggga acggtgcatt    900
ggaacgcgga ttccccgtgc caagagtgac gtaagtaccg cctatagact ctataggcac    960
acccctttgg ctcttatgca tgctatactg tttttggctt ggggcctata cacccccgct   1020
tccttatgct ataggtgatg gtatagctta gcctataggt gtgggttatt gaccattatt   1080
gaccactccc ctattggtga cgatactttc cattactaat ccataacatg gctctttgcc   1140
acaactatct ctattggcta tatgccaata tctctgtcct tcagagactga cacggactct   1200 gtattttttac aggatggggt ctcatttatt atttacaaat tcacatatac aacaacgccg   1260 tccccgtgc ccgcagtttt tattaaacat agcgtgggat ctccacgcga atctcgggta    1320
cgtgttccgg acatgggctc ttctccggta gcggcggagc ttccacatcc gagccctggt   1380
cccatgcctc cagcggctca tggtcgctcg gcagctcctt gctcctaaca gtggaggcca   1440
gacttaggca cagcacaatg cccaccacca ccagtgtgcc gcacaaggcc gtggcggtag   1500
ggtatgtgtc tgaaaatgag ctcggggagc gggcttgcac cgctgacgca gatggaagac   1560
ttaaggcagc ggcagaagaa gatgcaggca gctgagttgt tgtattctga taagagtcag   1620
aggtaactcc cgttgcggtg ctgttaacgg tggagggcaa tgtagtctga gcagtactcg   1680
```

```
ttgctgccgc gcgcgccacc agacataata gctgacagac taacagactg ttcctttcca    1740
tgggtctttt ctgcagtcac cgtcctt                                        1767

<210> SEQ ID NO 16
<211> LENGTH: 1767
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
atatgaggct atatcgccga tataggcgac atcaagctgg cacatggcca atgcatatcg      60
atctatacat tgaatcaata ttggcaatta gccatattag tcattggtta tatagcataa     120
atcaatattg gctattggcc attgcatacg ttgtatctat atcataatat gtacatttat     180
attggctcat gtccaatatg accgccatgt tgacattgat tatttgactag ttattaatag    240 taatcaatta cggggtcatt agttcatagc ccatatatgg agttccgcgt tacataactt     300
acggtagatg gcccgcctgg ctgaccgccc aacgacccc gcccattgac gtcaataatg      360
acgtatgttc ccatagtaac gccaataggg actttccatt gacgtcaatg ggtggagtat     420
ttacggtaaa ctgcccactt ggcagtacat caagtgtatc atatgccaag tccgccccct     480
attgacgtca atgacggtaa atggcccgcc tggcattatg cccagtacat gaccttacgg     540
gactttccta cttggcagta catctacgta ttagtcatcg ctattaccat ggtgatgcgg     600
ttttggcggt acatcaatgg gcgtagatag cggtttgact cacggggatt tccaagtctc     660
caccccattg acgtcaatgg gagtttgttt tggcaccaaa atcaacggga ccttccaaaa     720
tgtcgtaata accccgcccc gttgacgcaa atgggcggta ggcgtgtacg gtgggaggtc     780
tatataagca gagctcgttt agtgaaccgt cagatcgcct ggagacgcca tccacgctgt     840
tttgacctcc atagaagaca ccgggaccga tccagcctcc gcggccggga acggtgcatt     900
ggaacgcgga ttccccgtgc caagagtgac ataagtaccg cctatagact ctataggcac     960 accccttlgg ctcttatgca tgctatactg ttltttggctt ggggcctata caccccgct    1020 tccttatgct ataggtgatg gtatagctta gcctataggt gtgggttatt gaccattatt    1080
gaccactccc ctattggtga cgatactttc cattactaat ccataacatg gctctttgcc    1140
acaactatct ctattggcta tatgccaata ctctgtcctt cagagactga cacggactct    1200
gtatttttac aggatggggt ctcatttatt atttacaaat tcacatatac aacaacgccg    1260 tccccccgtgc ccgcagtttt tattaaacat agcgtgggat ctccacgcaa atctcgggta    1320
cgtgttccgg gcatgggctc ttctccggta gcggcggagc ttccacatcc gagccctggt   1380
cccatgcctc cagcggctca tggtcgctcg gcagctcctt gctcctaaca gtggaggcca    1440
gacttaggca cagcacaatg cccaccacca ccagtgtgcc gcacaaggcc gtggcggtag    1500
ggtatgtgtc tgaaaatgag ctcggagatt gggctcgcac cgctgacgca gatggaagac    1560
ttaaggcagc ggcagaagaa gatgcaggca gctgagttgt tgtattctga taagagtcag    1620
aggtaactcc cgttgcggtg ctgttaacgg cggagggcag tgtagtctga gcagtactcg    1680
ttgctgccgc gcgcgccacc agacataata gctgacagac taacagactg ttcctttcca    1740
tgggtctttt ctgcagtcac cgtcctt                                        1767
```

-continued

<210> SEQ ID NO 17
<211> LENGTH: 1757
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 17

| | | | | | |
|---|---|---|---|---|---|
| atatgaggct | atatcgccga | tagaggcgac | atcaagctgg | cacatggcca | atgcatatcg | 60 |
| atctatacat | tgaatcaata | ttggcaatta | gccatattag | tcattggtta | tatagcataa | 120 |
| atcaatattg | gctattggcc | attgcatacg | ttgtatccat | atcataatat | gcacattat | 180 |
| attggctcat | gtccaatatg | accgccatgt | tgacattgat | tattgactag | ttattaatag | 240 |
| taatcaatta | cggggtcatt | agttcatagc | ccatatatgg | agttccgcgt | tacataactt | 300 |
| acggtaaatg | gcccgcctgg | ctgaccgccc | aacgaccccc | acccattgac | gtcaataatg | 360 |
| acgtatgttc | ccatagtaac | gccaataggg | actttccatt | gacgtcaatg | ggtggagtat | 420 |
| ttacggtaaa | ctgcccactt | ggcagtacat | caagtgtatc | atatgtcaag | tccgcccct | 480 |
| attgacgcca | atgacggtaa | atggcccgcc | tggcattatg | cccagtacat | gaccttacgg | 540 |
| gactttccta | cttggcagta | catctacgta | ttagtcatcg | ctattaccat | ggtgatgcgg | 600 |
| ttttggcagt | acaccaatgg | gcgtggatag | cggtttgact | cacggggatt | tccaagtctc | 660 |
| caccccattg | acgtcaatgg | gagtttgttt | tggcaccaaa | gtcaacggga | ctttccaaaa | 720 |
| tgtcgtaata | accccgcccc | gttgacgcaa | atgggcggta | ggcgtgtacg | gtgggaggtc | 780 |
| tatataagca | gagctcgttt | agggaaccgt | cattctgcct | ggggacgtcg | gaggagcacc | 840 |
| atagaaggta | ccgggaccga | tccagcctcc | gcggccggga | acggtgcatt | ggaacgcgga | 900 |
| ttccccgtgc | caagagtgac | gtaagtaccg | cctatagact | ctataggcac | accccttgg | 960 |
| ctcttatgca | tgctatactg | tttttggctt | ggggcctata | cacccccgct | tcctcatgtt | 1020 |
| ataggtgatg | gtatagctta | gcctataggt | gtgggttatt | gaccattatt | gaccattccc | 1080 |
| ctattggtga | cgatactttc | cattactaat | ccataacatg | gctctttgcc | acaactatct | 1140 |
| ctattggcta | tatgccaata | cactgtcctt | cagaggctga | cacggactct | gtattttac | 1200 |
| aggatgggt | cccatttatt | atttacaaat | tcacatatac | aacaacgccg | tccccgtgc | 1260 |
| ccgcagtctt | tattaaacat | agcgtgggat | ctccacgcga | atctcgggta | cgtgttccgg | 1320 |
| acatgggctc | ttctccggta | gcggcggagc | ttccacatcc | gagccctggt | cccatgcctc | 1380 |
| cagcggctca | tggtcgctcg | gcagctcctt | gctcctaaca | gtggaggcca | gacttaggca | 1440 |
| cagcacaatg | cccaccacca | ccagtgtgcc | gcacaaggcc | gtggcggtag | ggtatgtgtc | 1500 |
| tgaaaatgag | ctcggagatt | gggctcgcac | cgctgacgca | gatggaagac | ttaaggcagc | 1560 |
| ggcagaagaa | gatgcaggca | gctgagttgt | tgtattctga | taagagtcag | aggtaactcc | 1620 |
| cgttgcggtg | ctgttaacgg | tggagggcgg | tgtagtctga | gcagtactcg | ttgctgccgc | 1680 |
| gcgcgccacc | agacataata | gctgacagac | taacagactg | ttcctttcca | tgggtctttt | 1740 |
| ctgcagtcac | cgtccttt | | | | | 1757 |

<210> SEQ ID NO 18
<211> LENGTH: 1767
<212> TYPE: DNA
<213> ORGANISM: Artificial Sequence
<220> FEATURE:
<223> OTHER INFORMATION: Description of Artificial Sequence: Synthetic oligonucleotide -continued

```
<400> SEQUENCE: 18
atatgaggct atatcgccga tataggcgac atcaagctgg cacatggcca atgcatatcg    60
atctatacat tgaatcaata ttggcaatta gccatattag tcattggtta tatagcataa   120
atcaatattg gctattggcc attgcatacg ttgtatctat atcataatat gtacatttat   180
attggctcat gtccaatatg accgccatgt tgacattgat tattgactag ttattaatag   240
taatcaatta cggggttatt agttcatagc ccatatatgg agttccgcgt tacataactt   300
acggtaaatg gcctgcctgg ctgaccgccc aacgaccccc gcccattgac gtcaataatg   360
acgtatgttc ccatagtaac gccaataggg actttccatt gacgtcaatg ggtggagtat   420
ttacggtaaa ctgcccactt ggcagtacat caagtgtatc atatgccaag tacgccccct   480
attgacgtca atgacggtaa atggcccgcc tggcattatg cccagtacat gaccttacgg   540
gactttccta cttggcagta catctacgta ttagtcatcg ctattaccat ggtgatgcgg   600
ttttggcagt acaccaatgg gcgtggatag cggtttgact cacggggatt tccaagtctc   660
caccccattg acgtcaatgg gagtttgttt tggcaccaaa atcaacggga ctttccaaaa   720
tgtcgtaata accccgcccc gttgacgcaa atgggcggta ggcgtgtacg gtgggaggtc   780
tatataagca gagctcgttt agtgaaccgt cagatcgcct ggagacgcca tccacgctgt   840
tttgacctcc atgaagaca ccgggaccga tccagcctcc atagccgggg acggtgcatt   900
ggaacgcgga tcccccgtgc caagagtgac gtaagtaccg cctatagact ctataggcac   960
accccttggg ctcttatgca tgctatactg ttttggcctt ggggcctata cacccccgct  1020
tccttatgct ataggtgatg gtatagctta gcctataggt gtgggttatt gaccattatt  1080
gaccactccc ctattggtga cgatactttc cattactaat ccataacatg gctctttgcc  1140
acaactatct ctattggcta tatgccaata ctctgtcctt cagagactga cacggactct  1200
gtatttttac aggatggggt cccatttatt atttacaaat tcacatatac aacaacgccg  1260
tccccagtgc ccgcagtttt tattaaacat agcgtgggat ctccacgcga atctcgggta  1320
cgtgttccgg acatgggctc ttctccggta gcggcggagc ttccacatcc gagccctggt  1380
cccatgcctc cagcggctca tggtcgctcg gcagctcctt gctcctaaca gtggaggcca  1440
gacttaggca cagcacaatg cccaccacca ccagtgtgcc gcacaaggcc gtggcggtag  1500
ggtatgtgtc tgaaaatgag ctcggagatc gggctcgcac cgctgacgca gatggaagac  1560
ttaaggcagc ggcagaagaa gatgcaggca gctgagttgt tgtattctga taagagtcag  1620
aggtaactcc cgttgcggtg ctgttaacgg tggagggcag tgtagtctga gcagtgctcg  1680
ttgctgccgc gcgcgccacc agacataata gctgacagac taacaggctg ttccttttca  1740
tgggtctttt ctgcagtcac cgtcctt                                      1767

<210> SEQ ID NO 19
<211> LENGTH: 1767
<212> TYPE: DNA
<213> ORGANISM: Homo sapiens

<400> SEQUENCE: 19
atatgaggct atatcgccga tagaggcgac atcaagctgg cacatggcca atgcatatcg    60
atctatacat tgaatcaata ttggccatta gccatattat tcattggtta tatagcataa   120
atcaatattg gctattggcc attgcatacg ttgtatccat atcataatat gtacatttat   180
attggctcat gtccaacatt accgccatgt tgacattgat tattgactag ttattaatag   240
taatcaatta cggggtcatt agttcatagc ccatatatgg agttccgcgt tacataactt   300
```

| | |
|---|---:|
| acggtaaatg gcccgcctgg ctgaccgccc aacgaccccc gcccattgac gtcaataatg | 360 |
| acgtatgttc ccatagtaac gccaataggg actttccatt gacgtcaatg ggtggagtat | 420 |
| ttacggtaaa ctgcccactt ggcagtacat caagtgtatc atatgccaag tacgccccct | 480 |
| attgacgtca atgacggtaa atggcccgcc tggcattatg cccagtacat gaccttatgg | 540 |
| gactttccta cttggcagta catctacgta ttagtcatcg ctattaccat ggtgatgcgg | 600 |
| ttttggcagt acatcaatgg gcgtggatag cggtttgact cacggggatt ccaagtctc | 660 |
| caccccattg acgtcaatgg gagtttgttt tggcaccaaa atcaacggga ctttccaaaa | 720 |
| tgtcgtaaca actccgcccc attgacgcaa atgggcggta ggcgtgtacg gtggaggtct | 780 |
| atataagcag agctcgttta gtgaaccgtc agatcgcctg gagacgccat ccacgctgtt | 840 |
| ttgacctcca tagaagacac cgggaccgat ccagcctccg cggccgggaa cggtgcattg | 900 |
| gaacgcggat tccccgtgcc aagagtgacg taagtaccgc ctatagagtc tataggccca | 960 |
| cccccttggc ttcttatgca tgctatactg ttttttggctt ggggtctata cacccccgct | 1020 |
| tcctcatgtt ataggtgatg gtatagctta gcctataggt gtgggttatt gaccattatt | 1080 |
| gaccactccc ctattggtga cgatactttc cattactaat ccataacatg gctctttgcc | 1140 |
| acaactctct ttattggcta tatgccaata cactgtcctt cagagactga cacggactct | 1200 |
| gtattttac aggatggggt ctcatttatt atttacaaat tcacatgtac aacaccaccg | 1260 |
| tccccagtgc ccgcagtttt tattaaacat aacgtgggat ctccacgcga atctcgggta | 1320 |
| cgtgttccgg acatgggctc ttctccggta gcggcggagc ttctacatcc gagccctgct | 1380 |
| cccatgcctc cagcgactca tggtcgctcg gcagctcctt gctcctaaca gtggaggcca | 1440 |
| gacttaggca cagcacgatg cccaccacca ccagtgtgcc gcacaaggcc gtggcggtag | 1500 |
| ggtatgtgtc tgaaaatgag ctcggggagc gggcttgcac cgctgacgca tttggaagac | 1560 |
| ttaaggcagc ggcagaagaa gatgcaggca gctgagttgt tgtgttctga taagagtcag | 1620 |
| aggtaactcc cgttgcggtg ctgttaacgg tggagggcag tgtagtctga gcagtactcg | 1680 |
| ttgctgccgc gcgcgccacc agacataata gctgacagac taacagactg ttcctttcca | 1740 |
| tgggtctttt ctgcagtcac cgtcctt | 1767 |

<210> SEQ ID NO 20
<211> LENGTH: 1665
<212> TYPE: DNA
<213> ORGANISM: Homo sapiens

<400> SEQUENCE: 20

| | |
|---|---:|
| atatgaggct atatcgccga tagaggcgac atcaagctgg cacatggcca atgcatatcg | 60 |
| atctatacat tgaatcaata ttggcaatta gccatattag tcattggtta tatagcataa | 120 |
| atcaatattg gctattggcc attgcatacg ttgtatctat atcataatat gtacatttat | 180 |
| attggctcat gtccaatatg accgccatgt tgacattgat tattgactag ttattaatag | 240 |
| taatcaatta cggggtcatt agttcatagc ccatatatgg agttccgcgt tacataactt | 300 |
| acggtaaatg gcccgcctcg tgaccgccca acgaccccg cccattgacg tcaataatga | 360 |
| cgtatgttcc catagtaacg ccaataggga ctttccattg acgtcaatgg gtggagtatt | 420 |
| tacggtaaac tgcccacttg gcagtacatc aagtgtatca tatgccaagt ccggcccct | 480 |
| attgacgtca atgacggtaa atggcccgcc tggcattatg cccagtacat gaccttacgg | 540 |
| gactttccta cttggcagta catctacgta ttagtcatcg ctattaccat ggtgatgcgg | 600 |
| ttttggcagt acaccaatgg gcgtggatag cggtttgact cacggggatt ccaagtctc | 660 |

```
caccccattg acgtcaatgg gagtttgttt tggcaccaaa atcaacggga ctttccaaaa      720
tgtcgtaata accccgcccc gttgacgcaa atgggcggta ggcgtgtacg gtgggaggtc      780
tatataagca gagctcgttt agtgaaccgt cagatcgcct ggagacgcca tccacgctgt      840
tttgacctcc atagaagaca ccgggaccga tccagcctcc gcggccggga acggtgcatt      900
ggaacgcgga ttccccgtgc caagagtgac gtaagtaccg cctatagact ctataggcac      960
accccttggg ctcttatgca tgctatactg tttttggctt ggggcctata cacccccgct     1020
ccttatgcta taggtgatgg tatagcttag cctataggtg tgggttattg accattattg     1080
accactcccc tattggtgac gatactttcc attactaatc cataacatgg ctctttgcca     1140
caactatctc tattggctat atgccaatac tctgtccttc agagactgac acggactctg     1200 tattttaca ggatggggtc ccatttatta tttacaaatt cacatataca acaacgccgt      1260
cccccgtgcc cgcagttttt attaaacata gcgtgggatc tccacgcgaa tctcgggtac     1320
gtgttccgga catgggctct ctccggtag cggcggagct tccacatccg agccctggtc      1380
ccatgcctcc agcggctcat ggtcgctcgg cagctccttg ctcctaacag tggaggccag     1440
acttaggcac agcacaatgc ccaccaccac cagtgtgccg cacaaggccg tggcggtagg     1500
gtatgtgtct gaaaatgagc tcggagattg ggctcgcacc gtgacgcaga tggaagactt     1560
aaggcagcgg cagaagaaga tgcaggcagc tgagtaccag acataatagc tgacagacta     1620
acagactgtt cctttccatg ggtcttttct gcagtcaccg tcctt                     1665

<210> SEQ ID NO 21
<211> LENGTH: 1767
<212> TYPE: DNA
<213> ORGANISM: Artificial Sequence
<220> FEATURE:
<223> OTHER INFORMATION: Description of Artificial Sequence: Consensus
      sequence

<400> SEQUENCE: 21
atatgaggct atatcgccga tagaggcgac atcaagctgg cacatggcca atgcatatcg       60
atctatacat tgaatcaata ttggcaatta gccatattag tcattggtta tatagcataa      120
atcaatattg gctattggcc attgcatacg ttgtatctat atcataatat gtacatttat      180
attggctcat gtccaatatg accgccatgt tgacattgat tattgactag ttattaatag      240
taatcaatta cggggtcatt agttcatagc ccatatatgg agttccgcgt tacataactt      300
acggtaaatg gcccgcctgg ctgaccgccc aacgacccccc gcccattgac gtcaataatg      360
acgtatgttc ccatagtaac gccaataggg actttccatt gacgtcaatg ggtggagtat      420
ttacggtaaa ctgcccactt ggcagtacat caagtgtatc atatgccaag tccgcccccct      480 attgacgtca atgacggtaa atggcccgcc tggcattatg cccagtacat gaccttacgg      540
gactttccta cttggcagta catctacgta ttagtcatcg ctattaccat ggtgatgcgg      600
ttttggcagt acaccaatgg gcgtggatag cggtttgact cacggggatt ccaagtctc      660 caccccattg acgtcaatgg gagtttgttt tggcaccaaa atcaacggga ctttccaaaa      720
tgtcgtaata accccgcccc gttgacgcaa atgggcggta ggcgtgtacg gtgggaggtc      780
tatataagca gagctcgttt agtgaaccgt cagatcgcct ggagacgcca tccacgctgt      840
tttgacctcc atagaagaca ccgggaccga tccagcctcc gcggccggga acggtgcatt      900
ggaacgcgga ttccccgtgc caagagtgac gtaagtaccg cctatagact ctataggcac      960
accccttggg ctcttatgca tgctatactg tttttggctt ggggcctata cacccccgct     1020
```

```
tccttatgct ataggtgatg gtatagctta gcctataggt gtgggttatt gaccattatt      1080
gaccactccc ctattggtga cgatactttc cattactaat ccataacatg gctctttgcc      1140
acaactatct ctattggcta tatgccaata ctctgtcctt cagagactga cacggactct      1200 gtattttac aggatgggt cccatttatt atttacaaat tcacatatac aacaacgccg        1260
tcccccgtgc ccgcagtttt tattaaacat agcgtgggat ctccacgcga atctcgggta     1320
cgtgttccgg acatgggctc ttctccggta gcggcggagc ttccacatcc gagccctggt     1380
cccatgcctc cagcggctca tggtcgctcg gcagctcctt gctcctaaca gtggaggcca    1440
gacttaggca cagcacaatg cccaccacca ccagtgtgcc gcacaaggcc gtggcggtag    1500
ggtatgtgtc tgaaaatgag ctcggagatt gggctcgcac cgctgacgca gatggaagac   1560
ttaaggcagc ggcagaagaa gatgcaggca gctgagttgt tgtattctga taagagtcag    1620
aggtaactcc cgttgcggtg ctgttaacgg tggagggcag tgtagtctga gcagtactcg    1680
ttgctgccgc gcgcgccacc agacataata gctgacagac taacagactg ttcctttcca   1740 tgggtcttttt ctgcagtcac cgtcctt                                        1767

<210> SEQ ID NO 22
<211> LENGTH: 821
<212> TYPE: DNA
<213> ORGANISM: Macaca sp.

<400> SEQUENCE: 22
acttggcacg gtgccaagtt tggggcgggg tcttggcacc gtgccaagtc cgccatattg       60
gtttggcata tgtccaatat tattgatcca tatagccaat atccaatatg gctaatagcc      120
aggttcaata gaatggccaa taagccaata tgccattggc caacatggca atgggccagt      180
attgattata gccaatatat aggcaataat ccatattggc atatgtccat attgcctata      240
gccatattgg cttatgtcca ttaccaatac catatatggg tcttcctata tacgtcatag     300
gtaccgccca ttgacgtaat atggatacgc ctccattgac gtcaatggga gggattaata    360
tacgtcacta ataccgccca ttgacgtgta taggaccgtc ccattgacgt caataggccc     420
acctcccatt gacgtcaatg gggtggccca ttgcccattc ccacgccccc tattgacgtc     480
aatgacggta aatggcccac ttggcagtac atcaatacct attaatagta acttggcaag    540
taaatgggta cttggcagta caccaaggta cattggcagt actcccattg acgtcaatgg    600
cggtaaatgg cccgcaatgg ctgccaagta catgcccatt gacgtcaatg ggcggtcct    660 atgacgtcaa tgggcggtag gcgtgcctat gggcggtcta tataagcaat gcacgtttag   720
ggaaccgcca ttctgcctgg ggacgtcgga ggagcaccat agaaggtacc ggggaccgat   780
ccagcctcca tagccgggaa gggtgcattg gaacgcggat a                         821

<210> SEQ ID NO 23
<211> LENGTH: 738
<212> TYPE: DNA
<213> ORGANISM: Cercopithecus sp.

<400> SEQUENCE: 23
attgaattgg catggtgcca ataatggcgg ccatattggc tatatgccag gatcaatata       60
taggcaatat ccaatatggc cctatgccaa tatggctatt ggccaggttc aatactatgt     120
attggcccta tgccatatag tattccatat atgggttttc ctattgacgt agatagcccc     180
tcccaatggg cggtcccata taccatatat ggggcttcct aataccgccc atagccactc     240
ccccattgac gtcaatggtc tctatatatg gtctttccta ttgacgtcat atgggcggtc    300
```

```
ctattgacgt atatggcgcc tcccccattg acgtcaatta cggtaaatgg cccgcctggc    360
tcaatgccca ttgacgtcaa taggaccacc caccattgac gtcaatggga tggctcattg    420
cccattcata tccgttctca cgcccccctat tgacgtcaat gacggtaaat ggcccacttg   480
gcagtacatc aatatctatt aatagtaact tggcaagtac attactattg gcaagtacgc    540
caagggtaca ttggcaggta ctcccattga cgtcaatggc ggtaaatggc ccggcatggc    600
tgccaagtac aacatcccca ttgacgtcaa tgggaagggg caatgacgca aatgggcgtt    660
ccattgacgt aaatggcggt aggcgtgcct aatgggaggt ctatataagc aatgctcgtt    720
tagggaaccg ccattctg                                                  738
```

<210> SEQ ID NO 24
<211> LENGTH: 46
<212> TYPE: DNA
<213> ORGANISM: Artificial Sequence
<220> FEATURE:
<223> OTHER INFORMATION: Description of Artificial Sequence: Primer

<400> SEQUENCE: 24

```
atagcactga gacctatcga attcatatga ggctatatcg ccgata           46
```

<210> SEQ ID NO 25
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 25

```
tcagtgaacg cttatctagg atccaaggac ggtgactgca gaaaa            45
```

<210> SEQ ID NO 26
<211> LENGTH: 50
<212> TYPE: DNA
<213> ORGANISM: Artificial Sequence
<220> FEATURE:
<223> OTHER INFORMATION: Description of Artificial Sequence: Primer

<400> SEQUENCE: 26

```
atagcactga gacctatcga attcaatggc gacttggcat tgagccaatt       50
```

<210> SEQ ID NO 27
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 27

```
atagcactga gacctatcga attcacttgg cacggtgcca agttt            45
```

<210> SEQ ID NO 28
<211> LENGTH: 47
<212> TYPE: DNA
<213> ORGANISM: Artificial Sequence
<220> FEATURE:
<223> OTHER INFORMATION: Description of Artificial Sequence: Primer

<400> SEQUENCE: 28

```
tcagtgaacg cttatctagg atcctatccg cgttccaatg cacccctt         47
```

<210> SEQ ID NO 29
<211> LENGTH: 46
<212> TYPE: DNA
<213> ORGANISM: Artificial Sequence
<220> FEATURE:
<223> OTHER INFORMATION: Description of Artificial Sequence: Primer

<400> SEQUENCE: 29
tcagtgaacg cttatctagg atcctatccg cattccaatg caccgt        46

<210> SEQ ID NO 30
<211> LENGTH: 47
<212> TYPE: DNA
<213> ORGANISM: Artificial Sequence
<220> FEATURE:
<223> OTHER INFORMATION: Description of Artificial Sequence: Primer

<400> SEQUENCE: 30
atagcactga gacctatcac cggttggtcc tgtagtttgc taacaca       47

<210> SEQ ID NO 31
<211> LENGTH: 48
<212> TYPE: DNA
<213> ORGANISM: Artificial Sequence
<220> FEATURE:
<223> OTHER INFORMATION: Description of Artificial Sequence: Primer

<400> SEQUENCE: 31
tcagtgaacg cttatctaac cggttcgagg cagcttggat ctgtaacg      48

<210> SEQ ID NO 32
<211> LENGTH: 53
<212> TYPE: DNA
<213> ORGANISM: Artificial Sequence
<220> FEATURE:
<223> OTHER INFORMATION: Description of Artificial Sequence: Primer

<400> SEQUENCE: 32
attctaccat gtctcaccgg tcgccaccat ggccttacca gtgaccgcct tgc    53

<210> SEQ ID NO 33
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 33
tcactaccta gtagttgtac agtatcttat catgtctgga tca            43

<210> SEQ ID NO 34
<211> LENGTH: 47
<212> TYPE: DNA
<213> ORGANISM: Artificial Sequence
<220> FEATURE:
<223> OTHER INFORMATION: Description of Artificial Sequence: Primer

<400> SEQUENCE: 34
tgagtgaacg cttatctaag cgctttctgt ggaatgtgtg tcagtta        47

<210> SEQ ID NO 35
<211> LENGTH: 47
<212> TYPE: DNA
<213> ORGANISM: Artificial Sequence
<220> FEATURE:
<223> OTHER INFORMATION: Description of Artificial Sequence: Primer -continued

```
<400> SEQUENCE: 35
atagcactga gacctatcct cgagtacgcc ttaagataca ttgatga                    47

<210> SEQ ID NO 36
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 36
aagctggcta gcatgtcgtt tactttgacc aac                                   33

<210> SEQ ID NO 37
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 37
aaacgggccc ttatttttga caccagacca ac                                    32

<210> SEQ ID NO 38
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gacgccggag g                                                           11

<210> SEQ ID NO 39
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
gacgtcggag                                                             10

<210> SEQ ID NO 40
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
aatgggcggt c                                                           11
```

CHIMERIC PROMOTERS

CROSS-REFERENCE TO RELATED APPLICATION

This application claims priority to and benefit of U.S. Provisional Patent Application Ser. No. 60/213,829, filed on Jun. 23, 2000, the full disclosure of which is incorporated herein by reference in its entirety for all purposes.

STATEMENT REGARDING FEDERALLY SPONSORED RESEARCH

This invention was made in part with government support under a grant awarded by the Defense Advanced Research Projects Agency (DARPA) (Grant No. N65236-98-1-5401). The Government may have certain rights in the invention.

COPYRIGHT NOTIFICATION

Pursuant to 37 C.F.R. 1.71(e), Applicants note that a portion of this disclosure contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

FIELD OF THE INVENTION

This invention pertains to the field of transcriptional promoters and enhancers for use in expressing genes in cells.

BACKGROUND OF THE INVENTION

A key to many aspects of genetic engineering is the ability to obtain a sufficient level of expression of a gene of interest. The use of genetic engineering to produce proteins of commercial importance, such as erythropoietin, tissue plasminogen activator, and many others, is well established. However, the cost of producing such products could be decreased by the ability to express a gene that encodes the protein at a higher level. Gene therapy, which involves the introduction of a nucleic acid into cells of a patient to express the nucleic acid for some therapeutic purpose, also depends upon obtaining a sufficient level of expression to achieve the desired result. In other applications, delivery of genes encoding a toxin (e.g., diphtheria toxin, ricin, tk) can be used to kill cancer cells, and other genes can be specifically tailored to kill infectious organisms. Again, obtaining an optimized or sufficient level of expression is a key to success. Genetic vaccines, which express proteins that can induce and/or modulate an immune response, also require adequate levels of gene expression.

Therefore, a need exists for promoters and enhancers that can provide appropriate levels of gene expression (e.g., great, intermediate, or low gene expression levels), as needed for the particular application or purpose, in target cells of interest. The present invention fulfills this and other needs.

SUMMARY OF THE INVENTION

The invention provides novel chimeric or recombinant promoter/enhancers for use in expressing genes in mammalian and other cells. The promoters were obtained by performing DNA shuffling on several isolates of the cytomegalovirus (CMV) immediate early (IE) promoter. The resulting chimeric promoter/enhancers were subjected to screening to identify those that exhibit improved expression, in vitro, as well as in mammals in vivo.

Accordingly, one aspect of the invention is an isolated or recombinant nucleic acid comprising a polynucleotide sequence selected from:

(a) a polynucleotide sequence selected from SEQ ID NO:1 to SEQ ID NO:18 or a complementary polynucleotide sequence thereof;

(b) a polynucleotide sequence that has at least about 97% sequence identity to at least one sequence selected from SEQ ID NO:1 to SEQ ID NO:18 or a complementary polynucleotide sequence thereof;

(c) a polynucleotide sequence that has at least about 80% sequence identity to at least one sequence from the group consisting of SEQ ID NO:1 to SEQ ID NO:18, or a complementary polynucleotide sequence thereof, wherein the polynucleotide sequence promotes expression of an operably linked transgene at a level that is greater than the level of expression of the same transgene when operably linked to a human CMV promoter polynucleotide sequence; and (d) a polynucleotide sequence comprising a fragment of (a), (b), or (c), wherein the fragment promotes expression of an operably linked transgene at a level that is greater than the level of expression of the same transgene when operably linked to a human CMV promoter polynucleotide sequence. The invention also includes an isolated or recombinant nucleic acid comprising a polynucleotide sequence that hybridizes under highly stringent conditions over substantially the entire length of a polynucleotide sequence of claim 1 (a), (b), (c), or (d).

In another embodiment, the invention provides a polynucleotide sequence comprising a fragment of (a), (b), or (c), wherein the fragment promotes expression of an operably linked transgene at a level that is greater than the level of expression of the same transgene when operably linked to a human CMV promoter polynucleotide sequence.

The invention also provides an isolated or recombinant nucleic acid comprising a fragment of one sequence selected from SEQ ID NO:1 to SEQ ID NO:18 or a fragment of a complementary polynucleotide sequence thereof, wherein the fragment comprises a unique subsequence.

Another aspect of the invention is a composition produced by the cleaving of on or more nucleic acids of the invention, wherein the cleaving comprises mechanical, chemical, or enzymatic cleavage. Also included in the invention is a composition produced by a incubating one or more nucleic acids of the invention in the presence of deoxyribonucleotide triphosphates and a nucleic acid polymerase.

Other aspects of the invention relate to a method of producing a modified or recombinant nucleic acid comprising mutating or recombining a nucleic acid of the invention. Accordingly, the invention also includes a nucleic acid library produced by this method, and a nucleic acid library comprising two or more nucleic acids of the invention.

In addition, the invention provides a vector comprising at least one nucleic acid of the invention, a cell comprising a nucleic acid or vector of the invention, and a population of cells comprising a library of the invention.

In another aspect, the invention includes composition comprising a nucleic acid or vector of the invention and a carrier. In a preferred variation of this embodiment, the nucleic acid or vector is present in the composition in an amount sufficient to introduce the nucleic acid or vector into cells of a subject, when the composition is administered to the subject.

The invention also provides a method of producing a polypeptide, which entails:

(a) providing a population of cells comprising a nucleic acid of the invention operably linked to a transgene encoding a polypeptide; and (b) expressing the polypeptide in at least the subset of the population of cells or progeny thereof.

The method can, optionally, comprise isolating the polypeptide from the cells. In a variation of this embodiment, the method includes introducing the nucleic acid operably linked to the transgene into the population of cells. The cells can be in culture or in vivo in a subject. For in vivo applications, the nucleic acid can be introduced into cells in culture, and the cells can subsequently be introduced into the subject. Alternatively, the nucleic acid can be introduced into the cells of the subject by administering the nucleic acid directly to the subject. In preferred in embodiments, where the polypeptide is expressed in vivo, the polypeptide is expressed in an amount sufficient to produce a desired effect in the subject, such as an immunogenic effect, a prophylactic effect, or a therapeutic effect. Accordingly, the invention also includes a nucleic acid of the invention for use in producing an immunogenic effect, a prophylactic effect, or a therapeutic effect in a subject.

In other aspects, the invention provides a kit comprising a nucleic acid or vector of the invention.

The invention also encompasses computer-related uses of the nucleotide sequences of the invention. Thus, the invention provides a database comprising one or more character strings corresponding to a polynucleotide sequence selected from SEQ ID NO:1 to SEQ ID NO:18 or a complementary polynucleotide sequence thereof and a database comprising one or more character strings corresponding to a unique subsequence of a polynucleotide sequence selected from SEQ ID NO:1 to SEQ ID NO:18 or a unique subsequence of a complementary polynucleotide sequence thereof.

The invention also provides a method for manipulating a sequence record in a computer system, the method comprising:

(a) reading a character string corresponding to a polynucleotide sequence selected from SEQ ID NO:1 to SEQ ID NO:18, or a complementary polynucleotide sequence thereof;

(b) performing an operation on the character string; and (c) returning a result of the operation.

In another embodiment, the invention provides method for manipulating a sequence record in a computer system, the method comprising:

(a) reading a character string corresponding to a unique subsequence of a polynucleotide sequence selected from SEQ ID NO:1 to SEQ ID NO:18 or a unique subsequence of a complementary polynucleotide sequence thereof;

(b) performing an operation on the character string; and (c) returning a result of the operation.

BRIEF DESCRIPTION OF THE DRAWINGS

FIGS. 10A–10E shows an alignment of the polynucleotide sequences of WT of the promoter/enhancer regions of the WT Rhesus monkey (SEQ ID NO: 22), Vervet monkey (SEQ ID NO:23), and human Towne (SEQ ID NO:20) CMV isolates.

DETAILED DESCRIPTION

Definitions

Figure 1:
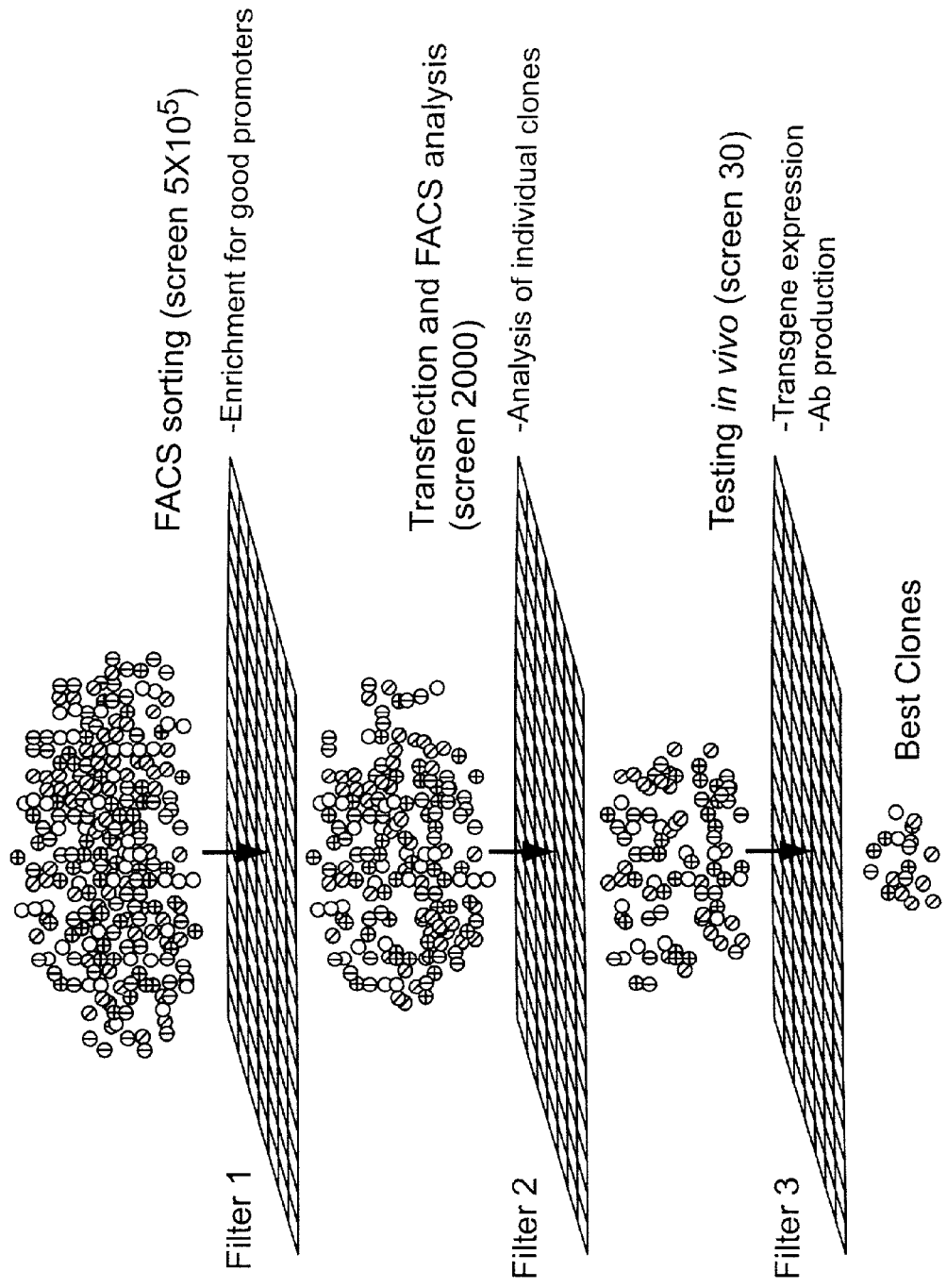
FIG. 1 shows a protocol for screening libraries of chimeric promoter sequences that were produced by shuffling of CMV promoter sequences ("promoters"). A three-tiered approach to screening such shuffled chimeric promoter libraries was applied; first, the library was enriched for good promoter sequences by FACS (Fluorescence-Activated Cell Sorting) sorting. The best sequences were then identified by high throughput transfection and FACS analysis of individual clones. These were subcloned in DNA vaccine vectors encoding luciferase or β-galactosidase to test transgene expression and induction of antibody (Ab) responses in vivo.

The term "gene" broadly refers to any segment of DNA associated with a biological function. Genes include coding sequences and/or regulatory sequences required for their expression. Genes also include non-expressed DNA nucleic acid segments that, e.g., form recognition sequences for other proteins (e.g., promoter, enhancer, or other regulatory regions). Genes can be obtained from a variety of sources, including cloning from a source of interest or synthesizing from known or predicted sequence information, and may include sequences designed to have desired parameters.

A "promoter," as used herein, is a DNA regulatory region that is capable of binding RNA polymerase in a cell (or in vitro transcription system) and initiating transcription of a downstream (3' direction) coding sequence. Often, a promoter is associated with one or more "enhancers" which can provide further regulation of transcription. Enhancers can also be found upstream of the promoter, as well as downstream. A promoter is sometimes bounded at its 3' terminus by the transcription initiation site, but often the promoter/enhancer region includes additional sequences that affect transcription and are found downstream of the transcription initiation site. A promoter extends upstream (5' direction) from the transcription initiation site to include the minimum number of bases or elements necessary to initiate transcription at levels detectable above background. The entire promoter/enhancer region can extend farther upstream to include additional sequences that affect gene expression. Within the promoter/enhancer sequences will be found a transcription initiation site (conveniently defined for example, by mapping with nuclease S1), as well as protein binding domains (consensus sequences) responsible for the binding of RNA polymerase, transcription factors, and other molecules that are involved in transcription. Eukaryotic class II promoters will often, but not always, contain "TATA" boxes and "CAAT" boxes. The human cytomegalovirus (hCMV) immediate early promoter/enhancer (the "CMV promoter," as used herein), for example, also includes, for example, repeat elements of 19, 18 and 21 base pairs (bp) that include binding sites for CREB/ATF, NF-•B/rel, SP-1 and YY-1 binding sites, respectively (Stinski, MF (1999), in *Gene Expression Systems: Using Nature for the Art of Expression*, Academic Press, pp. 211–233).

A "chimeric promoter/enhancer" is a non-naturally occurring promoter/enhancer that includes nucleotides from more than one source nucleic acid. The source nucleic acids can be naturally occurring nucleic acids (e.g., nucleic acids from different isolates or species used in family shuffling), but also can be non-naturally occurring nucleic acids. Those of skill in the art will appreciate that the phrase "nucleotides from more than one source nucleic acid" describes the identity of a particular residue at a particular position in a chimeric nucleic acid or the sequence of nucleotides in a particular region of the chimeric nucleic acid. Thus, two polynucleotide sequences in a chimeric nucleic acid are said to be from different source nucleic acids if the polynucleotide sequences are each identical to a polynucleotide sequence in one of the source nucleic acids. This language does not imply that the chimeric nucleic acid was necessarily formed by joining polynucleotide sequences obtained directly from the source nucleic acids, although the invention encompasses chimeric nucleic acids formed in this manner. As used herein, the term "promoter/enhancer" can refer to either a promoter sequence, as defined above, or an enhancer sequence, or a polynucleotide sequence including both types of sequences.

"Nucleic acid derived from a gene" refers to a nucleic acid for whose synthesis the gene, or a subsequence thereof, has ultimately served as a template. Thus, an mRNA, a cDNA reverse transcribed from an MRNA, an RNA transcribed from that cDNA, a DNA amplified from the cDNA, an RNA transcribed from the amplified DNA, etc., are all derived from the gene and detection of such derived products is indicative of the presence and/or abundance of the original gene and/or gene transcript in a sample.

The term "nucleic acid" refers to deoxyribonucleotides or ribonucleotides and polymers thereof in either single- or double-stranded form. Unless specifically limited, the term encompasses nucleic acids containing known analogues of natural nucleotides which have similar function and are metabolized in a manner similar to naturally occurring nucleotides. The term "nucleic acid" is used interchangeably with the term "polynucleotide" and encompasses genes, cDNA, and MRNA encoded by a gene.

The term "polynucleotide sequence" is a nucleic acid which comprises a polymer of nucleic acid residues or nucleotides (A,C,T,U,G, etc. or naturally occurring or artificial nucleotide analogues), or a character string representing a nucleic acid, depending on context. Either the given nucleic acid or the complementary nucleic acid can be determined from any specified polynucleotide sequence.

As used herein, the term "complementary" refers to the capacity for precise pairing between two nucleotides. Thus, if a nucleotide at a given position of a nucleic acid molecule is capable of hydrogen bonding with a nucleotide of another nucleic acid molecule, then the two nucleic acid molecules are considered to be complementary to one another at that position. The term "substantially complementary" describes sequences that are sufficiently complementary to one another to allow for specific hybridization under stringent hybridization conditions. The term "perfectly complementary" refers to sequences in which there are no mismatched nucleotides (i.e., each nucleotide in both sequences can hydrogen bond with a complementary nucleotide in the other sequence). One such sequence is said to be the "perfect complement" of the other.

Nucleic acids according to the subject invention need not be identical, but can be substantially identical (or substantially similar), to the corresponding sequences of the exemplary chimeric promoter/enhancers described herein. In particular, these nucleic acids can be modified in a number of ways, including mutation or recombination, using standard techniques. A variety of diversity generating protocols are available and described in the art. The procedures can be used separately, and/or in combination to produce one or more variants of a nucleic acid or set of nucleic acids, as well variants of encoded proteins. Individually and collectively, these procedures provide robust, widely applicable ways of generating diversified nucleic acids and sets of nucleic acids (including, e.g., nucleic acid libraries) useful, e.g., for the engineering or rapid evolution of nucleic acids, proteins, pathways, cells and/or organisms with new and/or improved characteristics.

A "library" of nucleic acids includes at least 2 different nucleic acids, and preferably at least about 5, 10, 50, $10^2$, $10^3$, $10^4$, $10^5$, $10^6$, $10^7$ or more different nucleic acids.

Variants of the exemplary nucleic acids described herein generally comprise a sequence substantially similar or substantially identical (as defined below) to at least one of SEQ ID NOS:1–18 or a complementary polynucleotide sequence or fragment thereof.

The term "sequence identity" means that two polynucleotide sequences are identical (i.e., on a nucleotide-by-nucleotide basis) over a window of comparison. The term "percentage of sequence identity" or "percentage of sequence similarity" is calculated by comparing two optimally aligned sequences over the window of comparison, determining the number of positions at which the identical residues occur in both nucleotide sequences to yield the number of matched positions, dividing the number of matched positions by the total number of positions in the window of comparison (i.e., the window size), and multiplying the result by 100 to yield the percentage of sequence identity (or percentage of sequence similarity).

As applied in the context of two nucleic acids, the term substantial identity or substantial similarity means that the two nucleic acid sequences, when optimally aligned, such as by the programs BLAST, GAP or BESTFIT using default gap weights (described in detail below) or by visual inspection, share at least about 70 percent, 75 percent, 80 percent, 85 percent or 88 percent sequence identity or sequence similarity, preferably at least about 90 percent, 91 percent, 92 percent, 93 percent or 94 percent sequence identity or sequence similarity, more preferably at least about 95 percent sequence identity or sequence similarity, or more (including, e.g., about 96, 97, 98, 98.5, 99, 99.5 or more percent nucleotide sequence identity or sequence similarity). Preferably, the substantial identity exists over a region of the sequences that is at least about 50 residues in length, more preferably over a region of at least about 100 residues, and most preferably the sequences are substantially identical over at least about 150 residues or more.

In one aspect, the present invention provides chimeric CMV promoter/enhancer homologue nucleic acids having at least about 70, 75, 80, 85, 88, 90, 91, 92, 93, 94, 95, 96, 97, 98, 98.5, 99, 99.5, or more percent sequence identity or sequence similarity with the nucleic acid sequences of any of SEQ ID NOS:1–18 or complementary polynucleotide sequences or fragments thereof.

A preferred example of an algorithm that is suitable for determining percent sequence identity or sequence similarity is the FASTA algorithm, which is described in Pearson, W. R. & Lipman, D. J., (1988) Proc Natl Acad Sci USA 85:2444. See also, W. R. Pearson, (1996) Methods Enzymology 266:227–258. Preferred parameters used in a FASTA alignment of DNA sequences to calculate percent identity or percent similarity are optimized, BL50 Matrix 15: −5, k-tuple=2; joining penalty=40, optimization=28; gap penalty −12, gap length penalty=−2; and width=16.

Other preferred examples of algorithms that are suitable for determining percent sequence identity or sequence similarity are the BLAST and BLAST 2.0 algorithms, which are described in Altschul et al., (1977) Nuc Acids Res 25:3389–3402 and Altschul et al., (1990) J Mol Biol 215: 403–410, respectively. BLAST and BLAST 2.0 are used, with the parameters described herein, to determine percent sequence identity or percent sequence similarity for the nucleic acids of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see, Henikoff & Henikoff, (1989) Proc Natl Acad Sci USA 89:10915) uses alignments (B) of 50, expectation (E) of 10, M=5, N=−4, and a comparison of both strands. Again, as with other suitable algorithms, the stringency of comparison can be increased until the program identifies only sequences that are more closely related to those in the sequence listings herein (i.e., SEQ ID NOS:1–18, rather than sequences that are more closely related to other similar sequences such as, e.g., those nucleic acid sequences represented by GENSEQ reference numbers: N91042, T77193, Q43524, Q53550, N60156, and Q43525; by GenBank accession nos.: K03104.1,×03922.1, NC_001347.1, and X17403.1; or by other similar molecules found in any public database. (The GenBank accession nos. for the first four GENSEQ sequences are: A01321, AR094363, AR050546, and AR050544.) In other words, the stringency of comparison of the algorithms can be increased so that all known sequences are excluded.

The BLAST algorithm also performs a statistical analysis of the similarity or identity between two sequences (see, e.g., Karlin & Altschul, (1993) Proc Natl Acad Sci USA 90:5873–5787). One measure of similarity or identity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Another example of a useful algorithm is PILEUP. PILEUP creates a multiple sequence alignment from a group of related sequences using progressive, pairwise alignments to show relationship and percent sequence identity or percent sequence similarity. It also plots a tree or dendogram showing the clustering relationships used to create the alignment. PILEUP uses a simplification of the progressive alignment method of Feng & Doolittle, (1987) J Mol Evol 35:351–360. The method used is similar to the method described by Higgins & Sharp, (1989) CABIOS 5:151–153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity (or percent sequence similarity) relationship using the following parameters: default gap weight (3.00), default gap length weight (0.10), and weighted end gaps. PILEUP can be obtained from the GCG sequence analysis software package, e.g., version 7.0 (Devereaux et al., (1984) Nuc Acids Res 12:387–395).

Another preferred example of an algorithm that is suitable for multiple DNA and amino acid sequence alignments is the CLUSTALW program (Thompson, J. D. et al., (1994) Nuc Acids Res 22:4673–4680). CLUSTALW performs multiple pairwise comparisons between groups of sequences and assembles them into a multiple alignment based on homology. Gap open and Gap extension penalties were 10 and 0.05 respectively. For amino acid alignments, the BLOSUM algorithm can be used as a protein weight matrix (Henikoff and Henikoff, (1992) Proc Natl Acad Sci USA 89:10915–10919).

It will be understood by one of ordinary skill in the art, that the above discussion of search and alignment algorithms also applies to identification and evaluation of polynucleotide sequences, with the substitution of query sequences comprising nucleotide sequences, and where appropriate, selection of nucleic acid databases.

Numbering of a given amino acid polymer or nucleotide polymer "corresponds to numbering" of a selected amino acid polymer or nucleic acid polymer when the position of any given polymer component (e.g., amino acid residue, nucleotide residue) is designated by reference to the same or an equivalent residue position in the selected amino acid or nucleotide polymer, rather than by the actual position of the component in the given polymer. Thus, for example, the numbering of a given amino acid position in a given polypeptide sequence corresponds to the same or equivalent amino acid position in a selected polypeptide sequence used as a reference sequence.

Another indication that two nucleic acid sequences are substantially identical is that the two molecules hybridize to each other under stringent conditions. The phrase "hybridizing specifically to", refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target polynucleotide sequence. An extensive guide to the hybridization of nucleic acids is found in Tijssen (1993) *Laboratory Techniques in Biochemistry and Molecular Biology— Hybridization with Nucleic Acid Probes*, part I, chapter 2, "Overview of principles of hybridization and the strategy of nucleic acid probe assays," (Elsevier, New York), as well as in Ausubel, supra. Hames and Higgins (1995) *Gene Probes* 1, IRL Press at Oxford University Press, Oxford, England (Hames and Higgins 1) and Hames and Higgins (1995) *Gene Probes* 2, IRL Press at Oxford University Press, Oxford, England (Hames and Higgins 2) provide details on the synthesis, labeling, detection and quantification of DNA and RNA, including oligonucleotides.

"Stringent hybridization and wash conditions" in the context of nucleic acid hybridization experiments, such as Southern and northern hybridizations, are sequence dependent, and are different under different environmental parameters. An extensive guide to the hybridization of nucleic acids is found in Tijssen (1993), supra, and in Hames and Higgins 1 and Hames and Higgins 2, supra.

For purposes of the present invention, generally, "highly stringent" hybridization and wash conditions are selected to be about 5° C. or less lower than the thermal melting point ($T_m$) for the specific sequence at a defined ionic strength and pH (as noted below, highly stringent conditions can also be referred to in comparative terms). The $T_m$ is the temperature (under defined ionic strength and pH) at which 50% of the test sequence hybridizes to a perfectly matched probe. Very stringent conditions are selected to be equal to the $T_m$ for a particular probe.

The $T_m$ is the temperature of the nucleic acid duplexes indicates the temperature at which the duplex is 50% denatured under the given conditions and its represents a direct measure of the stability of the nucleic acid hybrid. Thus, the $T_m$ corresponds to the temperature corresponding to the midpoint in transition from helix to random coil; it depends on length, nucleotide composition, and ionic strength for long stretches of nucleotides.

After hybridization, unhybridized nucleic acid material can be removed by a series of washes, the stringency of which can be adjusted depending upon the desired results. Low stringency washing conditions (e.g., using higher salt and lower temperature) increase sensitivity, but can product nonspecific hybridization signals and high background signals. Higher stringency conditions (e.g., using lower salt and higher temperature that is closer to the hybridization temperature) lowers the background signal, typically with only the specific signal remaining. See, Rapley, R. and Walker, J. M. eds., *Molecular Biomethods Handbook* (Humana Press, Inc. 1998) (hereinafter "Rapley and Walker"), which is incorporated herein by reference in its entirety for all purposes.

The $T_m$ of a DNA-DNA duplex can be estimated using the following equation:

$$T_m(°C.)=81.5°C.+16.6(\log_{10}M)+0.41(\% \, G+C)-0.72(\% \, f)-500/n.$$

where M is the molarity of the monovalent cations (usually Na+), (% G+C) is the percentage of guanosine (G) and cystosine (C) nucleotides, (% f) is the percentage of formamide and n is the number of nucleotide bases (i.e., length) of the hybrid. See, Rapley and Walker, supra.

The $T_m$ of an RNA-DNA duplex can be estimated as follows:

$$T_m(°C.)=79.8°C.+18.5(\log_{10}M)+0.58(\% \, G+C)-11.8(\% \, G+C)^2-0.56 \, (\% \, f)-820/n$$

where M is the molarity of the monovalent cations (usually Na+), (% G+C) is the percentage of guanosine (G) and cystosine (C) nucleotides, (% f) is the percentage of formamide and n is the number of nucleotide bases (i.e., length) of the hybrid. Id.

Equations 1 and 2 are typically accurate only for hybrid duplexes longer than about 100–200 nucleotides. Id.

The Tm of nucleic acid sequences shorter than 50 nucleotides can be calculated as follows:

$$T_m(°C.)=4(G+C)+2(A+T)$$

where A (adenine), C, T (thymine), and G are the numbers of the corresponding nucleotides.

An example of stringent hybridization conditions for hybridization of complementary nucleic acids which have more than 100 complementary residues on a filter in a Southern or northern blot is 50% formamide (or formalin) with 1 mg of heparin at 42° C., with the hybridization being carried out overnight. An example of stringent wash conditions is a 0.2×SSC wash at 65° C. for 15 minutes (see Sambrook, supra for a description of SSC buffer). Often the high stringency wash is preceded by a low stringency wash to remove background probe signal. An example low stringency wash is 2×SSC at 40° C. for 15 minutes.

In general, a signal to noise ratio of 2.5×–5× (or higher) than that observed for an unrelated probe in the particular hybridization assay indicates detection of a specific hybridization. Detection of at least stringent hybridization between two sequences in the context of the present invention indicates relatively strong structural similarity or homology to, e.g., the nucleic acids of the present invention provided in the sequence listings herein.

As noted, "highly stringent" conditions are selected to be about 5° C. or less lower than the thermal melting point ($T_m$) for the specific sequence at a defined ionic strength and pH. Target sequences that are closely related or identical to the nucleotide sequence of interest (e.g., "probe") can be identified under highly stringency conditions. Lower stringency conditions are appropriate for sequences that are less complementary. See, e.g., Rapley and Walker, supra.

Comparative hybridization can be used to identify nucleic acids of the invention, and this comparative hybridization method is a preferred method of distinguishing nucleic acids of the invention. Detection of highly stringent hybridization between two nucleotide sequences in the context of the present invention indicates relatively strong structural similarity/homology to, e.g., the nucleic acids disclosed herein. Highly stringent hybridization between two nucleotide sequences demonstrates a degree of similarity or homology of structure, nucleotide base composition, arrangement or order that is greater than that detected by stringent hybridization conditions. In particular, detection of highly stringent hybridization in the context of the present invention indicates strong structural similarity or structural homology (e.g., nucleotide structure, base composition, arrangement or order) to, e.g., the nucleic acids provided in the sequence listings herein. For example, it is desirable to identify test nucleic acids which hybridize to the exemplar nucleic acids herein under stringent conditions.

Thus, one measure of stringent hybridization is the ability to hybridize to one of the listed nucleic acids (e.g., nucleic acid sequences SEQ ID NO:1 to SEQ ID NO:18, and complementary polynucleotide sequences and fragments thereof) under highly stringent conditions (or very stringent conditions, or ultra-high stringency hybridization conditions, or ultra-ultra high stringency hybridization conditions). Stringent hybridization (including, e.g., highly stringent, ultra-high stringency, or ultra-ultra high stringency hybridization conditions) and wash conditions can easily be determined empirically for any test nucleic acid.

For example, in determining highly stringent hybridization and wash conditions, the hybridization and wash conditions are gradually increased (e.g., by increasing temperature, decreasing salt concentration, increasing detergent concentration and/or increasing the concentration of organic solvents, such as formalin, in the hybridization or wash), until a selected set of criteria are met. For example, the hybridization and wash conditions are gradually increased until a probe comprising one or more nucleic acid sequences selected from SEQ ID NO:1 to SEQ ID NO:18, and complementary polynucleotide sequences and fragments thereof, binds to a perfectly matched complementary target (again, a nucleic acid comprising one or more nucleic acid sequences selected from SEQ ID NO:1 to SEQ ID NO:18, and complementary polynucleotide sequences and fragments thereof), with a signal to noise ratio that is at least 2.5×, and optionally 5× or more as high as that observed for hybridization of the probe to an unmatched target. In this case, the unmatched target is a nucleic acid corresponding to, e.g., a known CMV promoter/enhancer homologue, e.g., a CMV promoter/enhancer homologue homologue nucleic acid (other than those in the accompanying sequence listing) that is present in a public database such as GenBank™ at the time of filing of the subject application. Examples of such unmatched target nucleic acids include, e.g., nucleic acid sequences represented by GENSEQ reference numbers: N91042, T77193, Q43524, Q53550, N60156, Q43525; by GenBank accession nos.: K03104.1, X03922.1, NC_001347.1, X17403.1; or by other similar molecules found in any public database. (The GenBank accession nos. for the first four GENSEQ sequences are: A01321, AR094363, AR050546, AR050544.)

A test nucleic acid is said to specifically hybridize to a probe nucleic acid when it hybridizes at least ½ as well to the probe as to the perfectly matched complementary target, i.e., with a signal to noise ratio at least ½ as high as hybridization of the probe to the target under conditions in which the perfectly matched probe binds to the perfectly matched complementary target with a signal to noise ratio that is at least about 2.5×–10×, typically 5×–10× as high as that observed for hybridization to any of the unmatched target nucleic acids.

Ultra high-stringency hybridization and wash conditions are those in which the stringency of hybridization and wash conditions are increased until the signal to noise ratio for binding of the probe to the perfectly matched complementary target nucleic acid is at least 10 × as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-high stringency conditions.

Similarly, even higher levels of stringency can be determined by gradually increasing the hybridization and/or wash conditions of the relevant hybridization assay. For example, those in which the stringency of hybridization and wash conditions are increased until the signal to noise ratio for binding of the probe to the perfectly matched complementary target nucleic acid is at least 10×, 20×, 50×, 100×, or 500× or more as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-ultra-high stringency conditions.

Target nucleic acids which hybridize to the nucleic acids represented by SEQ ID NO: 1 to SEQ ID NO: N and complementary polynucleotide sequences and fragments thereof under high, ultra-high and ultra-ultra high stringency conditions are a feature of the invention.

For distinguishing between duplexes with sequences of less than about 100 nucleotides, a TMAC1 hybridization procedure known to those of ordinary skill in the art can be used. See, e.g., Sorg, U. et al. 1 Nucleic Acids Res. (Sep. 11, 1991) 19(17), incorporated herein by reference in its entirety for all purposes.

"Substantially the entire length of a polynucleotide sequence" or "substantially the entire length of a polypeptide sequence" refers to at least about 50%, generally at least about 60%, 70%, or 75%, usually at least about 80%, or typically at least about 85%, 86%, 87%, 88%, 89%, 90%, 91%, 92%, 93%, 94%, 95%, 96%, 97%, 98%, 99%, 99.5% or more of a length of a polynucleotide sequence or polypeptide sequence.

A "polypeptide sequence" is a polymer of amino acids (a protein, polypeptide, etc., comprising amino acid residues) or a character string representing an amino acid polymer, depending on context. Given the degeneracy of the genetic code, one or more nucleic acids, or the complementary nucleic acids thereof, that encode a specific polypeptide sequence can be determined from the polypeptide sequence.

A "fragment" or "subsequence" is any portion of an entire polynucleotide or polypeptide sequence. Thus, a "subsequence" refers to a sequence of nucleic acids or amino acids that comprises a part of a longer sequence of nucleic acids (e.g., polynucleotide) or amino acids (e.g., polypeptide) respectively. In one aspect, the invention provides a nucleic acid comprising a fragment that comprises a unique subsequence in a nucleic acid selected from SEQ ID NO:1 to SEQ ID NO:18 or complementary polynucleotide sequence or a fragment thereof. The unique subsequence is unique as compared to subsequences of any of the nucleic acid sequences represented by GENSEQ reference numbers: N91042, T77193, Q43524, Q53550, N60156, Q43525; by GenBank accession nos.: K03104.1,X03922.1, NC_001347.1,X17403.1; or by other similar molecules found in any public database or complementary polynucleotide sequences thereof. (The GenBank accession nos. for the first four GENSEQ sequences are: A01321, AR094363, AR050546, AR050544.) Such unique subsequences can be determined by aligning any of SEQ ID NO: 1 to SEQ ID NO: N or corresponding complementary sequences or fragments against the complete set of nucleic acids available, e.g., in a public database, at the filing date of the subject application. Alignment can be performed using the BLAST algorithm set to default parameters. Any unique subsequence is useful, e.g., as a probe to identify the nucleic acids of the invention.

A nucleic acid, protein, peptide, polypeptide, or other component is "isolated" when it is partially or completely separated from components with which it is normally associated (other peptides, polypeptides, proteins (including complexes, e.g., polymerases and ribosomes which may accompany a native sequence), nucleic acids, cells, synthetic reagents, cellular contaminants, cellular components, etc.), e.g., such as from other components with which it is normally associated in the cell from which it was originally derived. A nucleic acid, polypeptide, or other component is isolated when it is partially or completely recovered or separated from other components of its natural environment such that it is the predominant species present in a composition, mixture, or collection of components (i.e., on a molar basis it is more abundant than any other individual species in the composition). In preferred embodiments, the preparation consists of more than about 70% or 75%, typically more than about 80%, or preferably more than about 90% of the isolated species.

In one aspect, a "substantially pure" or "isolated" nucleic acid (e.g., RNA or DNA), polypeptide, protein, or composition also means where the object species (e.g., nucleic acid or polypeptide) comprises at least about 50, 60, or 70 percent by weight (on a molar basis) of all macromolecular species present. A substantially pure or isolated composition can also comprise at least about 80, 90, or 95 percent by weight of all macromolecular species present in the composition. An isolated object species can also be purified to essential homogeneity (contaminant species cannot be detected in the composition by conventional detection methods) wherein the composition consists essentially of derivatives of a single macromolecular species. The term "purified" generally denotes that a nucleic acid, polypeptide, or protein gives rise to essentially one band in an electrophoretic gel. It typically means that the nucleic acid, polypeptide, or protein is at least about 50% pure, 60% pure, 70% pure, 75% pure, more preferably at least about 85% pure, and most preferably at least about 99% pure.

The term "isolated nucleic acid" may refer to a nucleic acid (e.g., DNA or RNA) that is not immediately contiguous with both of the sequences with which it is immediately contiguous (i.e., one at the 5' and one at the 3' end) in the naturally occurring genome of the organism from which the nucleic acid of the invention is derived. Thus, this term includes, e.g., a cDNA or a genomic DNA fragment produced by polymerase chain reaction (PCR) or restriction endonuclease treatment, whether such cDNA or genomic DNA fragment is incorporated into a vector, integrated into the genome of the same or a different species than the organism, including, e.g., a virus, from which it was originally derived, linked to an additional coding sequence to form a hybrid gene encoding a chimeric polypeptide, or independent of any other DNA sequences. The DNA may be double-stranded or single-stranded, sense or antisense.

The term "recombinant" when used with reference, e.g., to a cell, vector, nucleic acid, or polypeptide typically indicates that the cell, vector, nucleic acid or polypeptide has been modified by the introduction of a heterologous (or foreign) nucleic acid or the alteration of a native nucleic acid, or that the polypeptide has been modified by the introduction of a heterologous amino acid, or that the cell is derived from a cell so modified. Recombinant cells express nucleic acid sequences (e.g., genes) that are not found in the native (non-recombinant) form of the cell or express native nucleic acid sequences (e.g., genes) that would be abnormally expressed, under-expressed, or not expressed at all. The term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques.

The terms "recombinant polynucleotide" or a "recombinant polypeptide" encompass a non-naturally occurring polynucleotide or polypeptide that includes nucleic acid or amino acid sequences, respectively, from more than one source nucleic acid or polypeptide, which source nucleic acid or polypeptide can be a naturally occurring nucleic acid or polypeptide, or can itself have been subjected to mutagenesis or other type of modification. A nucleic acid or polypeptide may be deemed "recombinant" when it is artificial or engineered, or derived from an artificial or engineered polypeptide or nucleic acid. A recombinant nucleic acid (e.g., DNA or RNA) can be made by the combination (e.g., artificial combination) of at least two segments of sequence that are not typically included together, not typically associated with one another, or are otherwise typically separated from one another. A recombinant nucleic acid can comprise a nucleic acid molecule formed by the joining together or combination of nucleic acid segments from different sources and/or artificially synthesized. A "recombinant polypeptide" (or "recombinant protein") often refers to a polypeptide (or protein) that results from a cloned or recombinant nucleic acid or gene. The source polynucleotides or polypeptides from which the different nucleic acid or amino acid sequences are derived are sometimes homologous (i.e., have, or encode a polypeptide that encodes, the same or a similar structure and/or function), and are often from different isolates, serotypes, strains, species, of organism or from different disease states, for example.

The term "recombinantly produced" refers to an artificial combination usually accomplished by either chemical synthesis means, recursive sequence recombination of nucleic acid segments or other diversity generation methods (such as, e.g., shuffling) of nucleotides, or manipulation of isolated segments of nucleic acids, e.g., by genetic engineering techniques known to those of ordinary skill in the art. "Recombinantly expressed" typically refers to techniques for the production of a recombinant nucleic acid in vitro and transfer of the recombinant nucleic acid into cells in vivo, in vitro, or ex vivo where it may be expressed or propagated.

"Naturally occurring" as applied to an object refers to the fact that the object can be found in nature as distinct from being artificially produced by man. For example, a polypeptide or polynucleotide sequence that is present in an organism (including viruses, bacteria, protozoa, insects, plants or mammalian tissue) that can be isolated from a source in nature and that has not been intentionally modified by man in the laboratory is naturally occurring. A "non-naturally occurring" object is one that is not found in nature or is found in nature in a different form.

A nucleic acid is "operably linked" when it is placed into a functional relationship with another nucleic acid sequence. For instance, a promoter or enhancer is operably linked to a coding sequence if it directs or increases the transcription of the coding sequence. A nucleic acid is said to "promote the expression" of an operably linked coding sequence if the nucleic acid acts as a promoter (i.e., direct transcription) or as an enhancer (i.e., increases transcription). "Operably linked" means that the DNA sequences being linked are typically contiguous and, where necessary to join two protein coding regions, contiguous and in reading frame. However, since enhancers generally function when separated from the promoter by several kilobases and intronic sequences may be of variable lengths, some polynucleotide elements may be operably linked but not contiguous.

A "recombinant expression cassette" or simply an "expression cassette" is a nucleic acid construct, generated recombinantly or synthetically, with operably linked nucleic acid elements that are capable of effecting expression of a structural gene in hosts compatible with such sequences. Expression cassettes include at least a promoter and optionally, a transcription termination signal. Typically, the recombinant expression cassette includes a nucleic acid to be transcribed (e.g., a nucleic acid encoding a desired polypeptide), which is termed a "transgene," and a promoter. Additional factors necessary or helpful in effecting expression may also be used as described herein. For example, an expression cassette can also include nucleotide sequences that encode a signal sequence that directs secretion of an expressed protein from the host cell. Enhancers, and other nucleic acid sequences that influence gene expression, can also be included in an expression cassette.

An "exogenous" nucleic acid," "exogenous DNA segment," "heterologous sequence," or "heterologous nucleic acid," as used herein, is one that originates from a source foreign to the particular host cell, or, if from the same source, is modified from its original form. Thus, a heterologous gene in a host cell includes a gene that is endogenous to the particular host cell, but has been modified. The terms refer to a DNA segment which is foreign or heterologous to the cell, or homologous to the cell but in a position within the host cell nucleic acid in which the element is not ordinarily found. Exogenous DNA segments are expressed to yield exogenous polypeptides.

A vector is a component or composition for facilitating cell transduction, transfection, or infection by a selected nucleic acid, or expression of the nucleic acid in the cell. Vectors include, e.g., plasmids, cosmids, viruses, YACs, bacteria, poly-lysine, etc. An "expression vector" is a nucleic acid construct or sequence, generated recombinantly or synthetically, with a series of specific nucleic acid elements that permit transcription of a particular nucleic acid in a host cell. The expression vector can be part of a plasmid, virus, or nucleic acid fragment. The expression vector typically includes a nucleic acid to be transcribed (i.e., a transgene) operably linked to a promoter. The nucleic acid to be transcribed is typically under the direction or control of the promoter.

Variants of the exemplary nucleic acids described herein can be selected or screened for nucleic acids with or which confer desirable properties, such as the ability to promote expression of an operably linked transgene at a desired level. The term "screening" describes, in general, a process that identifies optimal molecules of the present invention, such as, e.g., the novel promoters, fragments and homologues thereof, and related expression cassettes and vectors. For screening and selection, these molecules are linked to or include a transgene that encodes a conveniently measured marker polypeptide. Other marker polypeptides that can be used in selection and screening include, for example, those that bind to a receptor, and/or induce or inhibit a desired biological response in a test system or an in vitro, ex vivo or in vivo application (e.g., induce or inhibit a T-cell proliferation response). Selection is a form of screening in which identification and physical separation are achieved simultaneously by expression of a selection marker, which, in some genetic circumstances, allows cells expressing the marker to survive while other cells die (or vice versa). Screening markers include, for example, luciferase, beta-galactosidase and green fluorescent protein, and the like. Selection markers include drug and toxin resistance genes, and the like. Although spontaneous selection can and does occur in the course of natural evolution, in the present methods, selection is performed by man.

A "specific binding affinity" between two molecules, e.g., a ligand and a receptor, means a preferential binding of one molecule for another in a mixture of molecules. The binding of the molecules can be considered specific if the binding affinity is about $1\times10^4$ $M^{-1}$ to about $1\times10^7$ $M^{-1}$ (i.e., about $10^{-4}$–$10^{-7}$ M) or greater.

The term "subject" as used herein includes, but is not limited to, an organism, such as a mammal, including, e.g., a human, non-human primate (e.g., baboon, orangutan, monkey), mouse, pig, cow, goat, cat, rabbit, rat, guinea pig, hamster, horse, monkey, sheep, or other non-human mammal; a non-mammal, including, e.g., a non-mammalian vertebrate, such as a bird (e.g., a chicken or duck) or a fish, and a non-mammalian invertebrate.

The term "pharmaceutical composition" means a composition suitable for pharmaceutical use in a subject, including an animal or human. A pharmaceutical composition generally comprises an effective amount of an active agent and a carrier, including, e.g., a pharmaceutically acceptable carrier.

The term "effective amount" means a dosage or amount sufficient to produce a desired result. The desired result may comprise an objective or subjective improvement in the subject receiving the dosage or amount.

A "prophylactic treatment" is a treatment administered to a subject who does not display signs or symptoms of a disease, pathology, or medical disorder, or displays only early signs or symptoms of a disease, pathology, or disorder, such that treatment is administered for the purpose of diminishing, preventing, or decreasing the risk of developing the disease, pathology, or medical disorder. A prophylactic treatment functions as a preventative treatment against a disease or disorder. A "prophylactic activity" is an activity of an agent, such as a nucleic acid, vector, gene, polypeptide, protein, substance, or composition thereof that, when administered to a subject who does not display signs or symptoms of a pathology, disease or disorder, or who displays only early signs or symptoms of a pathology, disease, or disorder, diminishes, prevents, or decreases the risk of the subject developing the pathology, disease, or disorder. This effect is termed a "prophylactic effect." A "prophylactically useful" agent or compound (e.g., nucleic acid or polypeptide) refers to an agent or compound that is useful in diminishing, preventing, treating, or decreasing development of a pathology, disease or disorder.

A "therapeutic treatment" is a treatment administered to a subject who displays symptoms or signs of a pathology, disease, or disorder, in which treatment is administered to the subject for the purpose of diminishing or eliminating those signs or symptoms of the pathology, disease, or disorder. A "therapeutic activity" is an activity of an agent, such as a nucleic acid, vector, gene, polypeptide, protein, substance, or composition thereof, that eliminates or diminishes signs or symptoms of a pathology, disease or disorder, when administered to a subject suffering from such signs or symptoms. This effect is termed a "therapeutic effect." A "therapeutically useful" agent or compound (e.g., nucleic acid or polypeptide) indicates that an agent or compound is useful in diminishing, treating, or eliminating such signs or symptoms of a pathology, disease or disorder.

An "immunogen" refers to a substance capable of provoking an immune response, and includes, e.g., antigens, autoantigens that play a role in induction of autoimmune diseases, and tumor-associated antigens expressed on cancer cells. An immune response of any type to an immunogen is termed an "immunogenic effect." An "immunomodulatory molecule" refers to a substance capable of altering an immune response provoked by an immunogen.

An "antigen" refers to a substance that is capable of eliciting the formation of antibodies in a host or generating a specific population of lymphocytes reactive with that substance. Antigens are typically macromolecules (e.g., proteins and polysaccharides) that are foreign to the host.

An "adjuvant" refers to a substance that enhances an antigen's immune-stimulating properties or the pharmacological effect of a drug. For example, "Freund's Complete Adjuvant" is an emulsion of oil and water containing an immunogen, an emulsifying agent and mycobacteria. Another example, "Freund's incomplete adjuvant," is the same but without mycobacteria.

The term "cytokine" includes, for example, interleukins, interferons, chemokines, hematopoietic growth factors, tumor necrosis factors and transforming growth factors. In general these are small molecular weight proteins that regulate maturation, activation, proliferation, and differentiation of the cells of the immune system.

Generally speaking, a "co-stimulatory molecule" refers to a molecule that acts in association or conjunction with, or is involved with, a second molecule or with respect to an immune response in a co-stimulatory pathway. In one aspect, a co-stimulatory molecule may be an immunomodulatory molecule that acts in association or conjunction with, or is involved with, another molecule to stimulate or enhance. In another aspect, a co-stimulatory molecule is an immunomodulatory molecule that acts in association or conjunction with, or is involved with, another molecule to inhibit or suppress an immune response. A co-stimulatory molecule need act simultaneously with, or by the same mechanism, as the second molecule. Exemplary co-stimulatory molecules include, e.g., B7-1 (CD80) and B7-2 (CD86) polypeptide ligands, which are expressed on antigen-presenting cells and act with an antigen in the stimulation of a T cell receptor to effectuate an immune response. Additional co-stimulatory molecules include CD54 or CD50 (ICAM), CD11a/18 (LFA-1) CD40, and ICOS (B7-H) which are also expressed on antigen-presenting cells. Other co-stimulatory polypeptides include, respectively, polypeptides that bind CD28 and/or CTLA-4 receptors on T cells (see, e.g., copending, commonly assigned U.S. patent application Ser. No. 09/888,324, entitled "Novel Co-Stimulatory Molecules," filed Jun. 21, 2001 as LJAQ Generally, the nomenclature used hereafter and the laboratory procedures in cell culture, molecular genetics, molecular biology, nucleic acid chemistry, and protein chemistry described below are those well known and commonly employed by those of ordinary skill in the art. Standard techniques, such as described in Sambrook et al., Molecular Cloning: A Laboratory Manual (2nd Ed.), Vols. 1–3, Cold Spring Harbor Laboratory, Cold Spring Harbor, N.Y., 1989 (hereinafter "Sambrook") and Current Protocols in Molecular Biology, F. M. Ausubel et al., eds., Current Protocols, a joint venture between Greene Publishing Associates, Inc. and John Wiley & Sons, Inc. (1994, supplemented through 1999) (hereinafter "Ausubel"), are used for recombinant nucleic acid methods, nucleic acid synthesis, cell culture methods, and transgene incorporation, e.g., electroporation, injection, and lipofection. Generally, oligonucleotide synthesis and purification steps are performed according to specifications. The techniques and procedures are generally performed according to conventional methods in the art and various general references which are provided throughout this document. The procedures therein are believed to be well known to those of ordinary skill in the art and are provided for the convenience of the reader.

Description of the Preferred Embodiments

A. In General

The major immediate-early (IE) region transcriptional regulatory elements, including promoter and enhancer sequences (the promoter/enhancer region), of cytomegalovirus is widely used for regulating transcription of genes, because it is highly active in a broad range of host cell types (see, e.g., Foecking et al., *Gene* 45:101–105 (1986)). The human CMV promoter/enhancer region has been found to be a strong promoter/enhancer (Boshart et al., *Cell* 41:521–530 (1985); Thomsen et al., *Proc Natl Acad Sci* 81:659–663 (1984)), including in transient expression systems (Foecking et al., *Gene* 45:101–105 (1986); Pasleau et al., *Gene* 38:227–232 (1985)). The human CMV promoter has been shown to be a source of transcriptional signal elements for expression of a variety of heterologous proteins (Cockett et al., *Biotechnology* 8:662–667 (1990); Eaton et al., *Biochemistry* 25:8343–8353 (1986)).

Because the CMV promoter and enhancer are active in human and animal cells, the improved (optimized) CMV promoter/enhancer elements can be used to express foreign genes, including antigens, such as, e.g., the cancer antigen EpCam/KSA and recombinant forms thereof. Other examples of cancer antigens that can be expressed using the promoter/enhancer elements of the invention include, e.g., bullous pemphigoid antigen 2, prostate mucin antigen (PMA) (Beckett and Wright (1995) Int. J. Cancer 62:703–710), tumor associated Thomsen-Friedenreich antigen (Dahlenborg et al. (1997) Int. J. Cancer 70:63–71), prostate-specific antigen (PSA) (Dannull and Belldegrun (1997) Br. J. Urol. 1:97–103), luminal epithelial antigen (LEA.135) of breast carcinoma and bladder transitional cell carcinoma (TCC) (Jones et al. (1997) Anticancer Res. 17:685–687), cancer-associated serum antigen (CASA) and cancer antigen 125 (CA 125) (Kierkegaard et al. (1995) Gynecol. Oncol. 59:251–254), the epithelial glycoprotein 40 (EGP40) (Kievit et al. (1997) Intl. J. Cancer 71:237–245), squamous cell carcinoma antigen (SCC) (Lozza et al. (1997) Anticancer Res. 17: 525–529), cathepsin E (Mota et al. (1997) Am. J. Pathol. 150:1223–1229), tyrosinase in melanoma (Fishman et al. (1997) Cancer 79: 1461–1464), cell nuclear antigen (PCNA) of cerebral cavemomas (Notelet et al. (1997) Surg. Neurol. 47: 364–370), DF3/MUC1 breast cancer antigen (Apostolopoulos et al. (1996) Immunol. Cell. Biol. 74: 457–464; Pandey et al. (1995) Cancer Res. 55: 4000–4003), carcinoembryonic antigen (Paone et al. (1996) J. Cancer Res. Clin. Oncol. 122:499–503; Schlom et al. (1996) Breast Cancer Res. Treat. 38:27–39), tumor-associated antigen CA 19–9 (Tolliver and O'Brien (1997) South Med. J. 90:89–90; Tsuruta et al. (1997) Urol. Intl. 58:20–24), human melanoma antigens MART-1/Melan-A27-35 and gp1OO (Kawakami and Rosenberg (1997) Intl. Rev. Immunol. 14:173–192; Zajac et al. (1997) Intl. J. Cancer 71:491–496), the T and Tn pancarcinoma (CA) glycopeptide epitopes (Springer (1995) Crit. Rev. Oncog. 6:57–85), a 35 kD tumor-associated autoantigen in papillary thyroid carcinoma (Lucas et al. (1996) Anticancer Res. 16:2493–2496), KH-1 adenocarcinoma antigen (Deshpande and Danishefsky (1997) Nature 387:164–166), the A60 mycobacterial antigen (Maes et al. (1996) J. Cancer Res. Clin. Oncol. 122:296–300), heat shock proteins (HSPs) (Blachere and Srivastava (1995) Semin. Cancer Biol. 6:349–355), and MAGE, tyrosinase, melan-A and gp75 and mutant oncogene products (e.g., p53, ras, CDk4, and HER-2/neu (Bueler and Mulligan (1996) Mol. Med. 2:545–555; Lewis and Houghton (1995) Semin. Cancer Biol. 6: 321–327; Theobald et al. (1995) Proc. Nat'l. Acad. Sci. USA 92: 11993–11997), prostate specific membrane antigen (PSMA) Bangma CH et al. (2000) Microsc Res Tech 51:430–5, TAG-72, McGuinness RP et al. Hum Gene Ther (1999) 10:165–73, and variants, derivatives, and mutated, and recombinant forms (e.g., shuffled forms) thereof of these antigens.

The promoter/enhancer elements can also be used to express co-stimulatory molecules, including, e.g., B7-1 and B7-2 ligands, CD54 or CD50 (ICAM), CD11a/18 (LFA-1) CD40, and ICOS (B7-H). Other co-stimulatory polypeptides include, respectively, polypeptides that bind CD28 and/or CTLA-4 receptors on T cells (see, e.g., copending commonly assigned U.S. patent application Ser. No. 09/888,324, entitled "Novel Co-Stimulatory Molecules," filed Jun. 21, 2001 as LJAQ. The promoter/enhancer elements can also be use to express adjuvants, etc. In all of these embodiments, the improved (optimized) CMV promoter/enhancer elements can be used both in animal and human models and in a variety of applications, including therapeutic and prophylactic treatment methods described herein.

The ability to control gene expression, especially mammalian gene expression, is of particular importance to the success of genetic vaccination and gene therapy, protein-based vaccines and immunotherapy treatments, and also in the production in culture of therapeutic and prophylactic polypeptides and proteins useful for treatment methods or other applications.

In preferred embodiments, the present invention provides for improved, optimized CMV transcriptional regulatory elements, generated by recursive sequence recombination methods, such as, e.g., DNA shuffling, which provide for optimized levels of gene expression (including, e.g., expression of genes encoding antigens, co-stimulatory molecules, adjuvants, etc.), and/or direct long-term and regulatable transgene expression. The desired (optimized) level of gene expression can be a significantly increased expression (high-level expression), an slightly increased expression (intermediate-level expression), or a reduced or low expression (low- or reduced-level expression), wherein each such level is compared, e.g., to a known or wild-type CMV molecule comprising such regulatory elements). The desired level of gene expression depends upon the particular need or application. Promoter sequences that are optimal for any given application can be identified by screening libraries of chimeric nucleic acids produced as described herein using criteria suitable for the intended application.

For example, optimized promoters that produce increased levels of expression and direct long-term and regulatable transgene expression would be particularly useful in genetic (DNA) vaccination, other immunostimulatory applications, and therapeutic and prophylactic methods, since they would likely improve the efficacy of such applications. In genetic vaccination methods, a genetic vaccine vector expresses a gene sequence encoding an antigen or adjuvant, which elicits or potentiates an immune response.

Generally, in standard genetic vaccination applications described previously, an insufficient amount of antigen is expressed for effective treatment. An optimized promoter having an ability to express a greater amount of one or more antigens and/or adjuvants may be preferred depending on the particular therapeutic or prophylactic treatment objective (e.g., for treatment of a viral infection, such as hepatitis B or C infection, or of other infectious diseases; chronic diseases, especially those in which an enhanced immune response is desired; or a particular cancer).

In other genetic vaccination applications where, e.g., the particular antigen of interest causes too strong an immune response or is too active in the subject in which it is expressed (with possibly lethal or adverse effects), a promoter of the invention optimized to express a lower or intermediate level of antigen (compared, e.g., to a known promoter, such as a hCMV promoter) can be prepared and used be used with the antigen or adjuvant (e.g., in an expression vector format comprising the optimized promoter operably linked to a nucleic acid sequence encoding the antigen or adjuvant of interest) so as to avoid the deleterious or unwanted consequences.

In some applications, the concentration of each of one or more antigens, adjuvants, or prophylactic or therapeutic agents is important. For example, in immunotherapy methods employing co-stimulatory molecules, the relative concentrations of these molecules is important, since the concentration of one such molecule may affect the concentration of another. For example, it is often desirable to express low or intermediate level concentrations of one or more co-stimulatory molecules (compared, e.g., to expression levels induced by known or standard promoters, such as hCMV promoters). The promoter can thus be optimized to direct the expression of one or more co-stimulatory molecules in a particular application.

In some applications, as, e.g., in certain DNA vaccines, it may desirable to employ an expression vector comprising a weaker promoter (e.g., a promoter optimized to direct a low- or intermediate-level of expression of a sequence encoding an antigen). For example, it may be desired to induce tolerance to a specific protein expressed by the gene by employing a series of separately administered, increasing doses of an antigen expressed by a DNA vaccine. Thus, it may be beneficial to initiate genetic allergy vaccination with low doses, as is done in conventional immunotherapy. Notably, simply reducing the amount of plasmid DNA injected may not be sufficient, because only few cells expressing the allergy antigen may be sufficient to induce anaphylactic reactions. Therefore, promoters of the invention having a range of activities are likely to be useful in the dose escalation of genetic allergy vaccines. A series of allergy antigen expression vectors, each comprising one or more promoters that induce different levels of antigen expression in vivo, can be employed with successive inoculations (over time) in an allergy treatment program to regulate antigen dose. The amount of allergen expressed is thus boosted with each application for improved efficacy.

In some therapeutic or prophylactic applications, such as, e.g., in a preventive or therapeutic DNA vaccine for a particular cancer, it may be desirable to have a continued or prolonged amount of an antigen, immunomodulatory, or co-stimulatory molecule expressed in the subject being treated. For example, a nucleic acid of the invention that expresses a co-stimulatory molecule, such as a B7-1 or B7-2 molecule, or a variant thereof, or a polypeptide that binds or selectively binds to either or both of the CD28 receptor or CTLA-4 receptor, can be targeted to tumor cells. The promoter used in such DNA vaccine can be optimized for the particular application using the methods and compositions of the invention.

B. Chimeric Promoter/Enhancers

The present invention provides nucleic acids including novel chimeric promoter/enhancers that are useful for expressing genes in a variety of eukaryotic cells, including mammalian cells, and in in vivo or ex vivo applications (including transplantation methods). The promoter/enhancers find use in producing proteins for commercial or other use, gene therapy, genetic vaccinations, and many other uses.

1. Nucleic Acids

The nucleic acids of the invention are generally capable of promoting the expression of an operably linked transgene. Accordingly, the nucleic acids of the invention typically comprises a transcription start site and related sequences (e.g., a "TATA box" and/or a "CAAT" or "CAAAT" box), which can be derived from a CMV promoter sequence or a variant thereof or from a non-CMV promoter sequence. In the latter case, a nucleic acid sequence of the invention includes one or more other CMV sequences (e.g., enhancer sequences) or variants thereof operably linked to the transcription start site.

Preferred nucleic acids of the invention include the chimeric promoter/enhancer sequences disclosed herein (SEQ ID NOS:1–18) as well as complementary polynucleotide sequences thereof. However, the invention also comprises fragments of these polynucleotide sequences, as well as variants including an insertion, substitution, and/or deletion of one or more nucleotides and nucleic acids that are otherwise modified. Preferably, fragments, nucleotides sequence variants, and modified forms of the disclosed polynucleotide sequences (collectively termed "CMV promoter/enhancer variants" for ease of discussion) retain the ability to promote the expression of an operably linked transgene.

Figure 8:
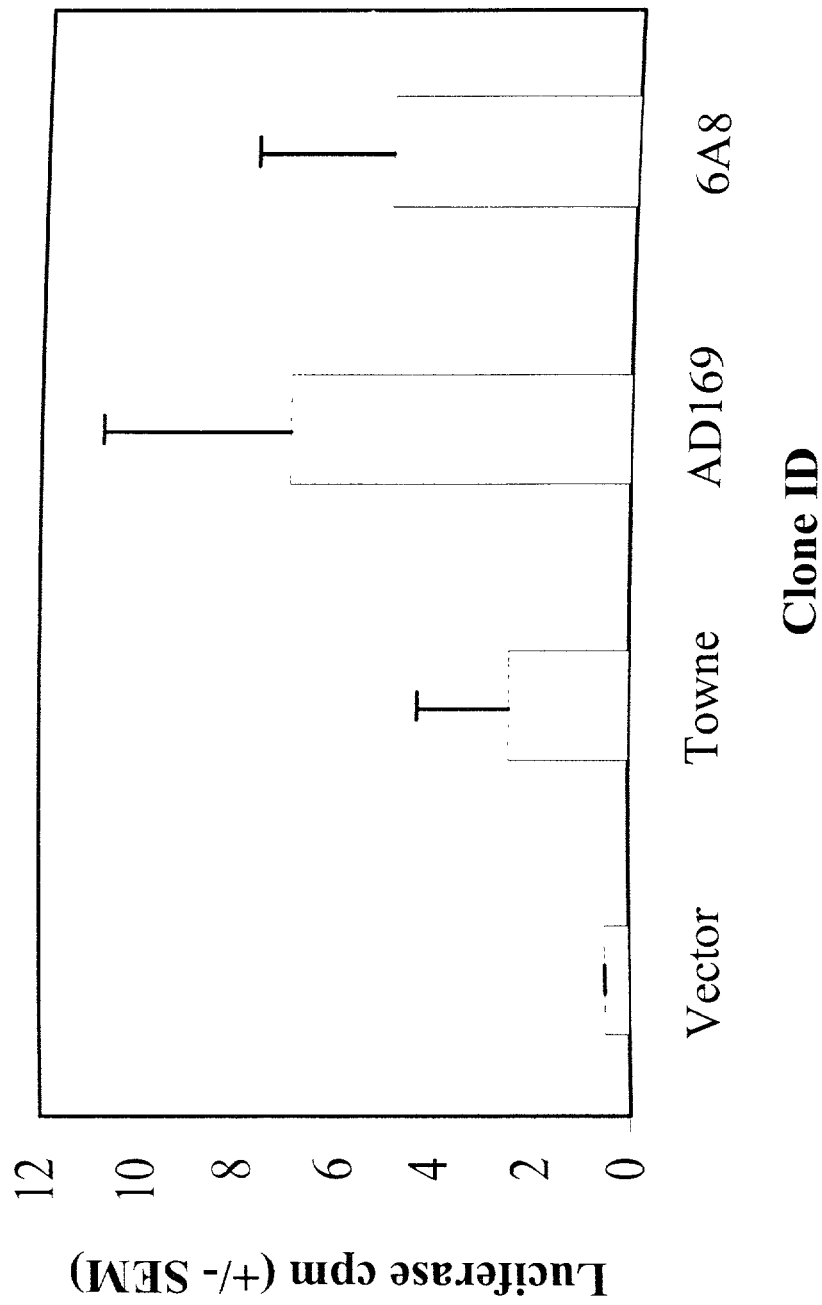
FIGS. 8A–8I shows an alignment of the polynucleotide sequences of WT human AD169 and Towne CMV promoters (SEQ ID NOS:19 and 20) and exemplary polynucleotide sequences of the invention (SEQ ID NOS:1–18). The arrow located between the nucleic acid residue positions equivalent to nucleic acid residues 808–809 of the human Towne CMV promoter sequence indicates the transcription start site. The predicted boundary between the first exon and the first intron is also indicated by an arrow between nucleic acid residues 930 and 931 of the human Towne CMV promoter sequence. The last sequence shown in the alignment (SEQ ID NO:21) represents a "consensus sequence" of aligned polynucleotide sequences. The alignment was prepared using the CLUSTALW multiple sequence alignment algorithm, a pan of the Vector NTI version 6 sequence analysis software package (Informax, Bethesda, Md.). The CLUSTALW program initially performs multiple pairwise comparisons between groups of sequences and then assembles the pairwise alignments into a multiple alignment based on homology. For the initial pairwise alignments, Gap Open and Gap Extension penalties were 10 and 0.1, respectively. For the multiple alignments, Gap Open penalty was 10, and the Gap Extension penalty was 0.05. The protein weight matrix employed was the BLOSUM62 matrix.
Figure 9:
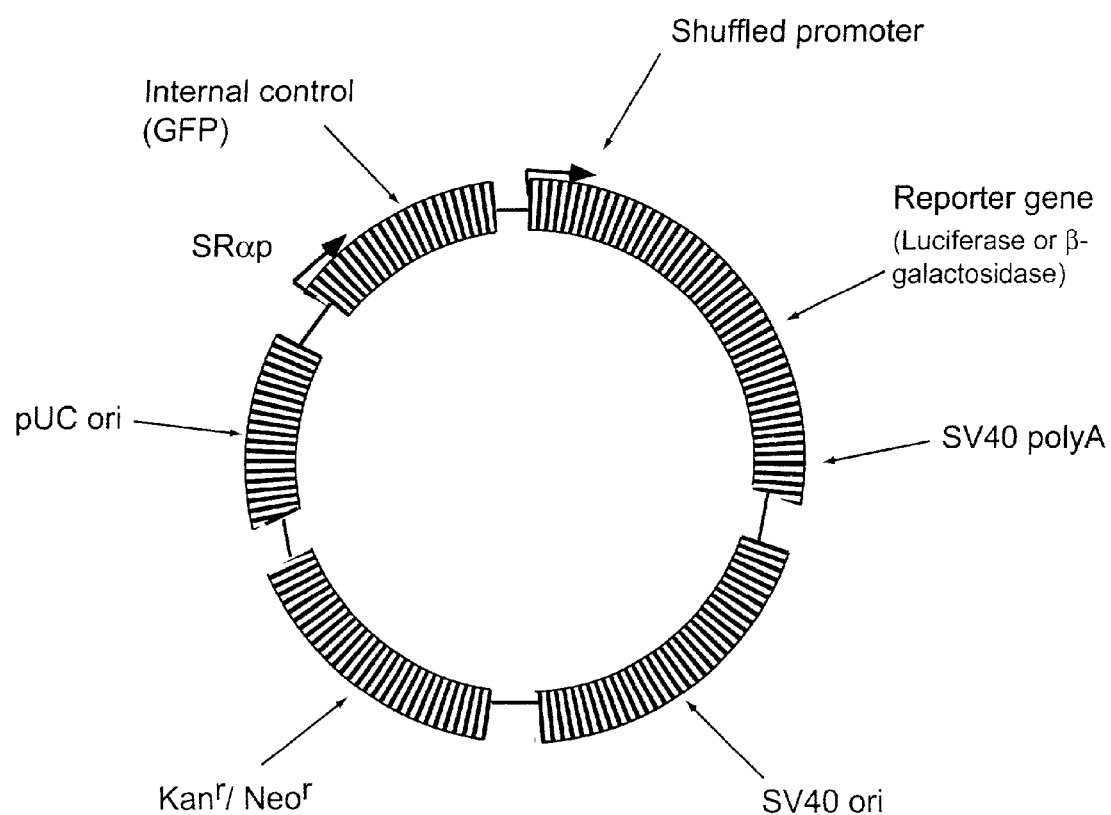
FIG. 9 shows an example of a vector that is useful for screening to identify improved promoters from a library of shuffled promoter nucleic acids. Shuffled putative promoters are inserted into the vector upstream of a reporter gene for which expression is readily detected. For many applications, it is desirable that the product of the reporter gene be a cell surface protein so that cells which express high levels of the reporter gene can be sorted using flow cytometry-based cell sorting using the reporter gene product. Examples of suitable reporter genes include, for example, luciferase, β-galactosidase, or mAb179 epitopes. A polyadenylation region is typically placed downstream of the reporter gene (SV40 polyA is illustrated). The vector can also include a second reporter gene an internal control (GFP; "green fluorescent protein"); this gene is linked to a promoter (SRαp) described herein. The vector also typically includes a selectable marker (kanamycin/neomycin resistance is shown), and origins of replication that are functional in mammalian (SV40 ori) and/or bacterial (pUC ori) cells.

In one embodiment, variants of SEQ ID NOS:1–18 can be designed based on the properties disclosed herein for these polynucleotides. Thus, for example, the 12C9 polynucleotide sequence (SEQ ID NO:3) lacks CMV promoter nucleic acid residues beyond about nucleotide residue 909, numbered according to the consensus sequence shown in FIGS. 8A–8I. Yet this polynucleodde sequence still serves as an efficient promoter of β-galactosidase expression as demonstrated by the in vivo assay for anti-β-galactosidase antibody shown in FIG. 6A. This observation indicates that CMV promoter/enhancer sequences downstream (relative to the direction of transcription) of the residue corresponding to residue 909 in the FIGS. 8A–8I consensus sequence are not required for efficient expression of an operably linked transgene. Accordingly, the invention encompasses nucleic acids that include variants of SEQ ID NOS: 1,2, and 4–18 that lack such downstream CMV promoter/enhancer sequences. In preferred embodiments, such variants include the CAAT box and/or the TATA box (both of these motifs are underlined in FIG. 8E) present in region corresponding to about nucleotide residues 840–890 of the consensus sequence shown in FIGS. 8A–8I. Exemplary nucleic acids of this type lack CMV promoter nucleic acid residues beyond about nucleotide residue 900, 910, 920, 930, and 940, numbered according to this consensus sequence.

The polynucleotide sequences shown in FIGS. 8A–8I include a first exon beginning at about nucleotide residue 810 and extending to about nucleotide residue 932, numbered according to the consensus sequence shown in FIGS. 8A–8I. In some application, it may be desirable to delete this sequence. Thus, invention also encompasses nucleic acids that include variants of SEQ ID NOS: 1,2, and 4–18 lacking these exon sequences. Exemplary nucleic acids of this type lack CMV promoter nucleic acid residues beyond about nucleotide residue 810, 820, 830, 840, 850, 860, 870, 880, and 890, numbered according to this consensus sequence.

Other variants of the disclosed sequences will be apparent to the skilled practitioner in light of the guidance provided herein. The design and production of such CMV promoter/enhancer variants can be carried out using any of a wide variety of diversity generating and/or mutational methods that are available and described in the art, followed by screening or selection of variants for desired properties. The procedures can be used separately, and/or in combination to produce one or more variants of a nucleic acid or set of nucleic acids. Individually and collectively, these procedures provide robust, widely applicable ways of generating diversified nucleic acids and sets of nucleic acids (including, e.g., nucleic acid libraries) useful, e.g., for the engineering or rapid evolution of CMV promoter/enhancer variants derived from the polynucleotide sequences disclosed herein.

Descriptions of a variety of diversity generating procedures for generating nucleic acid variants are found in the following publications and the references cited therein: Soong, N. et al. (2000) "Molecular breeding of viruses" Nat Genet 25(4):436–439; Stemmer, et al. (1999) "Molecular breeding of viruses for targeting and other clinical properties" Tumor Targeting 4:1–4; Ness et al. (1999) "DNA Shuffling of subgenomic sequences of subtilisin" Nature Biotechnology 17:893–896; Chang et al. (1999) "Evolution of a cytokine using DNA family shuffling" Nature Biotechnology 17:793–797; Minshull and Stemmer (1999) "Protein evolution by molecular breeding" Current Opinion in Chemical Biology 3:284–290; Christians et al. (1999) "Directed evolution of thymidine kinase for AZT phosphorylation using DNA family shuffling" Nature Biotechnology 17:259–264; Crameri et al. (1998) "DNA shuffling of a family of genes from diverse species accelerates directed evolution" Nature 391:288–291; Crameri et al. (1997) "Molecular evolution of an arsenate detoxification pathway by DNA shuffling," Nature Biotechnology 15:436–438; Zhang et al. (1997) "Directed evolution of an effective fucosidase from a galactosidase by DNA shuffling and screening" Proc. Natl. Acad. Sci. USA 94:4504–4509; Patten et al. (1997) "Applications of DNA Shuffling to Pharmaceuticals and Vaccines" Current Opinion in Biotechnology 8:724–733; Crameri et al. (1996) "Construction and evolution of antibody-phage libraries by DNA shuffling" Nature Medicine 2:100–103; Crameri et al. (1996) "Improved green fluorescent protein by molecular evolution using DNA shuffling" Nature Biotechnology 14:315–319; Gates et al. (1996) "Affinity selective isolation of ligands from peptide libraries through display on a lac repressor 'headpiece dimer'" Journal of Molecular Biology 255:373–386; Stemmer (1996) "Sexual PCR and Assembly PCR" In: The Encyclopedia of Molecular Biology. VCH Publishers, New York. pp. 447–457; Crameri and Stemmer (1995) "Combinatorial multiple cassette mutagenesis creates all the permutations of mutant and wildtype cassettes" BioTechniques 18:194–195; Stemmer et al., (1995) "Single-step assembly of a gene and entire plasmid form large numbers of oligodeoxy-ribonucleotides" Gene, 164:49–53; Stemmer (1995) "The Evolution of Molecular Computation" Science 270: 1510; Stemmer (1995) "Searching Sequence Space" Bio/Technology 13:549–553; Stemmer (1994) "Rapid evolution of a protein in vitro by DNA shuffling" Nature 370:389–391; and Stemmer (1994) "DNA shuffling by random fragmentation and reassembly: In vitro recombination for molecular evolution." Proc. Natl. Acad. Sci. USA 91:10747–10751.

Mutational methods of generating diversity include, for example, site-directed mutagenesis (Ling et al. (1997) "Approaches to DNA mutagenesis: an overview" Anal Biochem. 254(2): 157–178; Dale et al. (1996) "Oligonucleotide-directed random mutagenesis using the phosphorothioate method" Methods Mol. Biol. 57:369–374; Smith (1985) "In vitro mutagenesis" Ann. Rev. Genet. 19:423–462; Botstein & Shortle (1985) "Strategies and applications of in vitro mutagenesis" Science 229:1193–1201; Carter (1986) "Site-directed mutagenesis" Biochem. J. 237:1–7; and Kunkel (1987) "The efficiency of oligonucleotide directed mutagenesis" in Nucleic Acids & Molecular Biology (Eckstein, F. and Lilley, D. M. J. eds., Springer Verlag, Berlin)); mutagenesis using uracil containing templates (Kunkel (1985) "Rapid and efficient site-specific mutagenesis without phenotypic selection" Proc. Natl. Acad. Sci. USA 82:488–492; Kunkel et al. (1987) "Rapid and efficient site-specific mutagenesis without phenotypic selection" Methods in Enzymol. 154, 367–382; and Bass et al. (1988) "Mutant Trp repressors with new DNA-binding specificities" Science 242:240–245); oligonucleotide-directed mutagenesis (Methods in Enzymol. 100: 468–500 (1983); Methods in Enzymol. 154: 329–350 (1987); Zoller & Smith (1982) "Oligonucleotide-directed mutagenesis using M13-derived vectors: an efficient and general procedure for the production of point mutations in any DNA fragment" Nucleic Acids Res. 10:6487–6500; Zoller & Smith (1983) "Oligonucleotide-directed mutagenesis of DNA fragments cloned into M13 vectors" Methods in Enzymol. 100:468–500; and Zoller & Smith (1987) "Oligonucleotide-directed mutagenesis: a simple method using two oligonucleotide primers and a single-stranded DNA template" Methods in Enzymol. 154: 329–350); phosphorothioate-modified DNA mutagenesis (Taylor et al. (1985) "The use of phosphorothioate-modified DNA in restriction enzyme reactions to prepare nicked DNA" Nucl. Acids Res. 13: 8749–8764; Taylor et al. (1985) "The rapid generation of oligonucleotide-directed mutations at high frequency using phosphorothioate-modified DNA" Nucl. Acids Res. 13: 8765–8787 (1985); Nakamaye & Eckstein (1986) "Inhibition of restriction endonuclease Nci I cleavage by phosphorothioate groups and its application to oligonucleotide-directed mutagenesis" Nucl. Acids Res. 14: 9679–9698; Sayers et al. (1988) "Y-T Exonucleases in phosphorothioate-based oligonucleotide-directed mutagenesis" Nucl. Acids Res. 16:791–802; and Sayers et al. (1988) "Strand specific cleavage of phosphorothioate-containing DNA by reaction with restriction endonucleases in the presence of ethidium bromide" Nucl. Acids Res. 16: 803–814); mutagenesis using gapped duplex DNA (Kramer et al. (1984) "The gapped duplex DNA approach to oligo-nucleotide-directed mutation construction" Nucl. Acids Res. 12: 9441–9456; Kramer & Fritz (1987) Methods in Enzymol. "Oligonucleotide-directed construction of mutations via gapped duplex DNA" 154:350–367; Kramer et al. (1988) "Improved enzymatic in vitro reactions in the gapped duplex DNA approach to oligonucleotide-directed construction of mutations" Nucl. Acids Res. 16: 7207; and Fritz et al. (1988) "Oligonucleotide-directed construction of mutations:

a gapped duplex DNA procedure without enzymatic reactions in vitro" Nucl. Acids Res. 16: 6987–6999).

CMV promoter/enhancer variants produced using one or more of the methods herein, or otherwise available to one of skill, can be selected or screened to determine whether the variation(s) confer one or more desirable properties. This can include identifying any activity that can be detected, for example, in an automated or automatable format, by any of the assays in the art. In preferred embodiments, CMV promoter/enhancer variants are screened in one or more of the in vitro or in vivo assays described in the Examples. Thus, variants can be operably linked to a conveniently measured marker gene to form an expression cassette. Expression of the marker gene can be detected, e.g., by FACS sorting to select for a desired level of expression. Additional testing can be carried out in vivo or in vitro to further characterize the variants and to identify those have desired properties. A variety of related (or even unrelated) properties can be evaluated, in serial or in parallel, at the discretion of the practitioner.

The above-described diversity generating and/or mutational methods can generate a plurality of different CMV promoter/enhancer variants. Accordingly, the invention provides compositions comprising at least two different nucleic acids of the invention. Collections of different nucleic acids are typically termed polynucleotide libraries, and such libraries are within the scope of the invention, regardless of whether the nucleic acids are present together in a composition or stored separately, e.g., in separate bacterial colonies, separate vials of purified DNA, etc.

The nucleic acids of the invention can provide a range of different expression levels of an operably linked transgene. Thus, in one embodiment, the nucleic acid includes a polynucleotide sequence that promotes the expression of an operably linked transgene at a level that is higher than the highest expression level of the same transgene when operably linked to a nucleic acid sequence corresponding to a human CMV promoter polynucleotide sequence. In an alternative embodiment, the nucleic acid includes a polynucleotide sequence that promotes the expression of an operably linked transgene at a level that is lower than the lowest expression level of the same transgene when operably linked to a nucleic acid sequence corresponding to a human CMV promoter polynucleotide sequence. The differences in expression level for nucleic acids of the invention, as compared to human CMV promoter sequences can be on the order of about 1.5-fold, 2-fold, 5-fold, or 10-fold or greater.

The nucleic acids of the invention, including those specifically exemplified herein (e.g., SEQ ID NOS:1–18) and fragments and variants thereof can all be produced and used as described below. Thus, persons of skill in the art appreciate that references herein to "chimeric CMV promoter/enhancers" or "recombinant promoters" apply generally to all of the nucleic acids of the invention (including fragment or variants) unless context dictates otherwise.

2. Production of Nucleic Acids

Nucleic acids of the invention can be prepared any of a variety of methods well known to those of skill in the art. For example, nucleic acids can be prepared by standard solid-phase methods, according to standard synthetic methods. Typically, fragments of up to about 100 bases are individually synthesized, then joined (e.g., by enzymatic or chemical ligation methods, or polymerase mediated recombination methods) to form essentially any desired continuous sequence. For example, the nucleic acids of the invention can be prepared by chemical synthesis using, e.g., the classical phosphoramidite method described by Beaucage et al., (1981) Tetrahedron Letters 22:1859–69, or the method described by Matthes et al., (1984) EMBO J. 3: 801–05., e.g., as is typically practiced in automated synthetic methods. According to the phosphoramidite method, oligonucleotides are synthesized, e.g., in an automatic DNA synthesizer, purified, annealed, ligated and cloned in appropriate vectors.

In addition, essentially any nucleic acid can be custom ordered from any of a variety of commercial sources, such as The Midland Certified Reagent Company (mcrc@oligos.com), The Great American Gene Company (http://www.genco.com), ExpressGen Inc. (www.expressgen.com), Operon Technologies Inc. (Alameda, Calif.) and many others.

In some applications, it is advantageous to stabilize the nucleic acid molecules described herein or to produce nucleic acid molecules that are modified to better adapt them for particular applications. To this end, the nucleic acid molecules of the invention can contain phosphorothioates, phosphotriesters, methyl phosphonates, short chain alkyl or cycloalkyl intersugar linkages or short chain heteroatomic or heterocyclic intersugar ("backbone") linkages. Most preferred are phosphorothioates and those with CH2—NH-O—CH2, CH2-N(CH3)—O—CH2 (known as the methylene (methylimino) or MMI backbone) and CH2-O—N(CH3)—CH2, CH2-N(CH3)—N(CH3)—CH2, and O—N(CH3)—CH2-CH backbones (where phosphodiester is O—P—O—CH2). Also preferred are nucleic acid molecules having morpholino backbone structures. Summerton, J. E. and Weller, D. D., U.S. Pat. No. 5,034,506. Other preferred embodiments use a protein-nucleic acid or peptide-nucleic acid (PNA) backbone, wherein the phosphodiester backbone of the nucleic acid molecule is replaced with a polyamide backbone, the bases being bound directly or indirectly to the aza nitrogen atoms of the polyamide backbone. P. E. Nielsen, M. Egholm, R. H. Berg, O. Buchardt, Science 1991, 254, 1497. Nucleic acid molecules of the invention can contain alkyl and halogen-substituted sugar moieties and/or can have sugar mimetics such as cyclobutyls in place of the pentofuranosyl group. In other preferred embodiments, the nucleic acid molecules can include at least one modified base form or "universal base" such as inosine. Nucleic acid molecules can, if desired, include an RNA cleaving group, a cholesteryl group, a reporter group, an intercalator, a group for improving the pharmacokinetic properties of the nucleic acid molecule, and/or a group for improving the pharmacodynamic properties of the nucleic acid molecule.

3. Nucleic Acid Compositions

The invention also contemplates standard manipulations of the nucleic acids of the invention and therefore includes compositions that represent the intermediates or end-products of standard recombinant DNA techniques. Thus, for example, the invention includes a composition produced by the cleaving of one or more the nucleic acids, e.g., by mechanical, chemical, or enzymatic means. Examples of enzymes suitable for enzymatic cleavage include a restriction endonuclease, an RNAse or a DNAse, and the like. The invention also includes a composition produced by a process comprising incubating one or more of the nucleic acids in the presence of deoxyribonucleotide triphosphates and a nucleic acid polymerase.

In an exemplary embodiment, the nucleic acid polymerase is a thermostable polymerase, such as those useful in amplification methods. Examples of in vitro amplification methods, including the polymerase chain reaction (PCR) the ligase chain reaction (LCR), Qβ-replicase amplification and other RNA polymerase mediated techniques are found in Berger, Sambrook, and Ausubel, as well as Mullis et al. (1987) U.S. Pat. No. 4,683,202; *PCR Protocols A Guide to Methods and Applications* (Innis et al. eds.) Academic Press Inc., San Diego, Calif. (1990) (Innis); Arnheim & Levinson (Oct. 1, 1990) C&EN 36–47; *The Journal Of NIH Research* (1991) 3:81–94; (Kwoh et al. (1989) *Proc. Natl Acad. Sci. USA* 86:1173; Guatelli et al. (1990) *Proc. Natl Acad. Sci. USA* 87:1874; Lomell et al. (1989) *J. Clin. Chem.* 35:1826; Landegren et al. (1988) *Science* 241:1077–1080; Van Brunt (1990) *Biotechnology* 8:291–294; Wu and Wallace (1989) *Gene* 4:560; and Barringer et al. (1990) Gene 89:117. Improved methods of cloning in vitro amplified nucleic acids are described in Wallace et al., U.S. Pat. No. 5,426, 039.

4. Expression Cassettes

The invention provides expression cassettes in which a chimeric promoter/enhancer polynucleotide sequence or fragment or variant of the invention is typically situated adjacent to one or more restriction sites at which one can insert a nucleic acid (i.e., a transgene) to be expressed. The expression cassettes of the invention optionally include transcription termination signals. Additional factors necessary or helpful in effecting expression may also be used as described herein. For example, an expression cassette can also include nucleotide sequences that encode a signal sequence that directs secretion of an expressed protein from the host cell.

The chimeric promoter/enhancer polynucleotide sequences, or fragments or variants thereof is joined to nucleic acids that are to be expressed (e.g., coding regions for polypeptides, tRNA and rRNA molecules, antisense nucleic acids, and the like), using techniques that are known to those of skill in the art. Suitable nucleic acids can encode a protein from any organism, e.g., a viral, bacterial, eukaryotic, mammalian, or human protein. Viral proteins of interest include those from dengue virus, human immunodeficiency virus (HIV), Japanese encephalitis virus, Venezuelan encephalitis virus. Examples of nucleic acids that can be incorporated into an expression cassette of the invention include a nucleic acid encoding: an immunogen; an immunomodulatory molecule, such as a co-stimulatory molecule (e.g., B7-1, B7-2, or other potypeptide that binds or associates with a CD28 and/or CTLA-4 receptor); an antigen (e.g., a cancer antigen, such as EpCam/KSA; hepatitis B surface antigen or fragment thereof; antigens from hepatitis A, hepatitis C, etc.), including a multivalent or cross-reactive antigen; an adjuvant; an allergen, an antibody; a bacterial toxin, including, e.g, staph/strep enterotoxin and CT/LT (choleratoxin, labile enterotoxin); a cytokine or cytokine receptor (e.g., IL-10 antagonist or receptor); and a prophylactic or therapeutic polypeptide. Other exemplary nucleic acids that can be included in the expression cassettes of the invention include those encoding any of a variety proteins described in commonly assigned PCT Application No. US99/03022 (WO 99/41369), entitled "Genetic Vaccine Vector Engineering," filed Feb. 10, 1999 (106.310WO); commonly assigned PCT Application No. US99/03020 (WO 99/41368), entitled "Optimization of Immunomodulatory Properties of Genetic Vaccines," filed on Feb. 10, 1999 (155.110WO); commonly assigned PCT Application No. US99/03023 (WO 99/41402), entitled "Targeting of Genetic Vaccine Vectors," filed on Feb. 10, 1999 (156.110WO); commonly assigned PCT Application No. US99/02944 (WO 99/41383), entitled "Antigen Library Immunization," filed on Feb. 10, 1999 (157.110WO); commonly assigned PCT Application No. US97/17302 (WO 98/13485), entitled "Methods for Optimization of Gene Therapy by Recursive Sequence Shuffling and Selection," filed Sep. 26, 1997 (107.410WO); commonly assigned PCT Application No. US00/16984 (WO 00/00234), entitled "Methods and Compositions for Engineering of Attenuated Vaccines," filed Jun. 20, 2000 (133.110WO); each of which is incorporated herein by reference in its entirety for all purposes.

A wide variety of cloning and in vitro amplification methods suitable for the construction of recombinant nucleic acids such as expression vectors are well-known to persons of ordinary skill in the art. Examples of these techniques and instructions sufficient to direct persons of skill through many cloning exercises are found in Berger and Kimmel, *Guide to Molecular Cloning Techniques, Methods in Enzymology* volume 152 Academic Press, Inc., San Diego, Calif. (Berger); and *Current Protocols in Molecular Biology*, F. M. Ausubel et al., eds., Current Protocols, a joint venture between Greene Publishing Associates, Inc. and John Wiley & Sons, Inc., (2000 Supplement) (Ausubel).

C. Vectors and Cells

The chimeric promoter/enhancers of the invention are useful for the production of proteins from eukaryotic, particularly mammalian, cell culture. As described above, the promoter/enhancers are operably linked to a coding region for the polypeptide of interest to form an expression cassette, which is introduced into an expression vector. This construct is then introduced into the cells to be used for production. Alternatively, the nucleic acids of the invention can be introduced into a vector in the absence an expression cassette. Such constructs are useful, for example, for propagating nucleic acids of the invention as an alternative to the synthetic methods described above.

In both types of constructs, the vector can, for example, be a plasmid, a cosmid, a phage, a virus or fragment thereof, a bacterial artificial chromosome (BAC), a yeast artificial chromosome (YAC). Large numbers of suitable vectors and promoters are known to those of skill in the art, and are commercially available.

General texts which describe molecular biological techniques useful herein, including the use of vectors, promoters and many other relevant topics, include Berger and Kimmel, Guide to Molecular Cloning Techniques, Methods in Enzymology volume 152 Academic Press, Inc., San Diego, Calif. (Berger); Sambrook et al., Molecular Cloning—A Laboratory Manual (2nd Ed.), Vol. 1–3, Cold Spring Harbor Laboratory, Cold Spring Harbor, N.Y., 1989 ("Sambrook") and Current Protocols in Molecular Biology, Ausubel et al., eds., Current Protocols, a joint venture between Greene Publishing Associates, Inc. and John Wiley & Sons, Inc., (supplemented through 2000) ("Ausubel")).

Once the chimeric promoter/enhancer of the invention is inserted into a vector, the construct is introduced into the host cells. Suitable host cells for expression of the recombinant polypeptides are known to those of skill in the art, and include, for example, eukaryotic cells including insect, mammalian and fungal cells. In a preferred embodiment, *Aspergillus niger* is used as the host cell. Transformation and infection methods for mammalian and other cells are described in Berger and Ausubel, supra. In some embodiments it is advantageous to introduce a polynucleotide library of the invention into a population of host cells, e.g., for propagation or expression and, optionally, screening an/or selection of constructs for desired properties.

D. Recombinant Protein Production

In one embodiment, a population of cells comprising a nucleic acid of the invention operably linked to a transgene encoding a polypeptide is used for recombinant protein production. Thus, the chimeric promoter/enhancers of the invention or fragments or variants thereof can be used to express a transgene in any application in which expression of the encoded polypeptide is desired. Examples include research applications, e.g., where the polypeptide is expressed in functional studies; any application, including in vitro or in vivo research or diagnostic assays, in which expression of a marker polypeptide is desired. In vivo applications, including gene therapy and genetic vaccination are discussed in greater detail below. The nucleic acids of the invention can also be used to produce any polypeptide of interest for research, medical, or industrial use.

When it is desirable to isolate the polypeptide, the polypeptide can be expressed in at least the subset of the population of cells or progeny thereof, which are usually in culture. Preferably the cells are cultured in a nutrient medium under conditions in which the nucleic acid promotes expression of the polypeptide. The culture conditions, such as temperature, pH and the like, are those previously used with the host cell selected for expression, and will be apparent to those skilled in the art and in the references cited herein, including, e.g., Freshney (1994) *Culture of Animal Cells, a Manual of Basic Technique*, third edition, Wiley-Liss, New York and the references cited therein.

Any of a number of well-known techniques for large- or small-scale production of proteins can be employed in expressing the polypeptides of the invention. These include, but are not limited to, the use of a shaken flask, a fluidized bed bioreactor, a roller bottle culture system, and a stirred tank bioreactor system. Cell culture can be carried out in a batch, fed-batch, or continuous mode.

After sufficient polypeptide has been expressed, the polypeptide is generally isolated or recovered from the cells or from the nutrient medium. Methods for isolation or recovery of recombinant proteins produced as described above are well-known and vary depending on the expression system employed. A polypeptide including a signal sequence can be recovered from the culture medium or the periplasm. Polypeptides can also be expressed intracellularly and recovered from cell lysates.

The expressed polypeptides can be purified from culture medium or a cell lysate by any method capable of separating the polypeptide from one or more components of the host cell or culture medium. Typically, the polypeptide is separated from host cell and/or culture medium components that would interfere with the intended use of the polypeptide. As a first step, the culture medium or cell lysate is usually centrifuged or filtered to remove cellular debris. The supernatant is then typically concentrated or diluted to a desired volume or diafiltered into a suitable buffer to condition the preparation for further purification.

The polypeptide can then be further purified using well-known techniques. The technique chosen will vary depending on the properties of the expressed polypeptide.

If, for example, the polypeptide is expressed as a fusion protein containing an affinity domain, purification typically includes the use of an affinity column containing the cognate binding partner. For instance, polypeptides fused with hexahistidine or similar metal affinity tags can be purified by fractionation on an immobilized metal affinity column.

One of skill in the art would recognize that after biological expression, or purification, the polypeptides may possess a conformation substantially different than the native conformations of the constituent polypeptides. In this case, it may be necessary to denature and reduce the polypeptide and then to cause the polypeptide to re-fold into the preferred conformation. Methods of reducing and denaturing proteins and inducing re-folding are well known to those of skill in the art (See, Debinski et al. (1993) *J. Biol. Chem.*, 268: 14065–14070; Kreitman and Pastan (1993) *Bioconjug. Chem.*, 4:581–585; and Buchner, et al., (1992) *Anal. Biochem.*, 205:263–270). Debinski et al., for example, describe the denaturation and reduction of inclusion body proteins in guanidine-DTE. The protein is then refolded in a redox buffer containing oxidized glutathione and L-arginine.

In an alternative embodiment, cells comprising a nucleic acid of the invention operably linked to a transgene encoding a polypeptide are in vivo. For example, the nucleic acids of the invention can be used to produce transgenic organisms that express the encoded polypeptide in a tissues or byproduct, including a bodily fluid, such as urine or milk. Any transgenic organism of interest, in which the polypeptide is expressed for production, research, or other purposes can be produced using conventional techniques. Transgenic mammal are of particular interest and are readily produced from mammalian cells selected, e.g., from fertilized oocytes, embryonic stem cells, or pluripotent stem cells. When the transgenic organism is used for protein production, the expressed polypeptide is recovered from the transgenic organism or byproduct and can optionally be isolation using standard protein purification methods, including those described above.

E. Gene Therapy and Genetic Vaccination

In some embodiments, the promoter/enhancers of the invention are used for gene therapy. For such applications, the promoter/enhancers can be operably linked to a gene that is to be expressed upon introduction into a cell. Broadly speaking, a gene therapy vector is an exogenous polynucleotide which produces a medically useful phenotypic effect upon the mammalian cell(s) into which it is transferred. The chimeric promoter/enhancers of the invention are also useful for use in genetic vaccination. For example, the chimeric promoter/enhancers can be used to obtain expression of an immunogenic polypeptide that is operably linked to the promoter/enhancer. In such applications, a suitable nucleic acid or vector of the invention can be introduced into cells in culture, followed by introduction of the cells are subsequently into the subject, i.e., ex vivo administration of the nucleic acid or vector. Alternatively, the nucleic acid or vector can be introduced into the cells of the subject by administering the nucleic acid or vector directly to the subject. The choice of vector (if used), formulation of the nucleic acid or vector, and mode of administration will vary depending on the particular application.

1. Vectors

Vectors used in gene therapy and genetic vaccination can be viral or nonviral. A vector may or may not have an origin of replication. For example, it is useful to include an origin of replication in a vector for propagation of the vector prior to administration to a patient. However, the origin of replication can often be removed before administration if the vector is designed to integrate into host chromosomal DNA or bind to host mRNA or DNA. Viral vectors are usually introduced into a patient as components of a virus. Illustrative vectors include, for example, adenovirus-based vectors (Cantwell (1996) *Blood* 88:4676–4683; Ohashi (1997) *Proc Natl Acad Sci USA* 94:1287–1292), Epstein-Barr virus-based vectors (Mazda (1997) *J Immunol Methods* 204: 143–151), adenovirus-associated virus vectors, Sindbis virus vectors (Strong (1997) Gene Ther 4:624–627), herpes simplex virus vectors (Kennedy (1997) *Brain* 120:1245–1259) and retroviral vectors (Schubert (1997) *Curr Eye Res* 16:656–662).

Nonviral vectors, typically dsDNA, can be transferred as naked DNA or associated with a transfer-enhancing vehicle, such as a receptor-recognition protein, liposome, lipoamine, or cationic lipid. This DNA can be transferred into a cell using a variety of techniques well known in the art. For example, naked DNA can be delivered by the use of liposomes which fuse with the cellular membrane or are endocytosed, i.e., by employing ligands attached to the liposome, or attached directly to the DNA, that bind to surface membrane protein receptors of the cell resulting in endocytosis. Alternatively, the cells may be permeabilized to enhance transport of the DNA into the cell, without injuring the host cells. One can use a DNA binding protein, e.g., HBGF-1, known to transport DNA into a cell. These procedures for delivering naked DNA to cells are useful in vivo. For example, by using liposomes, particularly where the liposome surface carries ligands specific for target cells, or are otherwise preferentially directed to a specific organ, one may provide for the introduction of the DNA into the target cells/organs in vivo.

The chimeric promoter/enhancers of the invention can also be used for gene therapy in the absence of a vector. The DNA segments that include the chimeric promoter/enhancer can be introduced into cells using a system which targets the segments to the particular gene that is to be expressed using the promoter/enhancer. Suitable targeting technology is described in, for example, U.S. Pat. No. 6,054,288.

In some embodiments, the optimized recombinant promoters of the invention are used in conjunction with a vector, including, for example, an expression vector or genetic vaccine vector. The choice of vector and each of its components, including, e.g., the one or more recombinant promoters employed in the vector, one or more antigens, and/or one or more co-stimulatory sequences, and the like, can be optimized for the particular purpose of treating one or more specific conditions, including, for example, allergy, cancer, or other conditions. The choice of a chimeric promoter/enhancer for a particular vector format can be based on a particular functional activity, such as the degree of expression desired of a vector component (e.g., a high-, low-, or intermediate-activity promoter), the type of tissue in which the promoter is to operate (tissue-specific promoter), or a cell-specific regulated promoter that optimally drives transcription in a desired cell type(s). In each instance, the promoter can be optimized using recursive sequence recombination and selection methods analogous to those described herein.

Vectors of the present invention comprising at least one recombinant promoter of the present invention can be designed to include one or more nucleic acid sequences that express one or more modulators, immunomodulators, or immunostimulatory molecules. Optimized immunomodulators, immunostimulatory molecules and methods for obtaining optimized immunomodulators and immunostimulatory molecules are described in commonly assigned PCT Application No. US99/03020 (WO 99/41368), entitled "Optimization of Immunomodulatory Properties of Genetic Vaccines," and copending, commonly assigned U.S. patent application Ser. No. 09/888,324, entitled "Novel Co-Stimulatory Molecules" filed on Jun. 21, 2001 as LJAQ, each of which is incorporated herein by reference in its entirety for all purposes. These optimized immunomodulatory or immunostimulatory sequences are particularly suitable for use as components of the multicomponent genetic vaccines of the invention. Multiple modulators can be expressed from a monocistronic or multicistronic form of the vector. One or more vectors comprising optimized promoters of the invention can be used in conjunction with or as multicomponent genetic vaccines, which are capable of tailoring an immune response as is most appropriate to achieve a desired effect (see, e.g., commonly assigned PCT Application No. PCT/US99/03022 (WO 99/41369), entitled "Genetic Vaccine Vector Engineering," which is incorporated herein by reference in its entirety for all purposes).

The vectors comprising recombinant promoters of the invention can also be engineered to direct maximal synthesis and release of one or more chemokines from the target cells, e.g., in a desired ratio. Genetic vaccine components, and methods for obtaining components, that provide optimal release of chemokines are described in PCT Application No. US99/03020 (WO 99/41368).

The recombinant optimized promoters of the invention can also be used in conjunction with optimized antigens. Types of wild-type antigens that can be employed for various conditions and for use in genetic vaccines are described in commonly assisted PCT Application No. PCT/US99/02944 (WO 99/41383), entitled "Antigen Library Immunization," which is incorporated herein by reference in its entirety for all purposes. Furthermore, multiple antigens can be expressed from a monocistronic or multicistronic form of the vector comprising at least one recombinant promoter of the invention. Moreover, an antigen for a particular condition can be optimized using recombination and selection methods analogous to those described herein. Such methods, and antigens appropriate for various conditions, are described in PCT Application No. PCT/US99/02944.

A vector engineered to direct a $T_H1$ response is preferred for many of the immune responses mediated by the antigens described herein (see, e.g., PCT Application No. PCT/US99/03022). It is sometimes advantageous to employ a genetic vaccine that is targeted for a particular target cell type (e.g., an antigen presenting cell or an antigen processing cell). Vector components for targeting genetic vaccine vectors to particular cell types, and methods of obtaining improved targeting, are described in commonly assigned PCT Application No. US99/03023 (WO 99/41402), entitled "Targeting of Vaccine Vectors," which is incorporated herein by reference in its entirety for all purposes.

Genetic vaccines which include optimized vector modules, including optimized promoters of the invention are useful for treating many diseases and other conditions that are either mediated by a mammalian immune system or are susceptible to treatment by an appropriate immune response. Representative examples of these diseases are listed in PCT Appn. No. US 99/03022 (WO 99/41369). Antigens appropriate for each are described in PCT Application No. PCT/US99/02944 (WO 99/41383). Examples of genetic vaccines within the scope of the invention include: prophylactic vaccines for infectious diseases, including HIV, dengue, and HBV; therapeutic vaccines for infectious diseases such as HBV, HIV, and other major chronic infectious disease targets; therapeutic cancer vaccines; therapeutic allergy vaccines; therapeutic vaccines for autoimmune disease; vaccines that express, e.g., novel immunomodulatory proteins that can be used to augment the immune response as adjuvants or vaccine components. A preferred genetic vaccine includes an expression vector including a recombinant promoter of the invention that expresses both a co-stimulatory molecule, such as, e.g., a CD28-binding protein, and an antigen, such as a cancer antigen.

2. Pharmaceutical Compositions and Methods of Administration

Gene therapy and genetic vaccine vectors are useful for treating and/or preventing various diseases and other conditions. The following discussion focuses on the on the use of vectors because gene therapy and genetic vaccine method typically employ vectors, but persons of skill in the art appreciate that the nucleic acids of the invention can, depending on the particular application, be employed in the absence of vector sequences. Accordingly, references in the following discussion to vectors should be understood as also relating to nucleic acids of the invention that lack vector sequences.

Vectors can be delivered to a subject to induce an immune response or other therapeutic or prophylactic response. Suitable subjects include, but are not limited to, a mammal, including, e.g., a human, primate, monkey, orangutan, baboon, mouse, pig, cow, cat, goat, rabbit, rat, guinea pig, hamster, horse, sheep; or a non-mammalian vertebrate such as a bird (e.g., a chicken or duck) or a fish, or invertebrate.

Vectors can be delivered in vivo by administration to an individual patient, typically by local (direct) administration or by systemic administration (e.g., intravenous, intraperitoneal, intramuscular, subdermal, intracranial, anal, vaginal, oral, buccal route or they can be inhaled) or they can be administered by topical application. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

In local (direct) administration formats, the nucleic acid or vector is typically administered or transferred directly to the cells to be treated or to the tissue site of interest (e.g., tumor cells, tumor tissue sample, organ cells, blood cells, cells of the skin, lung, heart, muscle, brain, mucosae, liver, intestine, spleen, stomach, lymphatic system, cervix, vagina, prostate, mouth, tongue, etc.) by any of a variety of formats, including topical administration, injection (e.g., by using a needle or syringe), or vaccine or gene gun delivery, pushing into a tissue, organ, or skin site. For standard gene gun administration, the vector or nucleic acid of interest is precipitated onto the surface of microscopic metal beads. The microprojectiles are accelerated with a shock wave or expanding helium gas, and penetrate tissues to a depth of several cell layers. For example, the AccelTM Gene Delivery Device manufactured by Agacetus, Inc. Middleton Wis. is suitable for use in this embodiment. The nucleic acid or vector can be delivered, for example, intramuscularly, intradermally, subdermally, subcutaneously, orally, intraperitoneally, intrathecally, intravenously, or placed within a cavity of the body (including, e.g., during surgery), or by inhalation or vaginal or rectal administration.

In in vivo indirect contact/administration formats, the nucleic acid or vector is typically administered or transferred indirectly to the cells to be treated or to the tissue site of interest, including those described above (such as, e.g., skin cells, organ systems, lymphatic system, or blood cell system, etc.), by contacting or administering the nucleic acid or vector of the invention directly to one or more cells or population of cells from which treatment can be facilitated. For example, tumor cells within the body of the subject can be treated by contacting cells of the blood or lymphatic system, skin, or an organ with a sufficient amount of the polypeptide such that delivery of the nucleic acid or vector to the site of interest (e.g., tissue, organ, or cells of interest or blood or lymphatic system within the body) occurs and effective prophylactic or therapeutic treatment results. Such contact, administration, or transfer is typically made by using one or more of the routes or modes of administration described above.

A large number of delivery methods are well known to those of skill in the art. Such methods include, for example liposome-based gene delivery (Debs and Zhu (1993) WO 93/24640; Mannino and Gould-Fogerite (1988) *BioTechniques* 6(7):682–691; Rose U.S. Pat No. 5,279,833; Brigham (1991) WO 91/06309; and Felgner et al. (1987) *Proc. Natl Acad. Sci. USA* 84:7413–7414), as well as use of viral vectors (e.g., adenoviral (see, e.g., Berns et al. (1995) *Ann. NY Acad. Sci.* 772:95–104; Ali et al. (1994) *Gene Ther.* 1:367–384; and Haddada et al. (1995) *Curr. Top. Microbiol. Immunol.* 199 (Pt 3):297–306 for review), papillomaviral, retroviral (see, e.g., Buchscher et al. (1992) *J. Virol.* 66(5) 2731–2739; Johann et al. (1992) *J. Virol.* 66 (5):1635–1640 (1992); Sommerfelt et al., (1990) *Virol.* 176:58–59; Wilson et al. (1989) *J. Virol.* 63:2374–2378; Miller et al., *J. Virol.* 65:2220–2224 (1991); Wong-Staal et al., PCT/US94/05700, and Rosenburg and Fauci (1993) in *Fundamental Immunology, Third Edition* Paul (ed) Raven Press, Ltd., New York and the references therein, and Yu et al., *Gene Therapy* (1994) supra.), and adeno-associated viral vectors (see, West et al. (1987) *Virology* 160:38–47; Carter et al. (1989) U.S. Pat. No. 4,797,368; Carter et al. WO 93/24641 (1993); Kotin (1994) *Human Gene Therapy* 5:793–801; Muzyczka (1994) *J. Clin. Invst.* 94:1351 and Samulski (supra) for an overview of AAV vectors; see also, Lebkowski, U.S. Pat. No. 5,173,414; Tratschin et al. (1985) *Mol. Cell. Biol.* 5(11):3251–3260; Tratschin, et al. (1984) *Mol. Cell. Biol.*, 4:2072–2081; Hermonat and Muzyczka (1984) *Proc. Natl Acad. Sci. USA,* 81:6466–6470; McLaughlin et al. (1988) and Samulski et al. (1989) *J. Virol.,* 63:03822–3828), and the like.

"Naked" DNA and/or RNA that comprises a genetic vaccine can be introduced directly into a tissue, such as muscle, by injection using a needle or other similar device. See, e.g., U.S. Pat. No. 5,580,859. Other methods such as "biolistic" or particle-mediated transformation (see, e.g., Sanford et al., U.S. Pat. Nos. 4,945,050; 5,036,006) are also suitable for introduction of genetic vaccines into cells of a mammal according to the invention. These methods are useful not only for in vivo introduction of DNA into a subject, such as a mammal, but also for ex vivo modification of cells for reintroduction into a mammal. DNA is conveniently introduced directly into the cells of a mammal or other subject using, e.g., injection, such as via a needle, or a "gene gun." As for other methods of delivering genetic vaccines, if necessary, vaccine administration is repeated in order to maintain the desired level of immunomodulation, such as the level of T cell activation. Alternatively, nucleotides can be impressed into the skin of the subject.

Gene therapy and genetic vaccine vectors (e.g., adenoviruses, liposomes, papillomaviruses, retroviruses, etc.) can be administered directly to the subject (usually a mammal) for transduction of cells in vivo. The vectors can be formulated as pharmaceutical compositions for administration in any suitable manner, including parenteral (e.g., subcutaneous, intramuscular, intradermal, or intravenous), topical, oral, rectal, vaginal, intrathecal, buccal (e.g., sublingual), or local administration, such as by aerosol or transdermally, for immunotherapeutic or other prophylactic and/or therapeutic treatment. Pretreatment of skin, for example, by use of hair-removing agents, may be useful in transdermal delivery. Suitable methods of administering such packaged nucleic acids are available and well known to those of skill in the art, and, although more than one route can be used to administer a particular composition, a particular route can often provide a more immediate and more effective reaction than another route.

Pharmaceutical compositions of the invention can, but need not, include a pharmaceutically acceptable carrier. Pharmaceutically acceptable carriers are determined in part by the particular composition being administered, as well as by the particular method used to administer the composition. Accordingly, there are a wide variety of suitable formulations of pharmaceutical compositions of the present invention. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of gene therapy or genetic vaccine vector in these formulations can vary widely, and will be selected primarily based on fluid volumes, viscosities, body weight and the like in accordance with the particular mode of administration selected and the patient's needs.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, tragacanth, microcrystalline cellulose, acacia, gelatin, colloidal silicon dioxide, croscarmellose sodium, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, carriers known in the art. It is recognized that the gene therapy vectors and genetic vaccines, when administered orally, must be protected from digestion. This is typically accomplished either by complexing the vector with a composition to render it resistant to acidic and enzymatic hydrolysis or by packaging the vector in an appropriately resistant carrier such as a liposome. Means of protecting vectors from digestion are well known in the art. The pharmaceutical compositions can be encapsulated, e.g., in liposomes, or in a formulation that provides for slow release of the active ingredient.

The packaged nucleic acids, alone or in combination with other suitable components, can be made into aerosol formulations (e.g., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the packaged nucleic acid with a base, including, for example, liquid triglycerides, polyethylene glycols, and paraffin hydrocarbons.

Formulations suitable for parenteral administration, such as, for example, by intraarticular (in the joints), intravenous, intramuscular, intradermal, subdermal, intraperitoneal, and subcutaneous routes, include aqueous and non-aqueous, isotonic sterile injection solutions, which can contain one or more antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration and intravenous administration are the preferred methods of administration. The formulations of packaged nucleic acid can be presented in unit-dose or multi-dose sealed containers, such as ampoules and vials.

Injection solutions and suspensions can be prepared from sterile powders, granules, and tablets of the kind previously described. Cells transduced by the packaged nucleic acid can also be administered intravenously or parenterally.

The dose administered to a patient, in the context of the present invention should be sufficient to effect a beneficial effect, such as an immune or other prophylactic or therapeutic response in the patient over time. The dose will be determined by the efficacy of the particular vector employed and the condition of the patient, as well as the body weight or vascular surface area of the patient to be treated. The size of the dose also will be determined by the existence, nature, and extent of any adverse side-effects that accompany the administration of a particular vector, or transduced cell type in a particular patient.

In determining the effective amount of the vector to be administered in the treatment or prophylaxis of an infection or other condition, the physician evaluates vector toxicities, progression of the disease, and the production of anti-vector antibodies, if any. In general, the dose equivalent of a naked nucleic acid from a vector for a typical 70 kilogram patient can range from about 10 ng to about 1 g, about 100 ng to about 100 mg, about 1 µg to about 10 mg, about 10 µg to about 1 mg, or from about 30–300 µg. Doses of vectors used to deliver the nucleic acid are calculated to yield an equivalent amount of therapeutic nucleic acid. Administration can be accomplished via single or divided doses.

In therapeutic applications, compositions are administered to a patient suffering from a disease (e.g., an infectious disease or autoimmune disorder) in an amount sufficient to cure or at least partially arrest or ameliorate the disease or at least one of its complications. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of protein to effectively treat the patient.

In prophylactic applications, compositions are administered to a human or other mammal to induce an immune or other prophylactic response that can help protect against the establishment of an infectious disease or other condition.

The toxicity and therapeutic efficacy of the vectors that include chimeric promoter/enhancers provided by the invention are determined using standard pharmaceutical procedures in cell cultures or experimental animals. One can determine the $LD_{50}$ (the dose lethal to 50% of the population) and the $ED_{50}$ (the dose therapeutically effective in 50% of the population) using procedures presented herein and those otherwise known to those of skill in the art.

A typical pharmaceutical composition for intravenous administration would be about 0.1 to 10 mg per patient per day. Dosages from 0.1 up to about 100 mg per patient per day may be used, particularly when the drug is administered to a secluded site and not into the blood stream, such as into a body cavity or into a lumen of an organ. Substantially higher dosages are possible in topical administration. For recombinant promoters of the invention that express the linked transgene at high levels, it may be possible to achieve the desired effect using lower doses, e.g., on the order of about 1 μg or 10 μg per patient per day. Actual methods for preparing parenterally administrable compositions will be known or apparent to those skilled in the art and are described in more detail in such publications as *Remington's Pharmaceutical Science,* 15th ed., Mack Publishing Company, Easton, Pennsylvania (1980).

The vectors or nucleic acids that include the chimeric promoter/enhancers of the invention can be packaged in packs, dispenser devices, and kits for administering the vectors to a mammal. For example, packs or dispenser devices that contain one or more unit dosage forms are provided. Typically, instructions for administration of the compounds will be provided with the packaging, along with a suitable indication on the label that the compound is suitable for treatment of an indicated condition. For example, the label may state that the active compound within the packaging is useful for treating a particular infectious disease, autoimmune disorder, tumor, or for preventing or treating other diseases or conditions that are mediated by, or potentially susceptible to, a mammalian immune response.

F. Character Strings

The present invention provides computers, computer readable media and integrated systems comprising character strings corresponding to the sequence information herein for the nucleic acids herein.

Various methods and genetic algorithms (GOs) known in the art can be used to detect homology or similarity between different character strings, or can be used to perform other desirable functions such as to control output files, provide the basis for making presentations of information including the sequences and the like. Examples include BLAST, discussed supra. Extensive examples of the use of sequences in silico are found in, e.g., PCT/US00/01202 "METHODS FOR MAKING CHARACTER STRINGS, POLYNUCLEOTIDES AND POLYPEPTIDES HAVING DESIRED CHARACTERISTICS" by Selifonov et al., filed Jan. 18, 2000; PCT/US00/01230 "OLIGONUCLEOTIDE MEDIATED NUCLEIC ACID RECOMBINATION" by Crameri et al., filed Jan. 18, 2000; and PCT/US00/01138 "METHODS OF POPULATING DATA STRUCTURES FOR USE IN EVOLUTIONARY SIMULATIONS" by Selifonov and Stemmer, filed Jan. 18, 2000.

Thus, different types of homology and similarity of various stringency and length can be detected and recognized in the integrated systems herein. For example, many homology determination methods have been designed for comparative analysis of sequences of biopolymers, for spell-checking in word processing, and for data retrieval from various databases. With an understanding of double-helix pair-wise complement interactions among 4 principal nucleobases in natural polynucleotides, models that simulate annealing of complementary homologous polynucleotide strings can also be used as a foundation of sequence alignment or other operations typically performed on the character strings corresponding to the sequences herein (e.g., word-processing manipulations, construction of figures comprising sequence or subsequence character strings, output tables, etc.). An example of a software package with genetic algorithms for calculating sequence similarity is BLAST, which can be adapted to the present invention by inputting character strings corresponding to the sequences herein.

Similarly, standard desktop applications such as word processing software (e.g., Microsoft Word™ or Corel WordPerfect™) and database software (e.g., spreadsheet software such as Microsoft Excel™, Corel Quattro PrO™, or database programs such as Microsoft Access™ or Paradox™) can be adapted to the present invention by inputting a character string corresponding to the nucleic acids of the invention. For example, the integrated systems can include the foregoing software having the appropriate character string information, e.g., used in conjunction with a user interface (e.g., a GUI in a standard operating system such as a Windows, Macintosh or LINUX system) to manipulate strings of characters. As noted, specialized alignment programs such as BLAST can also be incorporated into the systems of the invention for alignment of nucleic acid (or corresponding character strings).

Integrated systems for analysis in the present invention typically include a digital computer with GO software for aligning sequences, as well as data sets entered into the software system comprising any of the sequences herein. The computer can be, e.g., a PC (Intel x86 or Pentium chip-compatible DOS™, OS2™ WINDOWS™ WINDOWS NT™, WINDOWS95™, WINDOWS98™ LINUX based machine, a MACINTOSH™, Power PC, or a UNIX based (e.g., SUN™ work station) machine) or other commercially common computer which is known to one of skill. Software for aligning or otherwise manipulating sequences is available, or can easily be constructed by one of skill using a standard programming language such as Visualbasic, Fortran, Basic, Java, or the like.

Any controller or computer optionally includes a monitor which is often a cathode ray tube ("CRT") display, a flat panel display (e.g., active matrix liquid crystal display, liquid crystal display), or others. Computer circuitry is often placed in a box which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard or mouse optionally provide for input from a user and for user selection of sequences to be compared or otherwise manipulated in the relevant computer system.

The computer typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing the operation of the fluid direction and transport controller to carry out the desired operation.

The software can also include output elements for controlling nucleic acid synthesis (e.g., based upon a sequence or an alignment of a sequence herein) or other operations which occur downstream from an alignment or other operation performed using a character string corresponding to a sequence herein.

In one embodiment, the invention provides an integrated system comprising a computer or computer readable medium comprising a database having one or more sequence records. Each of the sequence records comprises one or more character strings corresponding to a nucleic acid or polypeptide or protein sequence selected from SEQ ID NO:1 to SEQ ID NO:18 or a fragment or variant thereof. The integrated system further comprises a use input interface allowing a use to selectively view the one or more sequence records. In one such integrated system, the computer or computer readable medium comprises an alignment instruction set that aligns the character strings with one or more additional character strings corresponding to a nucleic acid or polypeptide or protein sequence.

One such integrated system includes an instruction set that comprises at least one of the following: a local sequence comparison or a local homology comparison determination, a sequence alignment or a homology alignment determination, a sequence identity or similarity search or a search for similarity determination, a sequence identity or similarity determination, a structural similarity search, a structure determination, a nucleic acid motif determination, a hypothetical translation, a determination of a restriction map, a sequence recombination and a BLAST determination. In some embodiments, the system further comprises a readable output element that displays an alignment produced by the alignment instruction set.

Methods of using a computer system to present information pertaining to at least one of a plurality of sequence records stored in a database are also provided. Each of the sequence records comprises at least one character string corresponding to SEQ ID NO:1 to SEQ ID NO:18 or a fragment or variant thereof. The method comprises determining at least one character string corresponding to one or more of these sequences or a subsequence thereof; determining which of the at least one character string of the list are selected by a user; and displaying each of the selected character strings, or aligning each of the selected character strings with an additional character string. The method may further comprise displaying an alignment of each of the selected character strings with an additional character string and/or displaying the list.

EXAMPLES

The following examples are offered to illustrate, but not to limit the present invention.

Materials and Methods
 CMV isolates

Four strains of cytomegalovirus (CMV) were obtained from American Type Culture Collection (ATCC) (Rockville, Md.). Human AD169 (VR-538; Rowe W. et al. (1956) *Proc. Soc. Exp. Biol. Med.* 92:418) and Human Towne (VR-977; Plotkin S A (1975) *Infect Immun.* 12:521–27) strains were isolated from human patients with CMV infections, while the 68-1 (Asher D M (1969) *Bacteriol. Proc.* 269:91) and CSG (Black H (1963) *Proc. Soc. Exp. Biol. Med.* 112:601) strains were isolated from Rhesus and Vervet monkeys, respectively.

Propagation of CMV Isolates in Culture

All CMV isolates were passaged by coculture with WI-38 cells, a human diploid fibroblast cell line also obtained from ATCC (CCL-75; Hayflick L and Moorhead PS (1961) *Exp. Cell Res.* 25:585–621). Fibroblast monolayers were infected with CMV isolates when they were ~80% confluent. Following adsorption for 1 hour at 37° C., DMEM with 5% FCS was added, and the cultures incubated at 37° C. Supernatants were collected when cell monolayers showed extensive cytopathic effect, and cleared of cell debris by centrifuging at 10 000×g for 10 min at 4° C. Clarified supernatants were stored at –80° C. until needed.

Purification of Viral DNA

Virus-containing supernatants were layered onto a sorbitol cushion (20% D-sorbitol, 50 mM Tris [pH 7.2], 1 mM $MgCl_2$) and centrifuged at 55 000×g for 1 hour to pellet the virus. Virions were resuspended in 2 mL of 50 mM Tris [pH 8.0]–1 mM $MgCl_2$, and an equal volume of lysis buffer (150 mM Tris [pH 8.0], 1 mM $MgCl_2$, 0.2 mM EDTA, 200 mM NaCl, 1% sodium sarkosyl, 200 µg proteinase K per mL) was added. The lysate was incubated at 37° C. for 3 to 5 hours. Liberated viral DNA was extracted four times by gently rocking with an equal volume of phenol and chloroform (1:1; vol:vol). The DNA was extracted twice more with chloroform and then precipitated with ethanol. The precipitate was washed with 80% ethanol, air dried briefly, and resuspended in TE (10 mM Tris [ph 8.0], 1 mM EDTA) overnight. Viral DNAs were stored at –20° C.

Amplification of CMV Promoter Sequences by PCR

CMV promoter sequences were amplified using the XL PCR kit (Promega, Madison, Wis.) according to the manufacturer's protocol. Primers used for amplifying the sequences included tails encoding EcoR1 or BamH1 sites, allowing the PCR product to be digested with these enzymes for cloning. The primers used were used to amplify promoter sequences from human and monkey CMVs:

Primers for promoters in Human CMV Strains Towne and AD169:

```
5'-ATA GCA CTG AGA CCT ATC GAA TTC ATA TGA GGC TAT ATC GCC GAT A-3'   (SEQ ID NO:24)

5'-TCA GTG AAC GCT TAT CTA GGA TCC AAG GAC GGT GAC TGC AGA AAA-3'     (SEQ ID NO:25)
```

Primers for Rhesus Monkey CMV Promoter:

```
5'-ATA GCA CTG AGA CCT ATC GAA TTC AAT GGC GAC TTG GCA TTG AGC CAA TT-3'   (SEQ ID NO:26)

5'-ATA GCA CTG AGA CCT ATC GAA TTC ACT TGG CAC GGT GCC AAG TTT-3'          (SEQ ID NO:27)

5'-TCA GTG AAC GCT TAT CTA GGA TCC TAT CCG CGT TCC AAT GCA CCC TT-3'       (SEQ ID NO:28)

5'-TCA GTG AAC GCT TAT CTA GGA TCC TAT CCG CAT TCC AAT GCA CCG T-3'        (SEQ ID NO:29)
```

For a description of the human CMV (hCMV) promoters, see, e.g., U.S. Pat. No. 5,385,839 and Meier, J., et al., *Intervirology* 39:331–342 (1996), the full disclosure of which is incorporated herein by reference in its entirety for all purposes. For cloning procedure for a hCMV and Rhesus CMV promoter, see. e.g., U.S. Pat. No. 5,385,839 and Alcendor et al., *Virology* 194:815–812 (1993), the full disclosure of each of which is incorporated herein by reference in its entirety for all purposes. The nucleotide sequences for human CMV promoters, Towne and AD169 strains, are shown in FIGS. 8A–8I. The sequence for human CMV promoter Towne strain is shown at GenBank Accession No. X03922. The nucleotide sequences for the Rhesus and Vervet monkey CMV promoters are shown in FIGS. 10A–10E. Rhesus CMV IE promoter is shown in Alcendor et al., *Virology* 194:815–812(1993). AGM CMV IE (Colburn strain) is shown at GenBank Accession No. M16019.

Building a Vector for Screening Novel Chimeric Promoter Sequences Resulting from Shuffling of CMV Promoter Sequences ("Chimeric Promoter Sequences")

The SRα promoter nucleic sequence (as described in Tackebe, Y. et al., *Molecular and Cellular Biol* 8:466–472 (1988)) was amplified by PCR from plasmid ARI1677 (for a description of this plasmid, see Whitehorn et al., Biotechnology 13:1215–1219 (1995), FIG. 1, termed "Alpha+KH/HPAP20") using the following two primers encoding Age1 restriction sites.

```
5'-ATA GCA CTG AGA CCTATC ACC GGT TGG TCC TGT AGT TTG CTA ACA CA-3'     (SEQ ID NO:30)

5'-TCA GTG AAC GCT TAT CTA ACC GGT TCG AGG CAG CTT GGA TCT GTA ACG-3'   (SEQ ID NO:31)
```

The resulting SRα promoter sequence fragment (~950 bp) was digested with Age 1, and cloned into the Age1 site of vector pEGFP-1 (Clontech; Palo Alto, Calif.) (enhanced green fluorescent protein). A clone with this SRα promoter sequence fragment in the forward orientation was revealed by restriction enzyme digestion. This plasmid was named pEGFP-1(SRα).

The monoclonal antibody 179 (mAb179) epitope nucleic acid sequence was amplified by PCR from plasmid ARI1677 using the following two primers encoding Age1 and BsrG1 restriction enzyme sites.

```
5'-ATT CTA CCA TGT CTC ACC GGT CGC CAC CAT GGC CTT ACC AGT GAG CGC CTT GC-3'   (SEQ ID NO:32)

5'-TCA CTA CCT AGT AGT TGT ACA GTA TCT TAT CAT GTC TGG ATC A-3'               (SEQ ID NO:33)
```

Following digestion with Age1 and BsrG1 restriction enzymes, the mAb179 epitope nucleic acid fragment was cloned into Clontech pEGFP-1 using Age1 and BsrG1 restriction sites, thereby removing the EGFP (enhanced green fluorescent protein) gene from the vector.

A fragment comprising the SRα promoter nucleic acid sequence, EGFP gene sequence, and BGH poly A nucleic acid sequence (the EGFP gene and BGH poly A sequences comprised part of the pEGFP-1 Clontech vector, discussed above) was amplified by PCR from plasmid pEGFP-1(SRα) using the following two primers encoding Eco47111 and Xho1 restriction enzyme sites.

```
5'-TGA GTG AAC GCT TAT CTA AGC GCT TTC TGT GGA ATG TGT GTC AGT TA-3'     (SEQ ID NO:34)

5'-ATA GCA CTG AGA CCT ATC CTC GAG TAC GCC TTA AGA TAC ATT GAT GA-3'     (SEQ ID NO:35)
```

This fragment was digested with Eco47111 and Xho1, and cloned into pEGFP-1 vector in which the EGFP gene was replaced with the mAb179 epitope sequence. This plasmid is now referred to as pmAb179/GFP(SRα), and was used for screening novel chimeric promoter sequences in vitro.

Shuffling CMV Promoter Sequences and Preparation of Plasmid Libraries

AD169, Rhesus, Towne, and Vervet monkey CMV promoter sequences were "shuffled" using DNA shuffling methods and recombination formats described by the present inventors and co-workers in co-pending applications Ser. No. PCT/US99/03022, filed Feb. 10, 1999, PCT/US95/02126, filed Feb. 17, 1995, Ser. No. PCT/US98/00852, filed Jan. 16, 1998, Serial No. PCT/US99/03020, filed Feb. 10, 1999, Serial No. PCT/US99/02944, filed Feb. 10, 1999, Ser. No. PCT/US99/03023, filed Feb. 10, 1999, Ser. No. PCT/US/97/24239, filed Dec. 17, 1997, U.S. Ser. No. 08/621,859, filed Mar. 25, 1996, U.S. Ser. No. 08/621,430, filed Mar. 25, 1996, U.S. Ser. No. 08/675,502, filed Jul. 3, 1996, Serial No. PCT/US96/05480, filed Apr. 18, 1996, U.S. Ser. No. 08/721,840, filed Sep. 27, 1996, Serial No. PCT/US97/17300, filed Sep. 26, 1997, and U.S. Pat. Nos. 5,605,793, 5,830,721, 5,811,238, 5,837,458, 5,834,252; and Stemmer, *Science* 270:1510 (1995); Stemmer et al., *Gene* 164:49–53 (1995); Stemmer, *Bio/Technology* 13:549–553 (1995); Stemmer, *Proc. Natl Acad. Sci. U.S.A.* 91:10747–10751 (1994); Stemmer, *Nature* 370:389–391 (1994); Crameri et al., *Nature Medicine* 2(1):1–3 (1996); Crameri et al. *Nature Biotechnology* 14:315–319 (1996), each of which is incorporated herein by reference in its entirety for all purposes. DNA shuffling is also sometimes referred to as molecular breeding directed molecular evolution (i.e., shuffling plus screening assays), evolution, or recursive sequence recombination.

Other methods for obtaining libraries of recombinant polynucleotides and/or for obtaining diversity in nucleic acids used as the substrates for shuffling include, for example, homologous recombination (PCT/US98/05223; Publ. No. WO98/42727); oligonucleotide-directed mutagenesis (for review see, Smith, *Ann. Rev. Genet.* 19:423–462 (1985); Botstein and Shortle, *Science* 229:1193–1201 (1985); Carter, *Biochem. J.* 237:1–7 (1986); Kunkel, "The efficiency of oligonucleotide directed mutagenesis" in *Nucleic acids & Molecular Biology,* Eckstein and Lilley, eds., Springer Verlag, Berlin (1987)). Included among these methods are oligonucleotide-directed mutagenesis (Zoller and Smith, *Nucl. Acids Res.* 10:6487–6500 (1982), *Methods in Enzymol.* 100:468–500 (1983), and *Methods in Enzymol.* 154:329–350 (1987)) phosphothioate-modified DNA mutagenesis (Taylor et al., *Nucl. Acids Res.* 13:8749–8764 (1985); Taylor et al., *Nucl. Acids Res.* 13:8765–8787 (1985); Nakamaye and Eckstein, *Nucl. Acids Res.* 14:9679–9698 (1986); Sayers et al., *Nucl. Acids Res.* 16:791–802 (1988); Sayers et al., *Nucl. Acids Res.* 16:803–814 (1988)), mutagenesis using uracil-containing templates (Kunkel, *Proc. Nat'l. Acad. Sci. USA* 82:488–492 (1985) and Kunkel et al., *Methods in Enzymol.* 154:367–382)); mutagenesis using gapped duplex DNA (Kramer et al., *Nucl. Acids Res.* 12:9441–9456 (1984); Kramer and Fritz, *Methods in Enzymol.* 154:350–367 (1987); Kramer et al., *Nucl. Acids Res.* 16:7207 (1988)); and Fritz et al., *Nucl. Acids Res.* 16:6987–6999 (1988)). Additional suitable methods include point mismatch repair (Kramer et al., *Cell* 38:879–887 (1984)), mutagenesis using repair-deficient host strains (Carter et al., *Nucl. Acids Res.* 13:4431–4443 (1985); Carter, *Methods in Enzymol.* 154:382–403 (1987)), deletion mutagenesis (Eghtedarzadeh and Henikoff, *Nucl. Acids Res.* 14:5115 (1986)), restriction-selection and restriction-purification (Wells et al., *Phil. Trans. R. Soc. Lond. A* 317: 415–423 (1986)), mutagenesis by total gene synthesis (Nambiar et al., *Science* 223:1299–1301 (1984); Sakamar and Khorana, *Nucl. Acids Res.* 14:6361–6372 (1988); Wells et al., *Gene* 34:315–323 (1985); and Grundström et al., *Nucl. Acids Res.* 13:3305–3316 (1985). Kits for mutagenesis are commercially available (e.g., Bio-Rad, Amersham International, Anglian Biotechnology).

Transfection and Staining of Cells for FACS Sorting

HeLa cells were seeded at $1 \times 10^6$ cells into 100 mm culture dishes, and transfected with 0.5 µg plasmid DNA 18–20 hours later. Transfections were performed using Superfect (Qiagen, Valencia, Calif.) according to the manufacturer's protocol. After incubating at 37° C. overnight, the cells were trypsinized, and stained for expression of the cell surface marker using mAb179, followed by phycoerythrin (PE)-labeled goat anti-mouse immunoglobulin (Ig) (Caltag; Burlingame, Calif.). Cells were sorted using a FACStar, or FACSVantage (Becton Dickinson; San Jose, Calif.) to collect those that expressed high levels of the mAb179 epitope and relatively low levels of EGFP. The staining concentration was determined for each labeled protein to provide a maximal Mean Fluorescence Intensity (MFI) and minimal background signal (e.g., optimum staining concentration was the concentration per $10^6$ cells). For a detailed description of flow cytometry cell sorting methods and staining methods, which are known in the art, see *Current Protocols in Immunology,* John Colligan et al., eds., Vols. I–IV (John Wiley & Sons, Inc., 2001 Supplement) and Rapley, R. and Walker, J. M. eds., *Molecular Biomethods Handbook* (Humana Press, Inc. 1998) [hereinafter "Rapley and Walker"], each of which is incorporated herein by reference in its entirety for all purposes.

HIRT Extraction of Plasmids

Plasmids were recovered from the sorted cells by Hirt preparation as follows. The sorted cells were pelletted by centrifugation, and resuspended in 125 microliter (µL) phosphate buffered saline (PBS). An equal volume of 2× HIRT buffer (1.2% sodium dodecyl sulfate (SDS), 20 milliMolar (mM) EDTA pH 8.0) was added to the cells and the cell samples incubated at room temperature for 15 minutes to allow the cells to lyse. After the addition of 62 µL 5 Molar (M) NaCl to give a final concentration of 1 M, the samples were placed at 4° C. overnight. The samples were then centrifuged at 14,000×g for 60 minutes (min) at 4° C., and the supernatant extracted with an equal volume of phenol-chloroform. The DNA was precipitated with cold ethanol, and washed with room temp 70% ethanol. Finally, the pellet was air dried, and the DNA resuspended in 10 mM Tris-HCl pH 7.4.

Preparing an "Enriched" Plasmid Library

Enriched plasmid libraries were prepared by transformation of XL-10 ultracompetent cells with DNA extracted by the HIRT method. Transformed cells were plated on agarose plates containing 40 µg/mL (40 micrograms/milliliter)Kanamycin, and incubated at 37° C. overnight. The resulting colonies were scraped, washed in LB, and plasmid DNA prepared using Qiagen's Endotoxin-free Maxiprep kits (Qiagen; Valencia, Calif.).

Plasmid Preparation in 96-well Format

Plasmid libraries were transformed into *E. coli* XL-10 ultracompetent cells, and spread on agar plates containing Kanamycin. Individual colonies were picked into 1.2 mL Terrific broth supplemented with Kanamycin in 96-well blocks. The block cultures were incubated for 20 hours at 37° C. with shaking. Bacteria were pelleted by centrifugation, and plasmids prepared robotically in a 96-well format. DNA yields were determined by reading optical densities (ODs) at 260 and 280 nanometer (nm) on a SpectraMax plate reader (Molecular Devices; Sunnyvale, Calif.). DNA concentrations typically varied between 100 and 200 ng/µL.

96-well Format Transfections of Mammalian Cells

HeLa cells were maintained in DMEM (Gibco; Grand Island, N.Y.) with 10% FCS (Hyclone; Logan, Utah), and Penicillin/Streptamycin. They were seeded at $2 \times 10^4$ cells/ well into 96-well plates, and transfected with 0.5–1 μg (micrograms) DNA 18 hours later using Qiagen's Superfect, according to the manufacturer's protocol. The cells were incubated at 37° C. for 20–24 hours, and stained for FACS analysis using mAb179 and PE-labelled goat anti-mouse Ig (Caltag; Burlingame, Calif.). Analysis was performed using a FACScan or FACSCalibur with CellQuest software (Becton Dickinson; San Jose, Calif.).

Construction of Vectors for Testing Wild-type CMV Promoters and Novel Chimeric Promoter Sequences in vivo The β-galactosidase gene was amplified by PCR from plasmid pCMVβ using the following Nhe1- and Apa1-encoding primers:

5'-AAG CTG GCT AGC ATG TCG TTT ACT TTG ACC AAC-3' (SEQ ID NO:36)

5'-AAA CGG GCC CTT ATT TTT GAC ACC AGA CCA AC-3' (SEQ ID NO:37)

The resulting fragment was digested with Apa1 and Nhe1 and cloned into plasmid pcDNA3.1.

Preparation of Plasmids for Injection into Mice

Plasmids for injection were prepared using Qiagen Endofree Maxiprep DNA kits (Qiagen; Valencia, Calif.), and resuspended in PBS at 0.1 or 0.2 mg/mL for injection. Each preparation was assayed for endotoxin using a Limulus Amebocyte Lysate assay kit (Biowhittaker; Walkersville, Md.), and contained less than 60 EU/· g (enzyme units/microgram) plasmid DNA.

Injection of Mice with Plasmid DNA

Mice were injected in the tibialis anterior (TA) muscle with a volume of 50 μL plasmid in PBS.

Collection and Preparation of Samples from Mice

Blood was collected from the lateral tail vein of mice, and serum harvested following centrifugation. Sera samples were stored at −20° C. until required for ELISA (Enzyme Linked Immunosorbent Assay). Individual TA muscles were excised, homogenized in 0.5 mL of Promega Cell Culture Lysis Reagent (Madison, Wis.), and the homogenates stored at −20° C. Samples were thawed, centrifuged at 1400×g at 4° C., and the supernatants collected to assay for Luciferase and protein content.

Injection of Human Fetal Muscle with Plasmid DNA

Human fetal limbs were obtained from (Advanced Biosciences Resources Inc.) for testing the activities of promoter sequences in human muscle. Plasmid DNA was diluted to 225 μg/300 μL of PBS and three aliquots of 100 μL each were injected into TA muscle. Muscle tissue was harvested after 48 hours, homogenized and assayed for Luciferase content using the Promega Luciferase Reporter Assay System described herein and as set forth in Promega Technical Bulletin No. 101 entitled "Luciferase Assay System" [hereinafter Promega Tech Bulletin No. 101], which is incorporated herein by reference in its entirety for all purposes.

Assay for Luciferase Gene Expression

The firefly luciferase gene is highly effective as a genetic reporter gene for measuring gene expression. The luciferase assay yields luminescence through an ATP-dependent oxidation of luciferin. Light intensity is a measure of the rate of catalysis by luciferase. Luciferase enzyme activity of the muscle tissue extract was measured on a microplate luminometer (or scintillation counter) using the Luciferase Reporter 1000 Assay System from Promega (Madison, Wis.), according to the manufacturer's instructions, as set forth in Promega Tech Bulletin No. 101. Luciferase enzyme assay methods described in Manthorpe, M. et al., *Human Gene Therapy* 4:419–431 (1993) [hereinafter Manthorpe et al.], which is incorporated herein by reference in its entirety for all purposes, can also be employed.

Figure 5:
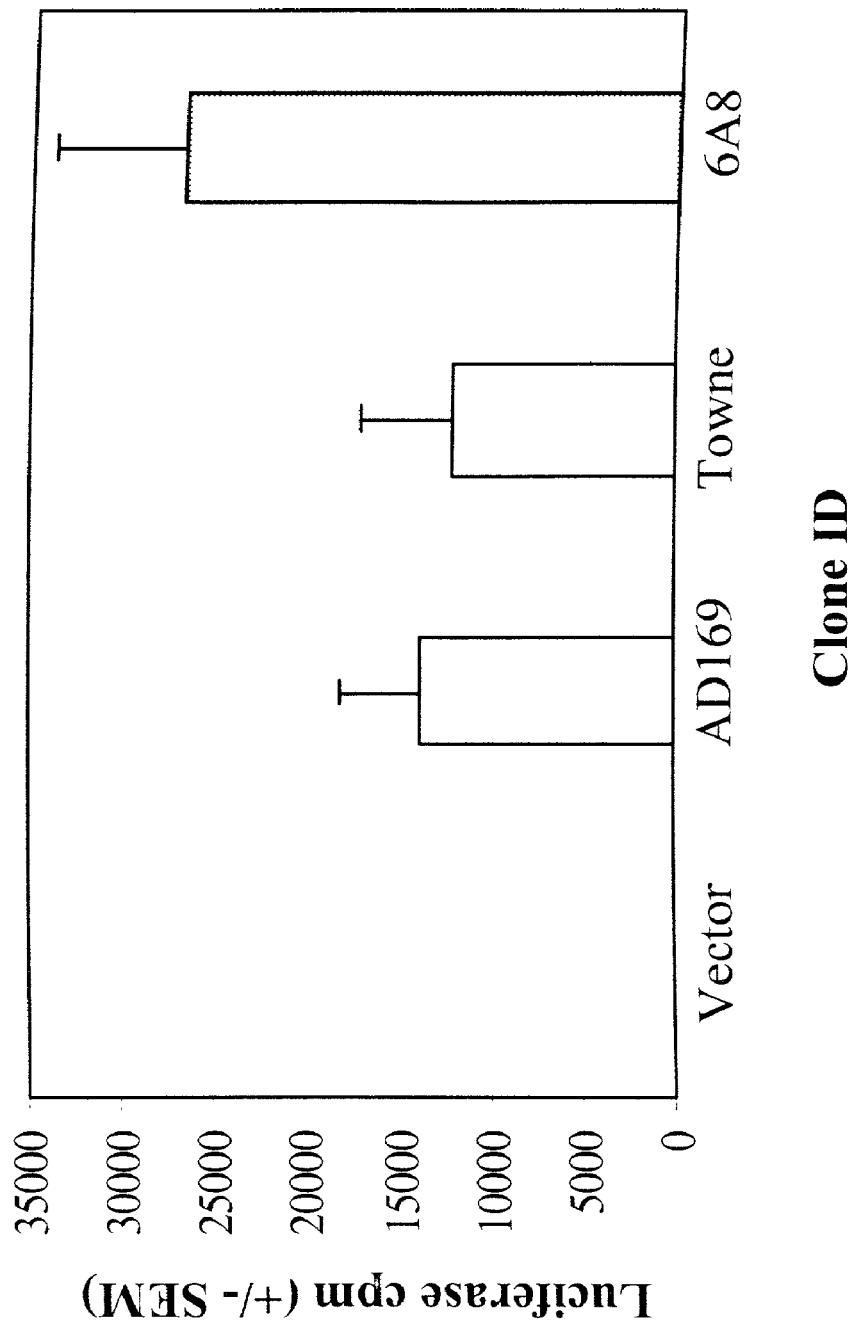
FIG. 5 shows a comparison of luciferase expression from a plasmid vector injected intramuscularly comprising a luciferase gene and a promoter sequence corresponding to clone 6A8 or a parental clone, where the luciferase gene was under the control of the promoter. Shuffled clone 6A8 gave 2-fold higher luciferase expression than did AD169 and Towne parental clones (p<0.05, t-test). Results are expressed as mean±SEM for 32 samples.

Measurement of Antibodies to β-galactosidase by ELISA

β-galactosidase ("βgal") antibody-containing serum samples were diluted in 96-well plates which had been coated with 4 μg/mL βgal (Sigma; St Louis, Mo.). Antibody binding (bound antibodies) was detected using peroxidase-conjugated anti-mouse IgG immunoglobulin (1/5000 dilution Sigma; St Louis, Mo.) followed by 3, 3', 5, 5' tetramethyl benzidine (TMB) substrate (Pierce; Rockford, Ill.). The reaction was stopped by the addition of 2 Normal (N) $H_2SO_4$, and the absorbance read at 450 nm on a SpectraMax plate reader (Molecular Dynamics; Sunnyvale, Calif.). End-point antibody titers were defined as the reciprocal of the highest dilution of serum giving detectable signal 3 standard deviations above background. FIG. 5 shows the results of reciprocal endpoint Ab titers (+/− SEM) for selected shuffled clone and parental clones. For a description of the ELISA assay screening method for anti-β-galactosidase antibodies used herein, which is known in the art, see *Current Protocols in Immunology*, John Colligan et al., eds., Vols. I–IV (John Wiley & Sons, Inc., 2001 Supplement), and Forg, P., *Gene Therapy* 5:7890797 (1998), each of which is incorporated herein by reference in its entirety for all purposes. As a control, uninjected mice were used. The vector control comprised a promoterless plasmid encoding β-galactosidase injected into mice in similar manner.

Results

Generation of a Library of Novel Chimeric Promoter Sequences

A library of chimeric promoter/enhancer sequences was created by family DNA shuffling of wild-type sequences from four related strains of CMV. The promoter and enhancer sequences were obtained by PCR from the AD169 and Towne human CMV strains. Similarly, the promoter and enhancer sequences were obtained from rhesus and vervet monkey CMVs by amplification. The promoter/enhancer nucleic acid sequences of the two human CMV strains are 97.5% identical, and share 50–70% identity with the nucleic acid sequences of the two monkey isolates, depending on the region of the sequence analyzed. (For example, the homology of these sequences was higher in the region of the transcription start site; see FIGS. 8 and 10.) The sequences taken together are referred to herein as "promoters."

The shuffled nucleotide sequences from the shuffled nucleotide library were cloned into plasmid pmAb179/GFP (SRα) and used to direct transcription of a marker gene (mAb179 epitope) in mammalian cells. The plasmid expression vector also encodes an internal marker (EGFP) under the control of the SRα promoter. This internal marker under the control of this promoter allows for analysis and sorting of cells harboring equal numbers of vectors.

Other expression markers (such as luciferase, β-galactosidase, lacZ, and green fluorescent protein) can also be used in this type of assay.

In vitro Screening of Libraries Comprising Novel Chimeric Promoter Sequences Resulting from Shuffling of CMV Promoter Sequences A tiered screening process was applied to the library to identify those shuffled (chimeric) sequences that gave the highest levels of reporter gene expression (FIG. 1). First, the plasmid library was enriched for good promoter sequences by transfection and FACS sorting those cells expressing the highest levels of marker gene, relative to expression of the internal marker to account for differences in plasmid vector copy numbers per cell. Plasmids were extracted from the sorted cells by HIRT preparation to generate "enriched libraries."

Figure 2:
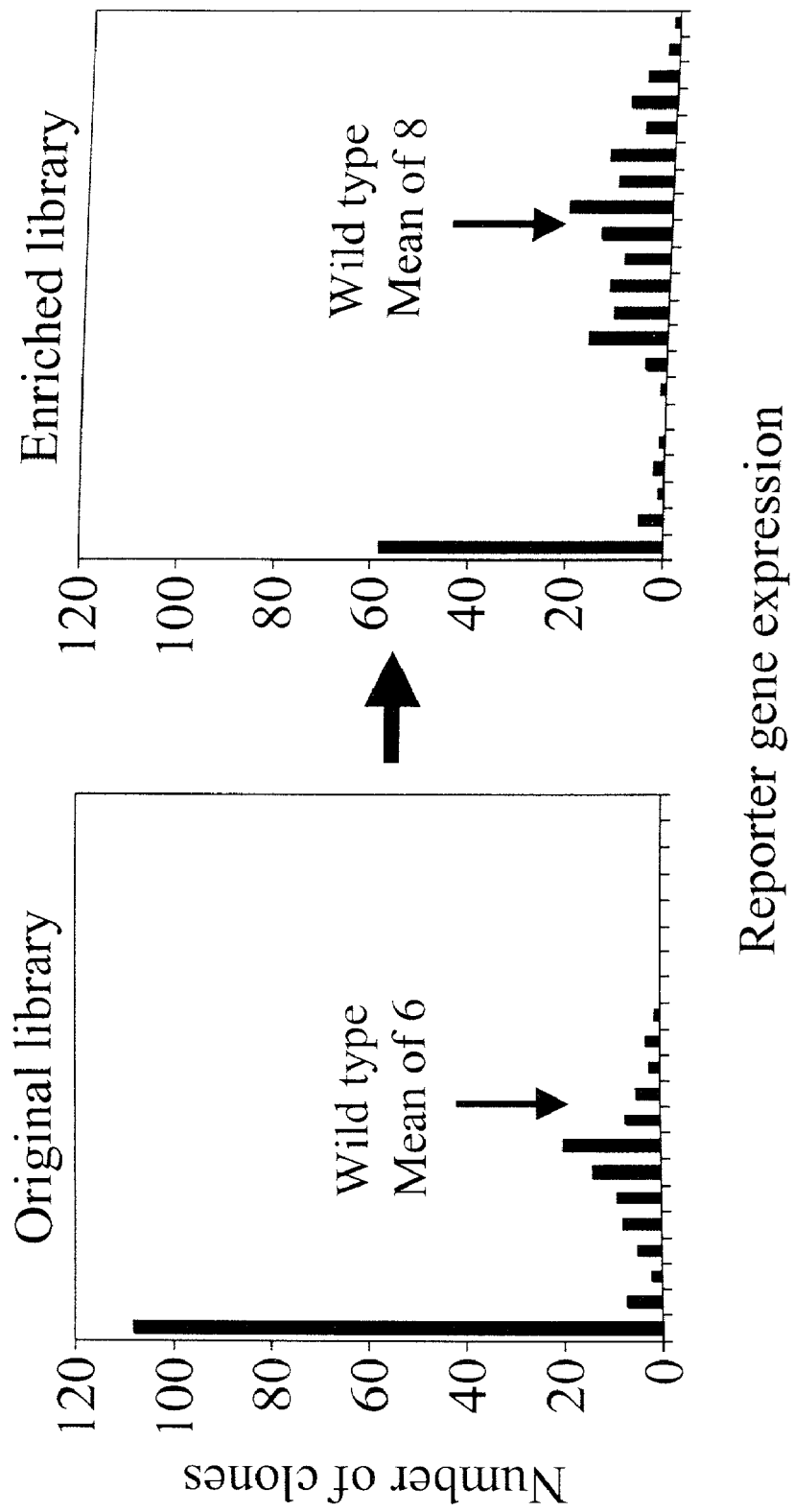
FIG. 2 shows that FACS sorting resulted in enrichment of the chimeric promoter libraries for chimeric promoters that provide a greater amount of reporter gene expression. Individual clones from the round 1 shuffled chimeric promoter library and the enriched library were assayed by transfection and FACS analysis. This analysis revealed a higher frequency of strongly expressing clones in the enriched library.

The increase in frequency of clones directing higher levels of transgene expression after just one round of FACS sorting is demonstrated in FIG. 2. Individual clones from the round 1 shuffled chimeric promoter library and the enriched library were included in plasmid vectors, the plasmid vectors introduced into mice, and mouse cells were subsequently assayed by FACS analysis. A plasmid comprising a shuffled nucleic acid sequence for each clone was introduced into mice. A plasmid comprising a wild-type (WT) human CMV promoter Towne strain nucleic acid sequence was introduced into 6 mice for comparison with the original library analysis of selected clones; a plasmid comprising a WT human CMV promoter Towne strain nucleic acid sequence was introduced into 8 mice for comparison with the enriched library analysis of selected clones. For each analysis, the mean value for the WT transfections is shown in FIG. 2 by the arrow in the graph. FIG. 2 shows the distribution of expression levels, as measured by flow cytometry, of individually analyzed CMV promoter clones in the original library versus the enriched FACS-sorted library. Cells were sorted using a FACStar or FACSVantage to collect those cells with clones that expressed high levels of the mAb179 epitope and relatively low levels of EGFP. Reporter gene expression was measured by the Mean Fluorescence Intensity (MFI) by standard FACS sorting methods. As shown in FIG. 2, the FACS-sorted library enriched the population for high-activity promoters. A higher frequency of strongly expressing clones was observed in the enriched library. In each graph in FIG. 2, a relatively high signal was shown for clones having no or little reporter gene expression; this signal likely corresponds to cells transfected with plasmids comprising dead or inactive promoters, cells transfected with plasmids lacking a promoter (i.e., control vector), and untransfected cells.

Figure 3:
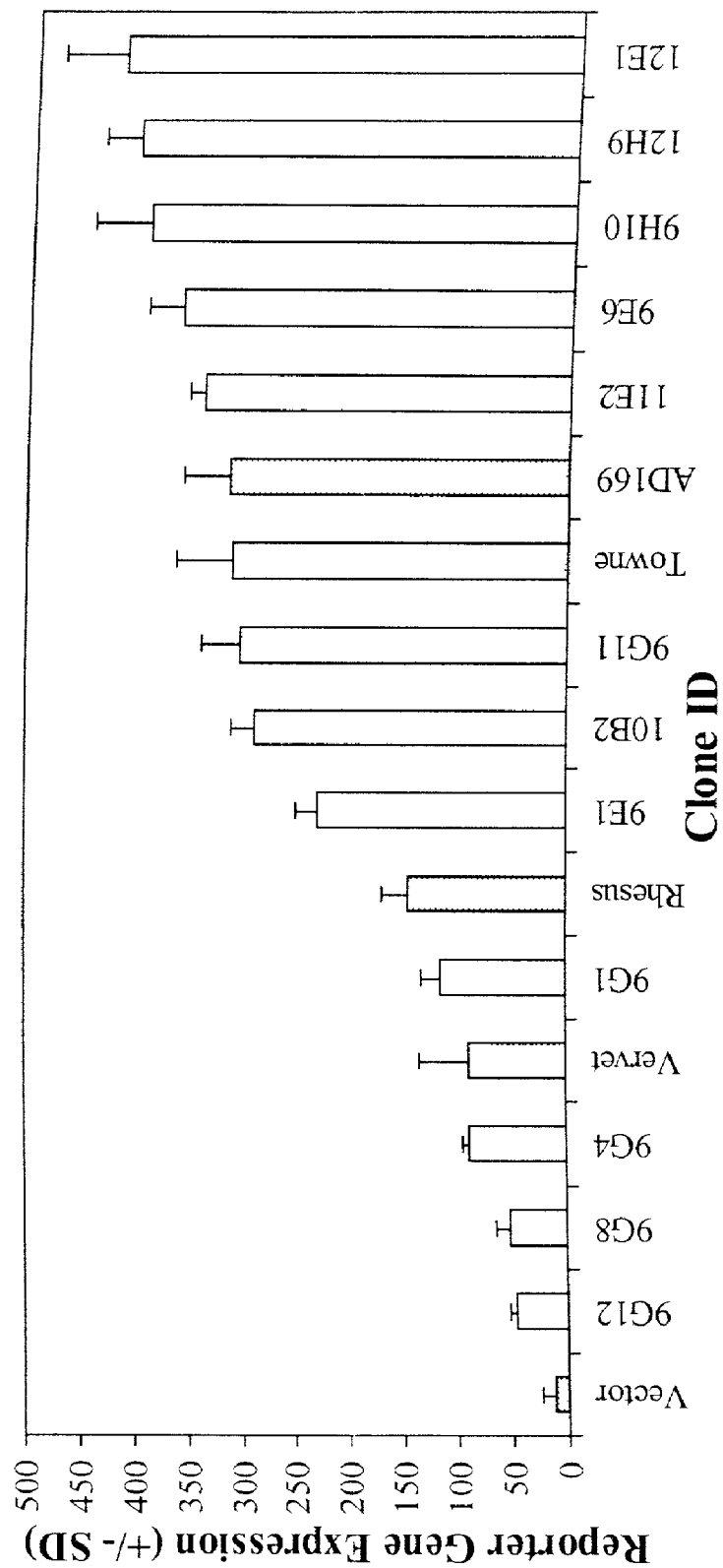
FIG. 3 shows that diverse activities of chimeric promoter sequences are obtained in transfected cells. Transfection and FACS analysis of individual clones revealed a large diversity of promoter activities in the chimeric promoter libraries. Results for vector control and parental clones are presented in lightly colored bars, dark bars represent shuffled clones. Results are expressed as mean ±SD for 4 independent transfections.

Plasmid DNA was then prepared robotically from individual clones (picked from the enriched libraries) for transfection of cells in 96-well trays. Cells were transfected with a plasmid DNA comprising a shuffled promoter nucleic acid sequence, a plasmid DNA comprising a wild-type parental promoter sequence, or a DNA vector lacking a promoter (which served as the vector control). Transfected cells were screened by FACS to determine the level of expression of the cells of the reporter gene (maker gene), relative to the internal marker. FACS screening identified those cells that expressed the highest levels of marker gene, relative to the internal marker. The results are shown in FIG. 3. The individual clone identification (Clone ID) names are shown along the X-axis (FIG. 3). Results for vector control and parental clones are presented in lightly shaded bars; dark bars represent shuffled clones. Results are expressed as mean ±SD (standard deviation) for 4 independent transfections. For each chimeric promoter clone, the level of expression of the reporter gene is shown. These assays revealed the diversity of promoter activities generated by DNA shuffling.

Two rounds of shuffling, enrichment by FACS sorting, and screening of individual clones in vitro were completed. Following enrichment of the first round library by FACS sorting, 1000 individual clones were screened by transfection and FACS analysis; the best 18 clones from these assays were chosen as starting sequences for generating a second round library. This library was enriched by two successive rounds of FACS sorting before 1000 individual clones were screened in transfection and FACS assays.

In vivo Screening of Libraries Comprising Novel Chimeric Promoter Sequences Resulting from Shuffling of CMV Promoters Thirty of the chimeric promoter sequences that produced the highest levels of expression of the reporter genes in the in vitro analyses were subcloned into DNA vaccine vectors encoding a reporter molecule (i.e., Luciferase or β-galactosidase) for in vivo studies of gene expression and immune response. The chimeric promoter sequences were positioned to drive expression of the respective reporter genes. Each chimeric promoter sequence was operably linked to a Luciferase or β-galactosidase gene.

Individual plasmid preparations comprising a promoter sequence operably linked to a reporter gene were inoculated intramuscularly (via the tibialis anterior (TA) muscle) into groups of 5 to 10 mice for each clone. Plasmids comprising a parental sequence operably linked to the luciferase reporter gene were also injected into groups of mice in a similar manner (for each of the four parental sequences) and used for comparison with the plasmids comprising chimeric promoter sequences. As a vector control, an empty vector including the luciferase reporter gene, but lacking a promoter, was injected into mice in a similar manner. A group of mice that were not inoculated with any vector served as a control group ("Control"). Expression of luciferase in homogenates of the TA muscle and serum antibody titers against β-galactosidase were then measured as an indication of promoter activity. From these results, 5 luciferase clones and 6 β-galactosidase clones were chosen for further studies to confirm the activities of the promoter sequences in vivo.

1. In Vivo Screening Assay to Detect Luciferase Gene Expression

Figure 4:
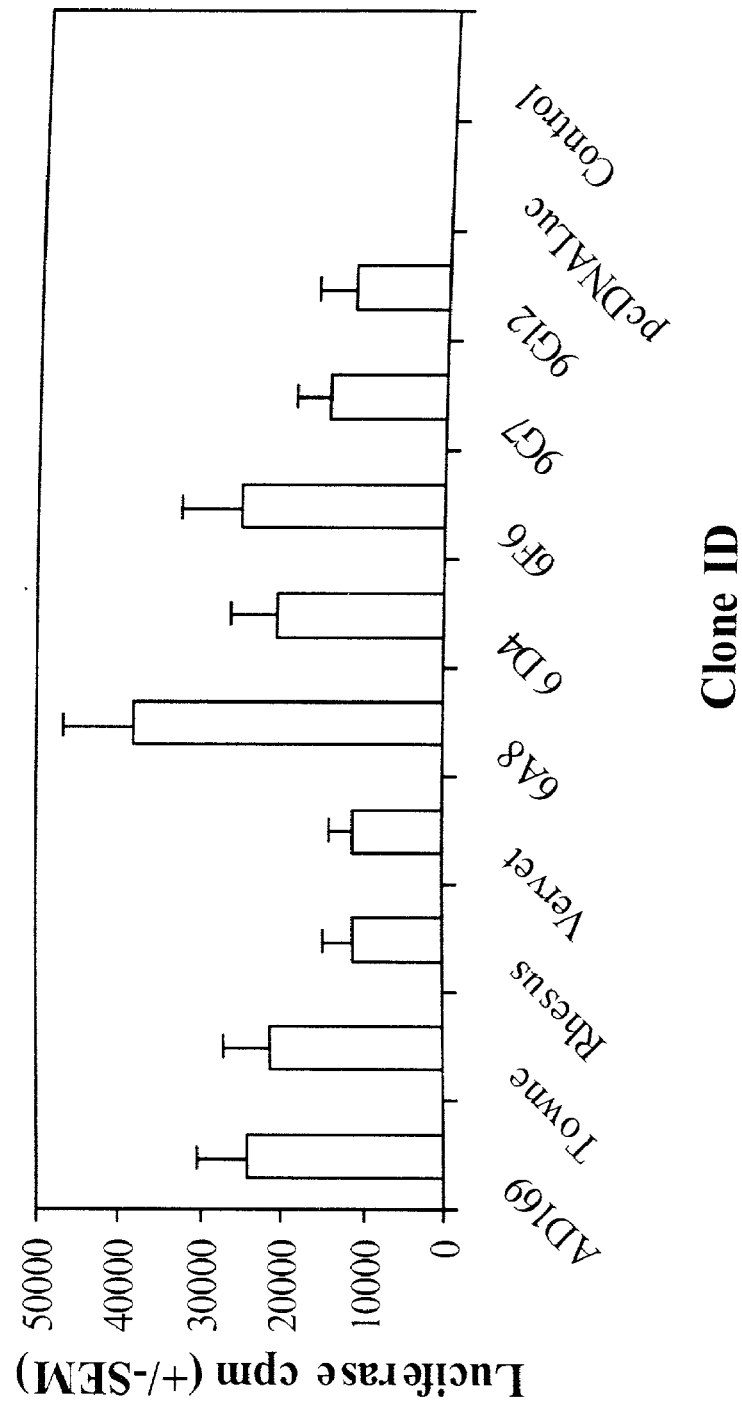
FIG. 4 shows the amount of luciferase expression obtained in muscle 7 days after injection of a plasmid expression vector that comprised a luciferase gene under the control of a shuffled versus a control CMV promoter. Mice were injected with 10 µg plasmid in each tibialis anterior (TA) muscle; muscles were collected at 7 days post-injection, homogenized, and the luciferase content assayed. Results are expressed as mean±SEM for 32 samples.

The amount of Luciferase expression in TA muscles of mice was determined at various time point(s) after injection. In the present example, the amount Luciferase expression in TA muscles was measured 7 days after injection of 10·g plasmid per muscle (FIG. 4). The linear range of light production was determined according to the manufacturer's instructions (Promega Tech Bulletin No. 101). Cell extracts were prepared and assays were performed according to the manufacturer's instructions (Promega Tech Bulletin No. 101). Light production by luciferase (luciferase activity) was measured according to the manufacturer's instructions (Promega Tech Bulletin No. 101) by relative light units (light intensity) using a luminometer or scintillation counter (reflected as counts per minute (cpm) (+/−SEM) (standard error of the mean)). See also Manthorpe et al., supra. Results are shown in FIGS. 4 and 5. In FIG. 4, results are expressed as mean±SEM for 32 samples.

The transgene (reporter) expression by shuffled promoters was statistically significantly higher in selected clones than that induced by one or more of the four parental wild-type promoters. Shuffled clone 6A8 was found to give the highest levels of Luciferase expression of the chimeric promoter sequences tested, and performed approximately 2-fold better than the best parental sequences, human AD169 and Towne ($p<0.05$, t-test), as is shown in FIG. 5. Results are expressed as mean ±SEM for 32 samples. Clones 6D4 and 6F6 yielded levels of luciferase similar to that observed with the parental sequences, with clones 9G7 and 9G12 giving lower levels, comparable to the Rhesus and Vervet parental sequences (FIG. 4). Luciferase expression from a promoterless luciferase-encoding plasmid vector (pcDNALuc) was negligible. The control mice (non-injected) also showed no measurable expression levels.

2. In Vivo ELISA Screening Assay for Anti-β-Galactosidase Antibodies

Figure 6:
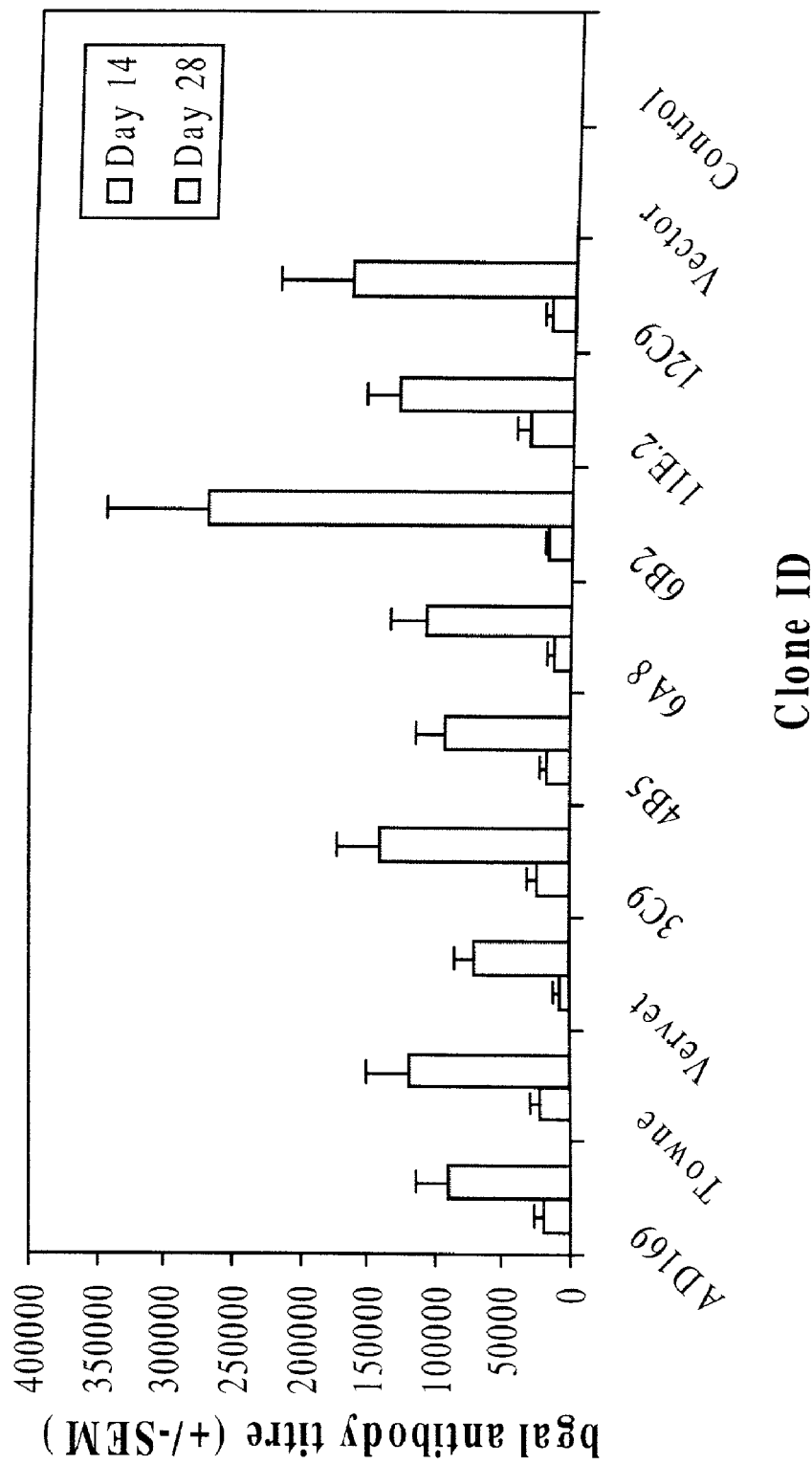

Mice were injected with 10 µg β-galactosidase-encoding plasmids on days 0 and 15, and serum collected on days 14 and 28 for measurement of anti β-galactosidase antibodies. Plasmids comprising a AD169, Towne, or Vervet parental nucleic acid sequence operably linked to β-galactosidase nucleic acid sequence were also injected into groups of mice in a similar manner and used for comparison with the plasmids comprising the chimeric promoter sequences. As a vector control, an empty vector comprising a promoterless (β-galactosidase-encoding plasmid (pcDNAβ-gal) was injected into mice in a similar manner. A group of mice that were not inoculated with any vector served as a control group. FIGS 6A and 6B shows the antibody titer levels measured in serum by ELISA methods, where the serum was obtained following injection of mice with β-galactosidase-encoding plasmids (10 µg or 4 µg plasmid, respectively) at the time (day) noted above.

Injection of the shuffled clone, 11E2, gave the strongest antibody response against β-galactosidase at day 14 post-injection, while clone 6B2 gave the strongest response at day 28 post-injection. Results are expressed as mean ±SEM for 8–20 samples.

Antibody titers in mice injected with clone 6B2 were approximately 2-fold higher than in those injected with clones carrying the (best) wild-type parental promoters. Clone 6B2 displayed about a 2-fold higher transgene expression in vivo than the parental promoters. All other chimeric clones tested gave comparable antibody titers at day 28 to the parental clones. Mice injected with promoterless β-galactosidase-encoding plasmid gave a negligible antibody response. The control group of mice (uninjected) also showed negligible antibody response.

Assessment of Novel Chimeric Promoter Function in Human Muscle

Figure 7:
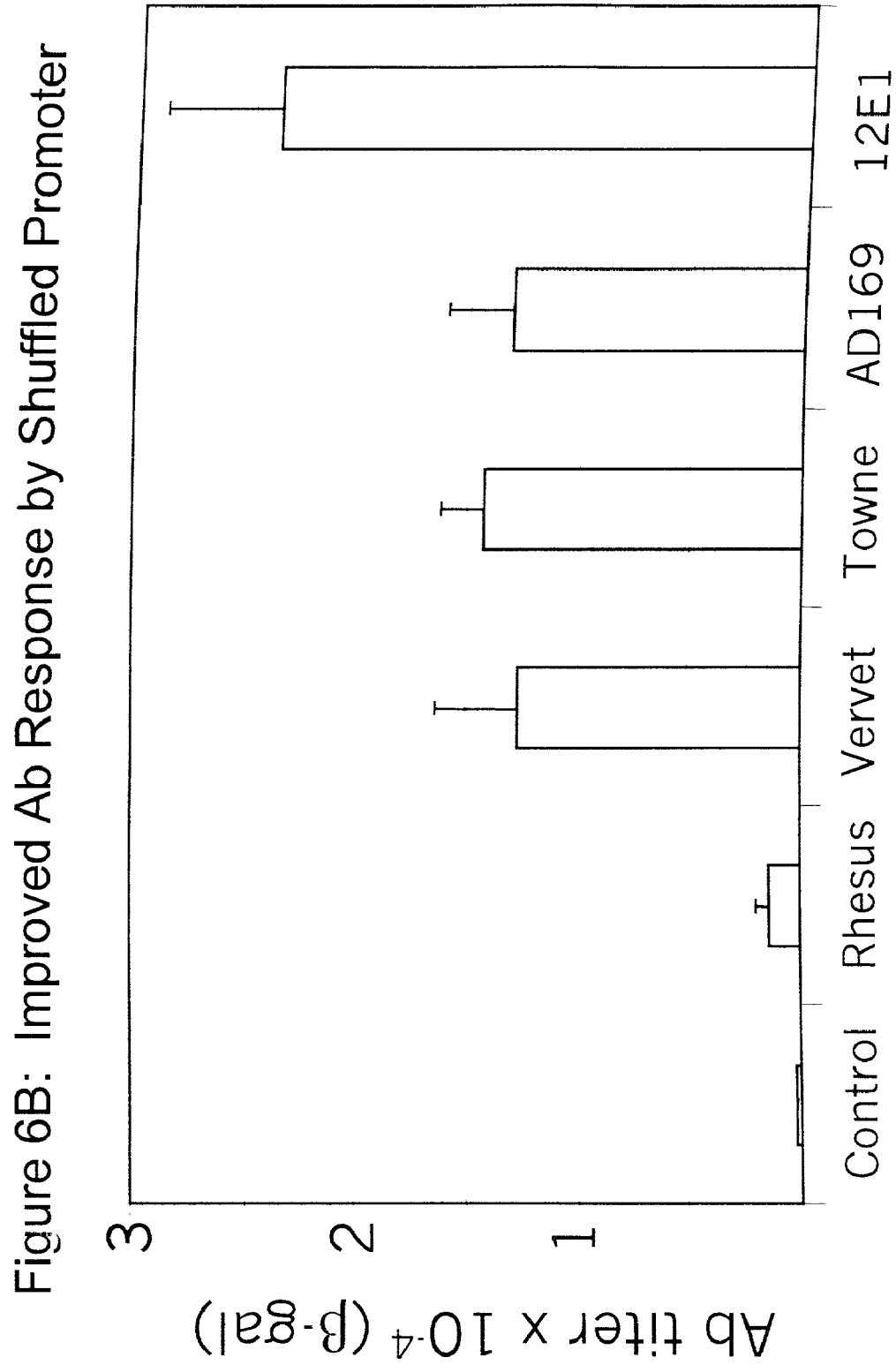
FIG. 7 shows that the chimeric promoter 6A8 is functional in human muscle tissue. Luciferase was measured in homogenates of human fetal muscle 2 days after injection of luciferase-encoding plasmids. Results are expressed as mean ±SEM for 3–6 injections for each clone.

The expression of Luciferase in human fetal muscle tissue was assessed following injection into such tissue of a DNA plasmid comprising a luciferase gene and the nucleic acid sequence corresponding to clone 6A8 or parental human clone AD169 or Towne. A similar plasmid vector, but lacking a promoter, was injected in a similar manner as a control vector. Luciferase levels in samples of the homogenate of human fetal muscle prepared 2 days after injection of luciferase-encoding plasmids were measured; these levels were found to be comparable and significantly higher than observed in samples from muscles injected with the promoterless vector (FIG. 7). Results are expressed as mean ±SEM for 3–6 injections for each clone. FIG. 7 confirms that the chimeric promoter 6A8 was functional in human muscle tissue.

Analysis of Chimeric Promoter DNA Sequences for High-level Expression

Sequence analysis of selected shuffled chimeric promoters revealed that they comprised mainly nucleic acid sequences from the AD169 and Towne human parental nucleic acid sequences. In addition, the sequences contain between 2 and 17 unique nucleotides throughout the promoter. Deletions of one or two nucleotides occur in several of the clones, and 11E2 also has an additional nucleotide (nt) after nt853 (numbering is based on the consensus sequence as shown in FIGS. 8A–8I). Clones 6F6, 9G7, 11E2, and 12C9 contain nucleotide sequences derived from the Rhesus monkey exon A approximately from nt817 (which is close to the transcription start site) to nt863. Clones 4B5, 6B2, 6D4, and 12E1 have a deletion corresponding to the region 684–735 nucleotides in the consensus sequence. Clone 12C9 is truncated at nucleotide (nt) residue 909 (numbered according to the consensus sequence shown in FIGS. 8A–8I). Notably, clone 12C9 gave a comparable or increased antibody response in the B-gal screening assay relative to other chimeric clones or the parental sequences despite having a truncated sequence. Compared with the human AD169 and Towne nucleic acid sequences, the 12C9 nucleic acid sequence lacks a short segment of the nucleic acid sequence corresponding to the first exon and intron of each of the AD169 and Towne strains.

There is also a deletion in clone 9E1 corresponding to nucleotides 319 to 512 in the parental clones. In all of the shuffled sequences, the TATA box (or TATATAA box), (CAAT (or CAAAT box) box and transcription start site (T=thymine, C=cytosine, A=adenine nucleotide bases) are identical to those found in the AD169 and Towne parental sequences (see FIGS. 8A–8I). For known CMV promoters, it is generally believed the TATA box is important for promoter activity.

Several of these mutations occur in regions of repeated elements that occur in the CMV enhancer and are rich in transcription factor binding sites. Most notable is the deletion in clone 9E1 from nucleotides 319 to 512, which eliminates a whole 21 bp repeat element, and parts of two others, three 19 bp repeat elements, and one each of the 18 and 16 bp repeat elements. This likely accounts for the low expression of the mAb179 epitope reporter gene when cells were transfected with clone 9E1.

Screening of Chimeric Promoter DNA Sequences for Low- or Intermediate-level Transgene Expression A library of chimeric promoter sequences with diverse activities by DNA shuffling of CMV promoters sequences from four related strains of CMV promoter (two human strains, Towne and AD 169; and Vervet and Rhesus monkey strains) were generated using methods described above. For example, the major IE region promoter/enhancer regions of the resulting library of chimeric promoter nucleic acids was screened to identify those chimeric variants that gave a level expression of reporter genes in vitro lower than the reporter gene expression level produced by one of the parental genes, using the procedures outlined above.

Those chimeric promoter clones identified as directing lower levels of reporter gene expression in vitro were individually isolated, cloned into plasmid vectors, and transfected in vivo into mammalian cells. The cells were screened to identify those chimeric variants that gave high-level expression of reporter genes in vivo.

While the foregoing invention has been described in some detail for purposes of clarity and understanding, it will be clear to one skilled in the art from a reading of this disclosure that various changes in form and detail can be made without departing from the true scope of the invention. It is understood that the examples and embodiments described herein are for illustrative purposes only and that various modifications or changes in light thereof will be suggested to persons skilled in the art and are to be included within the spirit and purview of this application and scope of the appended claims. For example, all the techniques and apparatus described above may be used in various combinations. All publications, patents, patent applications, and/or other documents cited in this application are incorporated herein by reference in their entirety for all purposes to the same extent as if each individual publication, patent, patent application, and/or other document were individually indicated to be incorporated herein by reference in its entirety for all purposes.

What is claimed is:

1. An isolated or recombinant nucleic acid comprising a polynucleotide sequence that has at least 99% sequence identity to the entire length of the polynucleotide sequence of SEQ ID NO:8 or the complementary polynucleotide sequence thereof, wherein said polynucleotide sequence promotes expression of a nucleic acid encoding a polypeptide to which the polynucleotide sequence is operably linked.

2. The nucleic acid of claim 1, wherein the nucleic acid comprises the polynucleotide sequence of SEQ ID NO:8 or the complementary polynucleotide sequence thereof.

3. The nucleic acid of claim 1, comprising a polynucleotide sequence that has at least 99.5% sequence identity to the polynucleotide sequence of SEQ ID NO:8 or the complementary polynucleotide sequence thereof.

4. An isolated or recombinant nucleic acid comprising a subsequence of the polynucleotide sequence of SEQ ID NO:8, said subsequence comprising nucleic acid residues 1 to 907 of SEQ ID NO:8, or the complementary polynucleotide sequence thereof.

5. The nucleic acid of claim 4, wherein the subsequence promotes the expression of a nucleic acid encoding a polypeptide to which the subsequence is operably linked.

6. The nucleic acid of claim 1, wherein the nucleic acid comprises a deletion of one or more nucleotide residues at nucleotide residue positions 829–834 or 840–843 of SE ID NO:8, or the complementary polynucleotide sequence thereof.

7. The nucleic acid of claim 6, wherein the nucleic acid comprises a deletion of the nucleotide residues at nucleotide residue positions 829–834 or 840–843 of SEQ ID NO:8, or the complementary polynucleotide sequence thereof.

8. The nucleic acid of claim 7, wherein the nucleic acid comprises a deletion of the nucleotide residues at nucleotide residue positions 829–834 and 840–843 of SEQ ID NO:8, or the complementary polynucleotide sequence thereof.

9. The nucleic acid of claim 1, wherein the nucleic acid comprises an insertion of a nucleotide residue, as compared to the human Towne CMV promoter polynucleotide sequence shown in SEQ ID NO:20, after the nucleotide residue at position 852 of SEQ ID NO: 8, or the complementary polynucleotide sequence thereof.

10. An isolated or recombinant nucleic acid comprising a polynucleotide sequence having at least 99% sequence identity to a nucleotide sequence which comprises the sequence of SEQ ID NO:8 with a deletion of one or more nucleotide residues at nucleic acid residue positions 683–734 of SEQ ID NO:8 or the complementary polynucleotide sequence thereof, wherein said polynucleotide sequence promotes expression of a nucleic acid encoding a polypeptide to which the polynucleotide sequence is operably linked.

11. The isolated or recombinant nucleic acid of claim 10, wherein the isolated or recombinant nucleic acid comprises a polynucleotide sequence having at least 99% sequence identity to a nucleotide sequence which comprises the sequence of SEQ ID NO:8 with a deletion of the nucleotide residues at nucleotide residue positions 683–734 of SEQ ID NO:8 or the complementary polynucleotide sequence thereof.

12. An isolated or recombinant nucleic acid, wherein the nucleic acid comprises a polynucleotide sequence comprising the nucleic acid residues 1 to 930 of the consensus sequence shown in SEQ ID NO:21.

13. The nucleic acid of claim 12, wherein the nucleic acid comprises a polynucleotide sequence comprising the nucleic acid residues 1 to 932 of the consensus sequence shown in SEQ ID NO:21.

14. An isolated or recombinant nucleic acid comprising a polynucleotide sequence having at least 99% sequence identity to a nucleotide sequence which comprises the sequence of SEQ ID NO:8 with a deletion of one or more nucleotide residues at nucleotide residue positions 319–511 of SEQ ID NO:8, or the complementary polynucleotide sequence thereof, wherein said polynucleotide sequence promotes expression of a nucleic acid encoding a polypeptide to which the polynucleotide sequence is operably linked.

15. The isolated or recombinant nucleic acid of claim 14, wherein the isolated or recombinant nucleic acid comprises a polynucleotide sequence having at least 99% sequence identity to a nucleotide sequence which comprises the sequence of SEQ ID NO:8 with a deletion of the nucleotide residues at nucleotide residue positions 319–511 of SEQ ID NO:8, or the complementary polynucleotide sequence thereof.

16. The nucleic acid of claim 1, wherein the polynucleotide sequence is operably linked to a nucleic acid encoding a polypepride to form an expression cassette.

17. The nucleic acid of claim 16, wherein the polypeptide-encoding nucleic acid encodes a polypeptide selected from the group consisting of a viral polypeptide, an immunogen, an immunomodulatory molecule, an antigen, an adjuvant, an allergen, an antibody, a bacterial toxin, a cytokine, a cytokine receptor, an enzyme, and a co-stimulatory molecule.

18. The nucleic acid of claim 17, wherein the polypeptide-encoding nucleic acid encodes an antigen selected from the group consisting of a cancer antigen, a hepatitis B surface antigen, a hepatitis A antigen, and a hepatitis C antigen.

19. The nucleic acid of claim 17, wherein the polypeptide encoding nucleic acid encodes a co-stimulatory polypeptide that binds to a CD28 or CTLA-4 receptor.

20. A vector comprising at least one nucleic acid of claim 1.

21. The vector of claim 20, wherein the vector is an expression vector.

22. The vector of claim 20, wherein the vector is selected from a plasmid, a cosmid, a phage, a virus or fragment thereof, a bacterial artificial chromosome (BAC), a yeast artificial chromosome (YAC).

23. An isolated or cultured cell comprising the nucleic acid of claim 1.

24. The cell of claim 23, wherein the cell comprises a human cell.

25. A method of producing a polypeptide, the method comprising:
(a) providing a population of cells comprising a nucleic acid of claim 1 operably linked to a nucleic acid encoding a polypeptide; and
(b) expressing the polypeptide in at least a subset of the population of cells or progeny thereof.

26. The method of claim 25, wherein the population of cells is provided by introducing the nucleic acid operably linked to the polypeptide-encoding nucleic acid into the population of cells.

27. The method of claim 25, further comprising isolating the polypeptide from the cells.

28. The method of claim 25, wherein the cells are in culture.

29. The method of claim 28, comprising expressing the polypeptide by culturing the population or subset of the population of cells or progeny thereof in a nutrient medium under conditions in which the nucleic acid promotes expression of the polypeptide.

30. The method of claim 29, further comprising isolating or recovering the polypeptide from the cells or from the nutrient medium.

31. A kit comprising a nucleic acid of claim 1.

32. A kit comprising a vector of claim 20.

33. An isolated or recombinant nucleic acid comprising a polynucleotide sequence that has at least 99% sequence identity to a nucleotide sequence which comprises the sequence of SEQ ID NO:8 but lacks the nucleotide residues of the first exon, or the complementary polynucleotide sequence thereof, wherein the polynucleotide sequence promotes expression of a nucleic acid encoding a polypeptide to which the polynucleotide sequence is operably linked.

34. The nucleic acid of claim 1, wherein the polynucleotide sequence or complementary polynucleotide sequence thereof promotes expression of a polypeptide-encoding nucleic acid in a mammalian cell, wherein said polypeptide is capable of inducing an immune response.

35. A vector for expression of a polypeptide in a mammalian cell comprising a promoter, said promoter comprising a polynucleotide sequence having at least 99% sequence identity to the entire length of the sequence of SEQ ID NO:8, wherein said promoter is capable of directing transcription of a heterologous coding sequence operably linked downstream of the polynucleotide sequence of the promoter.

36. The vector of claim 35, wherein the polynucleotide sequence of the promoter is linked directly to the heterologous coding sequence.

37. The vector of claim 35, further comprising an origin of replication positioned upstream of and operably linked to the polynucleotide sequence of the promoter.

38. The vector of claim 35, further comprising a polyadenylation region positioned downstream of and operably linked to the polynucleotide sequence of the promoter.

39. An isolated or cultured cell transfected with a vector comprising the vector of claim 35.

40. The isolated or cultured cell of claim 39, wherein the cell is a mammalian cell.

41. A vector comprising at least one nucleic acid of claim 2.

42. A vector comprising at least one nucleic acid of claim 3.

43. The nucleic acid of claim 10, wherein the polynucleotide sequence has at least 99.5% sequence identity to a nucleotide sequence which comprises the sequence of SEQ ID NO:8 with a deletion of one or more nucleotide residues at nucleic acid residue positions 683–734 of SEQ ID NO:8, or the complementary polynucleotide sequence thereof.

44. The nucleic acid of claim 14, wherein the polynucleotide sequence has at least 99.5% sequence identity to a nucleotide sequence which comprises the sequence of SEQ ID NO:8 with a deletion of one or more nucleotide residues at nucleotide residue positions 319–511 of SEQ ID NO:8, or the complementary polynucleotide sequence thereof.

45. The vector of claim 35, wherein said promoter comprises a polynucleotide sequence having at least 99.5% sequence identity to the entire length of the sequence of SEQ ID NO:8, or the complementary polynucleotide sequence thereof.

46. The nucleic acid of claim 44, wherein the polynucleotide sequence has at least 99.5% sequence identity to a nucleotide sequence which comprises the sequence of SEQ ID NO:8 with a deletion of the nucleotide residues at nucleotide residue positions 319–511 of SEQ ID NO:8, or the complementary polynucleotide sequence thereof.

* * * * *

UNITED STATES PATENT AND TRADEMARK OFFICE
CERTIFICATE OF CORRECTION

PATENT NO. : 7,074,590 B2 Page 1 of 1
APPLICATION NO. : 09/886942
DATED : July 11, 2006
INVENTOR(S) : Juha Punnonen et al.

It is certified that error appears in the above-identified patent and that said Letters Patent is hereby corrected as shown below:

In claim 6, Column 95, line 9, delete "SE ID" and insert --SEQ ID--.

In claim 16, Column 96, line 3, delete "polypepride" and insert --polypeptide--.

Signed and Sealed this

Tenth Day of October, 2006

JON W. DUDAS
*Director of the United States Patent and Trademark Office*